(12) United States Patent
Turner et al.

(10) Patent No.: US 8,993,234 B2
(45) Date of Patent: *Mar. 31, 2015

(54) NANOPORE SEQUENCING USING CHARGE BLOCKADE LABELS

(71) Applicant: Pacific Biosciences of California, Inc., Menlo Park, CA (US)

(72) Inventors: Stephen Turner, Seattle, WA (US); Jeffrey Wegener, Cupertino, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,411

(22) Filed: Jun. 27, 2014

(65) Prior Publication Data

US 2014/0364324 A1 Dec. 11, 2014

Related U.S. Application Data

(63) Continuation of application No. 13/083,320, filed on Apr. 8, 2011.

(60) Provisional application No. 61/322,777, filed on Apr. 9, 2010, provisional application No. 61/391,500, filed on Oct. 8, 2010, provisional application No. 61/415,213, filed on Nov. 18, 2010.

(51) Int. Cl.
*C12Q 1/68* (2006.01)
*G01N 27/447* (2006.01)
*G01N 33/487* (2006.01)

(52) U.S. Cl.
CPC ............ *C12Q 1/6869* (2013.01); *G01N 27/447* (2013.01); *C12Q 1/68* (2013.01); *G01N 27/44791* (2013.01); *G01N 33/48721* (2013.01)
USPC .......................................................... 435/6.1

(58) Field of Classification Search
CPC ....................................................... C12Q 1/68
USPC ......................................................... 435/6.1
See application file for complete search history.

(56) References Cited

U.S. PATENT DOCUMENTS

| | | | |
|---|---|---|---|
| 4,720,786 A | 1/1988 | Hara | |
| 5,795,782 A | 8/1998 | Church et al. | |
| 6,015,714 A | 1/2000 | Baldarelli et al. | |
| 6,056,922 A | 5/2000 | Ikamatsu | |
| 6,362,002 B1 | 3/2002 | Denison et al. | |
| 6,673,615 B2 | 1/2004 | Denison et al. | |
| 7,211,789 B2 | 5/2007 | Berstis | |
| 7,258,838 B2 | 8/2007 | Li et al. | |
| 7,312,046 B2 | 12/2007 | Chin et al. | |
| 7,488,671 B2 | 2/2009 | Corderman et al. | |
| 7,625,701 B2 | 12/2009 | Williams et al. | |
| 8,324,914 B2 | 12/2012 | Chen et al. | |
| 8,652,779 B2* | 2/2014 | Turner et al. ................ | 435/6.1 |
| 2002/0197618 A1 | 12/2002 | Sampson | |
| 2003/0232346 A1 | 12/2003 | Su | |
| 2006/0063171 A1 | 3/2006 | Akeson et al. | |
| 2006/0231419 A1 | 10/2006 | Barth et al. | |
| 2006/0246497 A1 | 11/2006 | Huang et al. | |
| 2007/0048745 A1 | 3/2007 | Joyce et al. | |
| 2007/0099191 A1 | 5/2007 | Nair et al. | |
| 2007/0205098 A1 | 9/2007 | Ehrismann et al. | |
| 2007/0298511 A1 | 12/2007 | Kang et al. | |
| 2008/0041733 A1 | 2/2008 | Hibbs et al. | |
| 2008/0218184 A1 | 9/2008 | White et al. | |
| 2008/0254995 A1 | 10/2008 | Kim et al. | |
| 2008/0311582 A1 | 12/2008 | Bayley et al. | |
| 2009/0029477 A1 | 1/2009 | Meller et al. | |
| 2010/0289505 A1 | 11/2010 | Zhang et al. | |
| 2010/0331194 A1 | 12/2010 | Turner et al. | |
| 2011/0014612 A1 | 1/2011 | Hendricks et al. | |
| 2011/0081647 A1 | 4/2011 | Siddiqi et al. | |
| 2013/0240359 A1* | 9/2013 | Turner et al. ................ | 204/451 |
| 2014/0051069 A1 | 2/2014 | Jayasinghee et al. | |

FOREIGN PATENT DOCUMENTS

| | | |
|---|---|---|
| EP | 1712909 A1 | 10/2006 |
| WO | 0028312 A1 | 5/2000 |
| WO | 2008102121 A1 | 8/2008 |
| WO | 2009077734 A2 | 6/2009 |

(Continued)

OTHER PUBLICATIONS

Astier et al. "Toward Single Molecule DNA Sequencing: Direct Identification of Ribonucleoside andd Deoxyribonucleoside 5'-Monophosphates by Using an Engineered Protein Nanopore Equipped with a Molecular Adapter" JACS (2006) 128:1705-1710.

Austin et al. "Fabrication of 5nm linewidth and 14 nm pitch features by nanoimprint lithography" Apps Phys Lett (2004) 84(26):5299-5301.

Bayley et al. "Nanotechnology: Holes with an edge" Nature (2010) 567:164-165.

Benner et al. "Sequence-specific detection of individual DNA polymerase complexes in real time using a nanopore" NNano (2007) 2:718-724.

(Continued)

*Primary Examiner* — Ardin Marschel
(74) *Attorney, Agent, or Firm* — Robert H. Reamey

(57) ABSTRACT

The invention relates to devices and methods for nanopore sequencing. The invention includes compositions and methods of nucleic acid sequencing using a single polymerase enzyme complex comprising a polymerase enzyme and a template nucleic acid attached proximal to a nanopore, and nucleotide analogs in solution comprising charge blockade label that are attached to the polyphosphate portion of the nucleotide analog such that the charge blockade labels are cleaved when the nucleotide analog is incorporated into a growing nucleic acid and the charge blockade label is detected by the nanopore to determine the presence and identity of the incorporated nucleotide and thereby determine the sequence of a template nucleic acid.

21 Claims, 23 Drawing Sheets

(56) References Cited

FOREIGN PATENT DOCUMENTS

| WO | 2010086603 A1 | 8/2010 |
|---|---|---|
| WO | 2012083249 A2 | 6/2012 |
| WO | 2012083249 A3 | 6/2012 |

OTHER PUBLICATIONS

Branton et al. "The potential and challenges of nanopore sequencing" Nat Biotech (2008) 26(10):1146-1153.
Chang et al. "Electronic signatures of all four DNA nucleosides in a tunneling gap" Nano Lett (2010) 10:1070-1075.
Chen et al. "Atomic layer deposition to fine-tune the surface properties and diameters of fabricated nanopores" Nano Lett (2004) 4(7):1333-1337.
Chou et al. "Electrodeless dielectrophoresis of single- and double-stranted DNA" Biophys J (2002) 83:2170-2179.
Clarke et al. "Continuous base identification for single-molecule nanopore DNA sequencing" NNano (2009) 4 (4):265-270.
Cockroft et al. "A single-molecule nanopore device detects DNA polymerase activity with single-nucleotide resolution" JACS (2008) 130(3):818-820.
Derrington et al. "Nanopore DNA sequencing with MspA" PNAS (2010) 107(37):16060-16065.
Geirhart et al., "Nanopore with Transverse Nanoelectrodes for Electrical Characterization and Sequencing of DNA," Sensors and Actuators B (2008) 132:593-600.
Gramlich et al. "Click-click-click: Single to triple modification of DNA" Angew Chem Int Ed (2008) 47:3442-3444.
Harrer et al. "Electrochemical characterization of thin film electrodes toward developing a DNA transistor" Langmuir (2010) 26(24):19191-19198.
He et al. "A hydrogen-bonded electron-tunneling circuit reads the base composition of unmodified DNA" Nanotech (2009) 20(7):075102.
Holden et al. "Direct introduction of single protein channels and pores into lipid bilayers" JACS (2005) 127 (18):6502-6503.
Hopfner et al. "Mechanisms of nucleic acid translocases: lessons from structural biology and single-molecule biophysics" Curr Opin Struct Biol (2007) 17(1):87-95.
Howorka et al. "Sequence-specific detection of individual DNA strands using engineered nanopores" Nature Biotech (2001) 19:636-639.
Hughes et al. "Optical absorption of DNA-carbon nanotube structures" Nano Lett (2007) 7(5):1191-1194.
Hurt et al. "Specific nucleotide binding an rebinding to individual DNA polymerase complexes captured on a nanopore" JACS (2009) 131(10):3772-3778.
Jiang et al. "The open pore conformation of potassium channels" Nature (2002) 47:523-526.
Kang et al. "A storable encapsulated bilayer chip containing a single protein nanopore" JACS (2007) 129:4701-4705.
Kim et al. "Rapid fabrication of uniformly sized nanopores and nanopore arrays for parallel DNA analysis" Adv Mat (2006) 18:3149-3153.
Li et al. "DNA molecules and configurations in a solidstate nanopore microscope" Nature Mat (2003) 2:611-615.
Liang et al. "Nanogap detector inside nanofluidic channel for fast real-time label-free DNA analysis" Nano Lett (2008) 8(5):1472-1476.
Lieberman et al. "Processive replication of single DNA molecules in a nanopore catalyzed by phi29 DNA polymerase" JACS (2010) 132(50):17961-17972.
Lindsay et al. "Recognition tunneling" Nanotech (2010) 21:262001.
Liu et al. "Descreening of field effect in electrically gated nanopores" Appl Phys Lett (2010) 97:143109.
Liu et al. "Translocation of single-stranded DNA through single-walled carbon nanotubes" Science (2010) 327:64-67.
Lohman et al. "Non-hexameric DNA helicases and translocases: mechanisms and regulation" Nature Rev Mol Cell Biol (2008) 9:391-401.
Lu et al. "Nanowire transistor performance limits and applications" IEEE Trans on Electron Dev (2008) 55 (11):2859-2876.
Luan et al. "Base-by-base ratcheting of single stranded DNA through a solid-state nanopore" Phys Rev Lett (2010) 104:8103-8106.
Meller et al. "Voltage-driven DNA translocation through a nanopore" Phys Rev Lett (2001) 86(15):3435-3438.
Merchant et al. "DNA Translocation Through Graphene Nanopores, " NanoLetters (2010) 10:2915-2921.
Pease et al. "Sequence-directed DNA translocation by purified FtsK" Science (2005) 307:586-590.
Polonsky et al. "Nanopore in metal-dielectric sandwich for DNA position control" Appl Phys Lett (2007) 91:153103-153103-3.
Reimhult et al. "Membrane biosensor platforms using nano- and microporous supports" Trends in Biotech (2007) 26 (2):82-89.
Schneider et al. "DNA translocation through graphene nanopores" Nano Lett (2010) 10:3163-3167.
Shchepinov et al. "Oligonucleotide dendrimers: synthesis and use as polylabelled DNA probes" Nucl Acids Res (1997) 25(22):4447-4454.
Singleton et al. "Structure and mechanism of helicases and nucleic acid translocases" Ann Rev Biochem (2007) 76:23-50.
Smeets et al. "Noise in solid-state nanopores" PNAS (2008) 105(2):417-421.
Stoddart et al. "Single-nucleotide discrimination in immobilized DNA oligonucleotides with a biological nanopore" PNAS (2009) 106:7702-7707.
Storm et al. "Fabrication of solid-state nanopores with single-nanometre precision" Nature Mat (2003) 2:537-540.
Tanaka et al. "Partial sequencing of a single DNA molecule with a scanning tunnelling microscope" Nature Nanotech (2009) 4:518-522.
Tian et al. "Three-dimensional, flexible nanoscale field-effect transistors as localized bioprobes" Science (2010) 329:830-834.
Tsutsui et al. "Identifying singl-e nucleotides by tunnelling current" Nature Nanotech (2010) 5:286-290.
Turner et al. "Confinement-induced entropic recoil of single DNA molecules in a nanofluidic structure" Phys Rev Lett (2002) 88(12):128103-1-4.
Wanunu et al. "Rapid electronic detection of probe-specific microRNAs using thin nanopore sensors" Nature Nanotech (2010) 5:807-814.
White et al. "Single ion-channel recordings using glass nanopore membranes" JACS (2007) 129(38):11766-11775.
Wu et al. "Protein nanopores with covalently attached molecular adapters" JACS (2007) 129:16142-16148.
International Search Report and Written Opinion dated Jan. 25, 2011 for related case PCT/US2010/001072.
International Preliminary Report on Patentability dated Oct. 20, 2011 for related case PCT/US2010/001072.
Kumar et al., "PEG-Labeled Nucleotides and Nanopore Detection for Single Molecule DNA Sequencing by Synthesis," Scientific Reports (2012) 2:684 DOI:10.1038-srep00684.

* cited by examiner

R = Charge Block Peptide

NANOPORE SEQUENCING USING CHARGE BLOCKADE LABELS

CROSS-REFERENCE TO RELATED APPLICATIONS

This application is a continuation application of U.S. patent application Ser. No. 13/083,320 filed Apr. 8, 2011, which claims priority to U.S. Provisional Patent Application 61/322,777, filed Apr. 9, 2010, U.S. Provisional Patent Application 61/391,500, filed Oct. 8, 2010, and U.S. Provisional Patent Application 61/415,213, filed Nov. 18, 2010. This application is related to U.S. Provisional Patent Application 61/168,431, filed Apr. 10, 2009; and U.S. patent application Ser. No. 12/757,789, filed Apr. 9, 2010, the full disclosures of which is incorporated herein by reference in its entirety.

STATEMENT REGARDING FEDERALLY SPONSORED RESEARCH

Not Applicable.

BACKGROUND OF THE INVENTION

The rapid determination of the nucleotide sequence of single- and double-stranded DNA and RNA is a major goal of researchers seeking to obtain the sequence for the entire genome of an organism. The ability to determine the sequence of nucleic acids in DNA or RNA has additional importance in identifying genetic mutations and polymorphisms. The concept of using nanometer-sized holes, or "nanopores," to characterize biological macromolecules and polymer molecules has recently been developed.

Nanopore-based analysis methods often involve passing a polymeric molecule, for example single-stranded DNA ("ssDNA"), through a nanoscopic opening while monitoring a signal such as an electrical signal. Typically, the nanopore is designed to have a size that allows the polymer to pass only in a sequential, single file order. As the polymer molecule passes through the nanopore, differences in the chemical and physical properties of the monomeric units that make up the polymer, for example, the nucleotides that compose the ssDNA, are translated into characteristic electrical signals.

The signal can, for example, be detected as a modulation of the ionic current by the passage of a DNA molecule through the nanopore, which current is created by an applied voltage across the nanopore-bearing membrane or film. Because of structural differences between different nucleotides, different types of nucleotides interrupt the current in different ways, with each different type of nucleotide within the ssDNA producing a type-specific modulation in the current as it passes through a nanopore, and thus allowing the sequence of the DNA to be determined.

Nanopores that have been used for sequencing DNA include protein nanopores held within lipid bilayer membranes, such as α-hemolysin nanopores, and solid state nanopores formed, for example, by ion beam sculpting of a solid state thin film. Devices using nanopores to sequence DNA and RNA molecules have generally not been capable of reading sequence at a single-nucleotide resolution.

While this prior work has shown the promise of nanopores for detecting some sequence information, there is a need for accurate, reliable devices and methods for measuring sequences such as those of RNA and DNA. Accordingly, there is a need for a method of fabricating arrays of nanopores in a form that is amenable to manufacturing and can provide accurate and reliable measures of nanopore current. Similarly, there is a related need for devices capable of sequencing molecules having nanoscale dimensions at a high speed and at a high level of resolution.

SUMMARY OF THE INVENTION

In some aspects the invention provides a device for determining the identity of a single molecule passing through a nanopore comprising: three fluidic regions comprising i) a sample fluidic region, ii) a measurement fluidic region, and iii) a reference fluidic region; a substrate comprising a measurement electrode positioned to sense the potential of the measurement fluidic region; a first aperture comprising a nanopore through which one or more sample molecules are transported, the first aperture connecting the sample fluidic region and the measurement fluidic region; a second aperture connecting the measurement fluidic region with the reference fluidic region, whereby the first aperture and second aperture comprise substantially the only fluidic contact between the three fluidic regions; and a pair of drive electrodes, whereby a potential drop across the drive electrodes drives a sample molecule into the nanopore from the sample fluidic region, and whereby the presence of a sample molecule within the nanopore is detected using potential measurements made by the measurement electrode.

In some embodiments the device further comprises a sample electrode positioned to sense the potential of the sample fluidic region and a reference electrode positioned to sense the potential of the reference fluidic region, wherein the presence of the sample molecule in the nanopore is detected using the potential measurements at the sample electrode, the measurement electrode, and the reference electrode.

In some embodiments the first electrode comprises the gate of a first transistor element positioned to sense the potential of the sample fluidic region, the second electrode comprises the gate of a second transistor element positioned to sense the potential of the measurement fluidic region, and the third electrode comprises the gate of a third transistor element positioned to sense the potential of the reference fluidic region. In some embodiments one or more of the first, second, or third transistors is a naked gate transistor having no metal electrode. In some embodiments the gate of the naked gate transistor has a thin insulating film between the gate and the reservoir. In some embodiments the gate of the transistor has a thin layer of metal contacting a thin insulating layer contacting the channel of the transistor In some embodiments the sample molecule comprises a single stranded nucleic acid molecule. In some embodiments the sample molecule comprises a nucleotide analog having a charge blockade label.

In some embodiments a sample potential V1, a measurement potential V2, and a reference potential V3 are measured, and whereby the presence of a sample molecule within the nanopore is detected using the value of $(V1-V2)/(V2-V3)$.

In some embodiments the device is fabricated in a semiconductor substrate by etching a well into the substrate, forming a semiconductor lid over the well to form a chamber, fabricating transistors onto the substrate, and etching holes through the lid into the chamber for sample and reference nanopores. In some embodiments the substrate comprises silicon, silicon on insulator (SOI), or silicon on sapphire. In some embodiments the device comprises a vertical IGFET.

In some embodiments the vertical IGFET is produced by forming an N-doped well in a P-doped substrate, filling the N-doped well with P-doped semiconductor, forming a hole that extends through the P-doped semiconductor, the N-doped well, and the P-doped substrate, and fabricating electrodes onto the top surface of P-doped semiconductor and the P-doped substrate such that these become the source and drain of the IGFET. In some embodiments the transistors are formed on the top of a semiconductor substrate, and a fluidic structure is produced on top of the semiconductor substrate, the fluidic structure establishing sample, measurement and reference fluidic regions having a sample nanopore between the sample and measurement fluidic regions, and a reference nanopore between the measurement and reference regions.

In some aspects the invention provides an analytical device comprising a plurality of devices described above sharing a common substrate. In some embodiments the analytical device comprises 1,000 to 100,000 devices or from 10,000 to 1 million devices.

In some aspects the invention provides a device for determining the identity of a single molecule passing through a nanopore comprising: four fluidic regions comprising i) a sample fluidic region, ii) a first measurement fluidic region, iii) a second measurement fluidic region, and iv) a reference fluidic region; a substrate comprising one or two first electrodes positioned to sense the potential of the sample fluidic region, a second electrode positioned to sense the potential of the first measurement fluidic region, a third electrode to sense the potential of the second measurement fluidic region, and a fourth electrode positioned to sense the potential of the reference fluidic region; a first aperture comprising a nanopore through which one or more sample molecules are transported, the first aperture connecting the sample fluidic region and the first measurement fluidic region; a second aperture comprising a nanopore through which one or more sample molecules can be transported, the second aperture connecting the sample fluidic region and the second measurement fluidic region; a third aperture connecting the first measurement fluidic region with the reference fluidic region, a fourth aperture connecting the second measurement fluidic region with the reference fluidic region; and a pair of drive electrodes, one drive electrode in contact with the sample fluidic region and one drive electrode in contact with the reference fluidic region, whereby a potential drop across the drive electrodes drives a sample molecule into the first nanopore from the sample fluidic region to the first measurement fluidic region, and optionally into the second nanopore from the sample fluidic region to the second measurement fluidic region; whereby the presence of a sample molecule within either the first or second nanopore is detected using potential measurements made by the first, second, third, and fourth electrodes.

In some embodiments the first electrode comprises the gate of a first transistor element positioned to sense the potential of the sample fluidic region, the second electrode comprises the gate of a second transistor element positioned to sense the potential of the first measurement fluidic region, the third electrode comprises the gate of a third transistor element positioned to sense the potential of the second measurement fluidic region, and the fourth electrode comprises the gate of a fourth transistor element positioned to sense the potential of the reference fluidic region.

In some aspects the invention provides a method for determining sequence information about at template nucleic acid molecule comprising providing a substrate having at least one nanopore extending therethrough, having an opening on the top and on the bottom of the substrate, and having a single polymerase enzyme attached proximal to the to opening of the at least one nanopore, the polymerase enzyme complexed with a primed template nucleic acid; contacting the substrate with a sequencing reaction mixture comprising reagents required for polymerase mediated nucleic acid synthesis including one or more nucleotide analogs, each comprising a current blockade label, providing a voltage drop across the nanopore such that when the base portion of the nucleotide analog is complexed with an attached polymerase enzyme, the current blockage label enters the nanopore, resulting in a measurable change in current through the nanopore; measuring the current through the nanopore over time to detect the incorporation of nucleotides into a growing strand; and identifying the type of nucleotide incorporated into the growing strand, thus determining sequencing information about the template nucleic acid molecule.

In some embodiments the sequencing reaction mixture comprises two or more nucleotide analogs, each having a different current blockade label, each having different current blockage characteristics whereby the labels are distinguishable in measurements of the current through the nanopore over time. In some embodiments the sequencing reaction mixture comprises four different nucleotide analogs, each corresponding to the bases A, G, C, and T, or A, C, G, and U. Non-canonical bases can also be used in this method, including methylated or hydroxymethylated bases as well as nucleotide analogs such as 2-aminopurine (2-AP), 3-MI, 6-MI, 6-MAP, 5-hmC, 5mC, 4mC, N-6-methyladenosine, pyrrolo-dC, derivatives of pyrrolo-dC, furan-modified bases, 1,3-Diaza-2-oxophenothiazine, tCO., 1,3-diaza-2-oxophenoxazine, methyl-7-guanosine, inosine, thiouridine, pseudouridine, dihydrouridine, queuosine, wyosine, aminoallyl versions of A, C, G and T, diaminopurine, diaminopyrimidine, isoguanine, isocytosine, diaminopyrimidine, xanthine, 2-aminoadenine, 2,4-difluorotoluene, 4-methylbenzimidazole, isoquinoline, pyrrolo[2,3-b]pyridine, 2-amino-6-(2-thienyl)purine, pyrrole-2-carbaldehyde, 2,6-bis(ethylthiomethyl)pyridine (SPy) with a silver ion, pyridine-2,6-dicarboxamide, 2'-deoxyinosine (hypoxanthine deoxynucleotide) derivatives, nitroazole analogues, and hydrophobic aromatic non-hydrogen-bonding bases, as well as xDNA versions of all of these. There are numerous other nucleotide analogs and non-canonical bases that can serve in this role that have already been defined in the art, as well as a large number of novel modifications that can be devised by making modifications to the canonical bases or the non-canonical bases that have already been devised. In some embodiments the current blockage characteristics comprise the magnitude of the current through the nanopore. In some embodiments the current blockage characteristics comprise the shape of the measured current through the nanopore over time. In some embodiments the nucleotide analogs have the structure NS-PP-L-B wherein NS comprise a nucleoside moiety, PP comprises a polyphosphate chain with at least two phosphates, L comprises a linker, and B comprises a charge blockade label. The invention will in general use nucleotide analogs each having a different blockade label, however, in some implementations, native nucleotides can be used.

In some embodiments different current blockade labels have a different level of net charge. In some embodiments different current blockade labels have a difference in length. In some embodiments the current blockade labels comprise polymers of charged monomer units, and different current blockade labels have different numbers of monomer units. In some embodiments different nucleotide analogs comprise linkers having different lengths.

In some embodiments the current blockade label on the at least one nucleotide analog is attached to the polyphosphate of the nucleotide analog such that when the nucleotide analog is incorporated, the current blockage label is released.

In some embodiments the nanopore comprises a solid state nanopore. In some embodiments the nanopore comprises a nanopore protein. In some embodiments the nanopore comprises a hybrid nanopore comprising a solid state pore dimensioned and treated so as to accept a single nanopore protein.

In some embodiments the polymerase is attached directly to the substrate. In some embodiments the polymerase is attached via a biotin group. In some embodiments the polymerase enzyme comprises a fusion protein between a polymerase enzyme and a nanopore protein.

In some embodiments the voltage drop across the nanopore is positive on the top side of the nanopore relative to the bottom side of the nanopore, such that positively charged molecules tend to be transported through the nanopore. In some embodiments charge blockade labels have a net negative charge.

In some embodiments the duration of a peak in the measurement of current through the nanopore is used to distinguish an incorporation event from background.

In some embodiments the nanopore has a non-cylindrical shape. In some embodiments the nanopore has a truncated cone shape. When referring to the shape of the nanopore, the shape generally refers to the interior shape of the pore.

In some aspects the invention provides a composition comprising: a polymerase enzyme attached to a substrate proximal to a nanopore, and nucleic acid sequencing reagents including at least one nucleotide analog, the nucleotide analog having the structure NS-PP-L-B wherein NS comprise a nucleoside moiety, PP comprises a polyphosphate chain with at least two phosphates, L comprises a linker, and B comprises a charge blockade label.

In some embodiments the blockade label has a net positive charge. In some embodiments the blockade label comprises a polymer of positively charged monomer units. In some embodiments the blockade label comprises a protein. In some embodiments the blockade label comprises lysine, arginine, or ornithine.

In some embodiments the linker group comprises polyethylene glycol or a branched or linear alkane. In some embodiments the polyphosphate chain comprises 3, 4, 5, 6, 7, or 8 phosphates.

In some embodiments the sequencing reaction mixture comprises two or more nucleotide analogs, each having a different current blockade label. In some embodiments different current blockade labels have a different level of net charge. In some embodiments different current blockade labels have a difference in length. In some embodiments the current blockade labels comprise polymers of charged monomer units, and different current blockade labels have different numbers of monomer units. In some embodiments different nucleotide analogs comprise linkers having different lengths. In some embodiments the nucleic acid sequencing reagents comprises four different nucleotide analogs, each corresponding to the bases A, G, C, and T, or A, C, G, and U. In some cases, the different blockade labels in a set will have different elastic modulus properties. The difference in "stretchiness" of a linker attached to blockade label can have an effect on how the blockade label resides within the pore, allowing for distinguishing between nucleotide analogs. The elastic modulus can also affect the dynamic properties of the blockade label, allowing a given label to be identified by observing the current versus time during the blockage.

In some aspects the invention provides a system for nucleic acid sequencing comprising: a substrate having at least one nanopore extending therethrough, having an opening on the top and on the bottom of the substrate, and having a single polymerase enzyme attached proximal to the to opening of the at least one nanopore, the polymerase enzyme complexed with a primed template nucleic acid; a sequencing reaction mixture in contact with the substrate comprising reagents required for polymerase mediated nucleic acid synthesis including one or more nucleotide analogs, each comprising a current blockade label; drive electrodes in contact with the reaction mixture on either side of the substrate for producing a voltage drop across the at least one nanopore; one or more measurement electrodes connected to electronic measurement equipment for measuring the current through the nanopore over time; and a computer for identifying the type of nucleotide incorporated into the growing strand.

In some aspects the invention provides a device for analysis of single molecules in nanopores comprising: a substrate comprising a plurality of nanopores, each nanopore disposed within a chamber; each chamber comprising drive electrodes for driving single molecules from the sample through the nanopores, and each chamber comprising electrodes capable of measuring current through the nanopore; wherein the device is configured such that the plurality of nanopores are simultaneously accessible to a fluidic sample for loading the sample, and wherein the device is configured such that the nanopores are each fluidically isolated from one another during analysis.

In some embodiments the device comprises a top gasket above the substrate and a bottom gasket below the substrate, the top and bottom gaskets configured such that each gasket is spaced away from the substrate while the sample is loaded, and configured such that each gasket is held against the substrate during analysis to isolate the nanopores from one another.

In some aspects, the invention provides a method for analyzing single molecules in nanopores comprising: providing a device having a loading configuration and an analysis configuration, the device having a substrate comprising a plurality of nanopores, each nanopore disposed within a chamber; wherein each chamber comprises drive electrodes for driving single molecules from the sample through the plurality of nanopores, and each chamber comprises electrodes for measuring current through the nanopore; loading a fluidic sample onto the substrate when the device is in the loading configuration whereby the plurality of nanopores are simultaneously accessible to the fluidic sample; and analyzing the sample when the device is in the analysis configuration by fluidically isolating each of the plurality of nanopores from one another; providing drive voltages across each of the fluidically isolated nanopores with the drive electrodes; and measuring the current through the nanopores to characterize the single molecules in the fluidic sample.

In some embodiments the device comprises a top gasket above the substrate and a bottom gasket below the substrate, spacing the top and bottom gaskets away from the substrate in the loading configuration, and mating with the substrate while the device is in the analysis configuration to isolate the chambers comprising the nanopores from one another.

DESCRIPTION OF THE FIGURES

FIG. 15(A) provides a structure having a nucleoside connected to a polyphosphate chain. FIG. 15(B) shows an exemplary nucleotide analog in which the nucleotide analog comprises the nucleoside deoxythimidine having the base thimine (T). FIG. 15(C) shows a nucleotide analog which has a deoxynucleoside unit which has a base that can be incorporated into the nascent strand by a polymerase enzyme.

FIG. 16(A) shows a blockade label comprising a linear polymer having 7 lysine monomers. FIG. 16(B) shows how branching can be used to produce a branched blockade label from lysine monomers. FIG. 16(C) provides a linear structure having more bulk per charge.

In FIG. 20A, the device is in the open position and the fluidics are active. In FIG. 20B, the top and bottom gaskets are brought into contact with top and bottom of the fluidic chambers resulting in a seal which fluidically isolates each of the chambers.

FIG. 22(B) shows a set of monomers that can be used for sequential click addition for adding resistance labels.

DETAILED DESCRIPTION OF THE INVENTION

I. General

Figure 1:
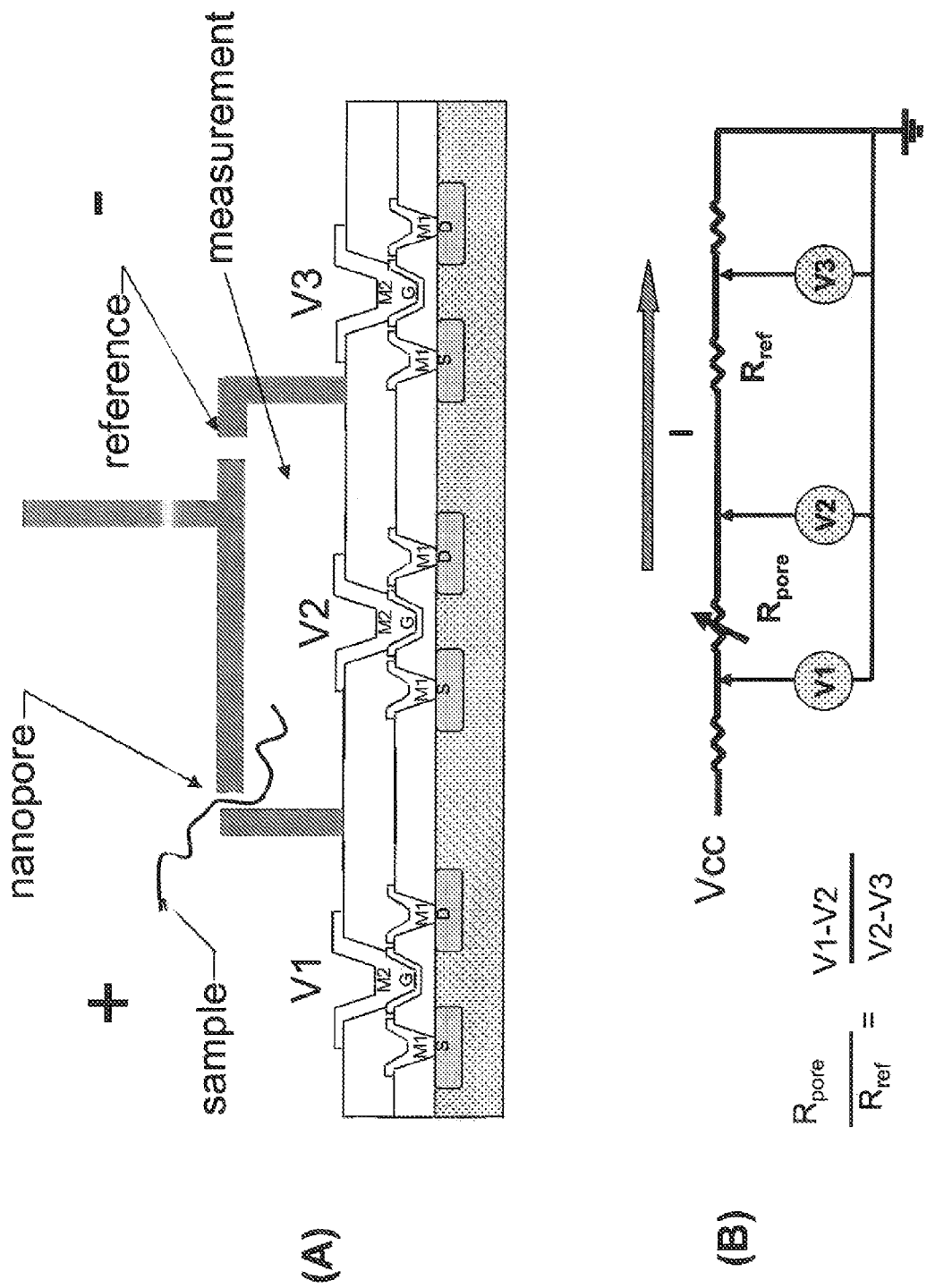
FIG. 1(A) shows an embodiment of the device of the invention for measuring current through a nanopore.
FIG. 1(B) shows an equivalent circuit diagram for an electrolyte circuit of the invention for measuring nanopore current.

In some aspects, the invention relates to devices, systems, and methods for sequencing polymers using nanopores. In particular, the invention relates to multiplex sequencing in which sequencing data is simultaneously obtained from multiple nanopores. In some aspects, the invention relates to multiplex nanopore sequencing devices that directly incorporate semiconductor devices, such as CMOS devices. The devices of the invention can be made wherein the nanopores are formed in a semiconductor substrate, such as silicon. Alternatively, the devices can be made in a composite semiconductor substrate such as silicon-insulator-silicon (SOI), or can be made by bonding together semiconductor and insulator components.

The incorporation of semiconductors such as silicon into the devices provides for the inclusion of electronic circuitry in close association with the nanopores. For example, the use of silicon allows for a multiplex device having an array of electronic circuits wherein each nanopore in the array is directly associated with a set of electronic circuits. These circuits can provide the functions of measurement, data manipulation, data storage, and data transfer. The circuits can provide amplification, analog to digital conversion, signal processing, memory, and data output. By having components such as CMOS processors included in the device addresses the issue of monitoring multiple events simultaneously. Rather than having at least one pair of wires bringing signals out from the chip, the inclusion of these components allows for providing a multiplexed output or an addressable output as in a DRAM chip.

The nanopore sequencing of the invention relates generally to the sequencing of polymers. The polymers to be sequenced can be, for example, nucleic acids such as RNA or DNA, proteins, polypeptides, polysaccharides, or other polymers for which information about the sequence is of value. In some embodiments, the sequencing is performed by measuring the modulation of current as the polymer molecule, e.g. a single-stranded DNA molecule passes through the nanopore. In some cases, the polymer as a whole does not pass through the pore, but portions of the polymer, or molecules associated with portions of the polymer pass through the nanopore, and are detected. For example, in some cases, a nucleic acid is sequentially degraded, sequentially releasing monomeric units, e.g. by an exonuclease, and the monomeric units are detected as they pass through the nanopore. Certain aspects and embodiments are described as being implemented with specific materials, e.g. a specific polymer. It understood that the embodiments described can be implemented using any suitable material such as those described elsewhere herein or as known in the art.

The invention also provides methods of nanopore sequencing using nucleotide analogs having current blockade labels. A polymerase enzyme that is attached proximal to a nanopore can bind the nucleotide analogs during nucleic acid synthesis. While the nucleotide analogs are within the active site during incorporation, the current blockade label is held within the pore, blocking current flow through the pore at least partially. This current blockage provides a means of detecting when the nucleotide is associated with the polymerase enzyme, which can be used to determine when the nucleotide is incorporated. By using a plurality of nucleotide analogs, each having a current blockade label with different current blockage characteristics, the identity of the nucleotide analog that is incorporated can also be determined, providing sequence information about the template nucleic acid associated with the polymerase. These methods allow for obtaining sequencing data in real time while the polymerase is catalyzing template dependent nucleic acid synthesis.

The types of nanopores that can be used in the invention include biological nanopores, solid state nanopores, and hybrid nanopores. Any suitable nanopore can be employed including solid state nanopores with electrical gating and with horizontal tunnel junctions. See e.g. Liu et al. Applied Physics Letters, 97, 143109, 2010, which is incorporated by reference herein in its entirety for all purposes.

Ratiometric Impedance Method for Nanopore Detection

One aspect of the invention is a device for determining the identity of a single molecule passing through a nanopore comprising: three fluidic regions comprising i) a sample fluidic region, ii) a measurement fluidic region, and iii) a reference fluidic region; a substrate comprising a measurement electrode positioned to sense the potential of the measurement fluidic region; a first aperture comprising a nanopore through which one or more sample molecules are transported, the first aperture connecting the sample fluidic region and the measurement fluidic region; a second aperture connecting the measurement fluidic region with the reference fluidic region, whereby the first aperture and second aperture comprise substantially the only fluidic contact between the three fluidic regions; and a pair of drive electrodes, one drive electrode in contact with the sample fluidic region and one drive electrode in contact with the reference fluidic region, whereby a potential drop across the drive electrodes drives a sample molecule into the nanopore from the sample fluidic region to the measurement fluidic region, and whereby the presence of a sample molecule in the nanopore is detected using potential measurements made by the measurement electrode. In some embodiments, in addition to the measurement electrode, the device also has a sample electrode positioned to sense the potential of the sample fluidic region and a reference electrode positioned to sense the potential of the reference fluidic region and the presence of a sample molecule in the nanopore is detected using potential measurements made by the sample, measurement, and reference electrodes. In preferred aspects, the first, second, and third electrodes comprise the gates of a first, second, and third transistor respectively.

The invention has aspects comprising devices and methods for arrays comprising electronic circuits and MEMS structures to measure changes in the impedance of an electrolyte circuit having elements with a nanopore diameter, the opening of which is modulated by a sample molecule passing through it. This circuit can be manufactured using commercial foundry processes in many technologies including CMOS, BJT and Bi-CMOS.

FIG. 1(A) shows one embodiment of the device of the invention. The electrolyte circuit consists of a sample reservoir to the left and a reference reservoir to the right separated by a chamber (measurement reservoir) containing an entrance port to the sample reservoir and an exit port to the reference reservoir. There are drive electrodes represented by the (+) and (−) in the sample and reference reservoirs. While here the drive electrodes have positive voltage on the sample side relative to the reference side, in some cases the drive voltage will have a negative voltage on the sample side relative to the reference side. In general, a positive voltage in the sample reservoir will result in the transport of net positive ions through the pore, while a negative voltage in the sample reservoir will result in the transport of net negative ions. The type of ion which is being transported will typically dictate the potential that is used. In some cases, the potential can vary with time, comprising an AC system or an AC system with a DC bias. The drive electrodes are used to create the potential that drives the sample molecule through the nanopore.

The sizes of these ports can be any suitable size. In some cases the entrance port is matched with exit port in size. By having the two ports of approximately the same size, the ports generally will have a similar level of resistivity or impedance (in the absence of a partially blocking sample molecule). Having a similar resistance or impedance in the entrance and exit port tends to reduce the complexity of the measurement. One of the ports (usually the exit port) is used as a reference aperture while the other (usually the entrance port) is used as the sample port where the variable size of the polymer chain elements modulates the aperture diameter of the nanopore. A measurement in the measurement reservoir can be used for a common measurement of the stable bias to provide the mid point voltage. In some cases it is desirable to have the resistance of the reference aperture be about the same as the resistance of the measurement aperture when there is a blockade within the pore. A reference port of this manner can be constructed by using the same type of pore for the measurement and reference pore, and include a constant blockage in the reference pore, for example using compounds similar to the blockade labels on the nucleotide analogs, but permanently attached either to the pore or proximate to the pore. Where there are a plurality of blockade labels used, each having a different level of blockage, sometimes the reference pore is set to have an impedance about the same as the blockade with the highest impedance, in some cases it is set to about the middle of the impedance of the blockade labels with the highest and lowest impedance.

For the device shown in FIG. 1(A), the potential measurements in the sample, measurement, and reference fluidic regions are determined by transistors on a single substrate. In other cases, the substrate can have electrodes that contact the sample, measurement, and reference regions, which electrodes are connected to potential measurement elements on other parts of the substrate, or outside of the substrate. Here, each of the transistors is built into a substrate, each transistor having a source (S) and drain (D) each in contact with a metal electrode (M1). Between the source and drain electrodes is the gate (G). The gate G may have a conductive electrode, typically a metal (M2) as shown in FIG. 1(A), the gate may have only a thin insulating film between it and the fluid in the reservoir, or the gate can be in direct contact with the fluid. The transistor will measure the potential (V) in the fluidic reservoir with which it is in contact. There will generally be a thin insulating layer between the gate and the conducting channel between the source and the drain. In some cases this insulating layer is deposited or grown, in other cases, it comprises an oxide that forms on the silicon surface due to exposure to the air.

The measurement of impedance of the sample port is made via a ratio of the potential difference across the reference and sample ports. FIG. 1(B) shows an equivalent circuit diagram which can be simplified if a single current path exists as:

$$V_{cc} - I(2R_{res} + R_{pore} + R_{ref}) = 0$$

$$\frac{R_{pore}}{R_{ref}} = \frac{V_1 - V_2}{V_2 - V_3}$$

The measurement of voltage in the electrolyte circuit is generally performed by an insulated gate transistor as shown in FIG. 1(A). A surface of the transistor such as a conducting plate samples the potential in the fluid and this potential is insulated from the substrate with a very thin insulating layer between source and drain electrodes. In some embodiments, there is no metal conductor associated with the gate, and a thin film is in direct contact with the electrolyte solution, sensing its potential. We refer to these transistors as naked gate transistors. The potential induces a field across the insulator and into the substrate. By placing source and drain electrodes across a narrow channel perpendicular to the induced field, a modulation in the resistance of this channel can be made proportional to the induced field. Many devices have been designed and are in widespread use that takes advantage of this effect including MOS, JFET, IGFET devices. The use of insulating gate devices provides voltage amplification and sampling of the fluid potential with no conductive path between the fluid layer and the semiconductor.

In some embodiments of the invention, the connection of the fluidic reservoir to the gate is made directly through the thin oxide layer or other layer over what would represent the gate region of the transistor. This direct fluidic connection enables the modulation of the transistor channel and depletion layer to be in proportion to the fluidic potential. In another embodiment, the depletion region and channel are modulated by the connection of the fluid potential through a gate conductive layer above the oxide. This layer can be comprised of a metallic element or a conductive semiconductor layer (i.e. polysilicon).

The invention relates in some aspects to devices for multiplex nanopore sequencing. In some cases, the devices of the invention comprise resistive openings between fluid regions in contact with the nanopore and fluid regions which house a drive electrode. The devices of the invention can be made using a semiconductor substrate such as silicon to allow for incorporated electronic circuitry to be located near each of the nanopores or nanometer scale apertures in the array of nanopores which comprise the multiplex sequencing device. The devices of the invention will therefore comprise arrays of both microfluidic and electronic elements. In some cases, the semiconductor which has the electronic elements also includes microfluidic elements that contain the nanopores. In some cases, the semiconductor having the electronic elements is bonded to another layer which has incorporated microfluidic elements that contain the nanopores.

The devices of the invention generally comprise a microfluidic element into which a nanopore is disposed. This microfluidic element will generally provide for fluid regions on either side of the nanopore through which the molecules to be detected for sequence determination will pass. In some cases, the fluid regions on either side of the nanopore are referred to as the cis and trans regions, where the molecule to be measured generally travels from the cis region to the trans region through the nanopore. For the purposes of description, we sometimes use the terms upper and lower to describe such reservoirs and other fluid regions. It is to be understood that the terms upper and lower are used as relative rather than absolute terms, and in some cases, the upper and lower regions may be in the same plane of the device. The upper and lower fluidic regions are electrically connected either by direct contact, or by fluidic (ionic) contact with drive and measurement electrodes. In some cases, the upper and lower fluid regions extend through a substrate, in other cases, the upper and lower fluid regions are disposed within a layer, for example, where both the upper and lower fluidic regions open to the same surface of a substrate. Methods for semiconductor and microfluidic fabrication described herein and as known in the art can be employed to fabricate the devices of the invention.

The invention involves the use of an electrode to sense potential in a fluidic region. The electrode may be made of any suitable material. The electrode generally comprises a conductor or a semiconductor. For example, the electrode can be a metal, a semiconductive metal oxide, or a semiconductor such as silicon or gallium arsenide. In some cases the electrode is coated with a thin insulating layer that allows for the electrode to sense the potential without being directly exposed to the fluid. The insulating layer can comprise an inorganic or organic material. The insulating layer can be deposited, plated, or grown onto the electrode surface, for example by chemical vapor deposition. In some cases the electrode that senses the potential comprises a component in an electrical circuit. For example, the electrode can comprise the gate of a transistor including the gate of a naked transistor. The electrode is generally connected to or is part of an electronic component that is used to measure the potential. In some cases the component is a transistor or series of transistors. The electronic component can also comprise a capacitor or other suitable component. In some cases the electrode comprises a conductor (e.g. a wire) that is in contact with the solution (with or without an insulating layer), which extends from the fluid to an electronic component for measuring potential. This electronic component can be in the substrate that is in contact with the fluid, or the conductor can extend to an electronic component off of the substrate. In preferred embodiments, the electrode is in direct contact with or comprises a portion of an electrical component on the substrate. Such electrical component can be, for example, a transistor.

Top Side Monolithic Chamber

Figure 2:
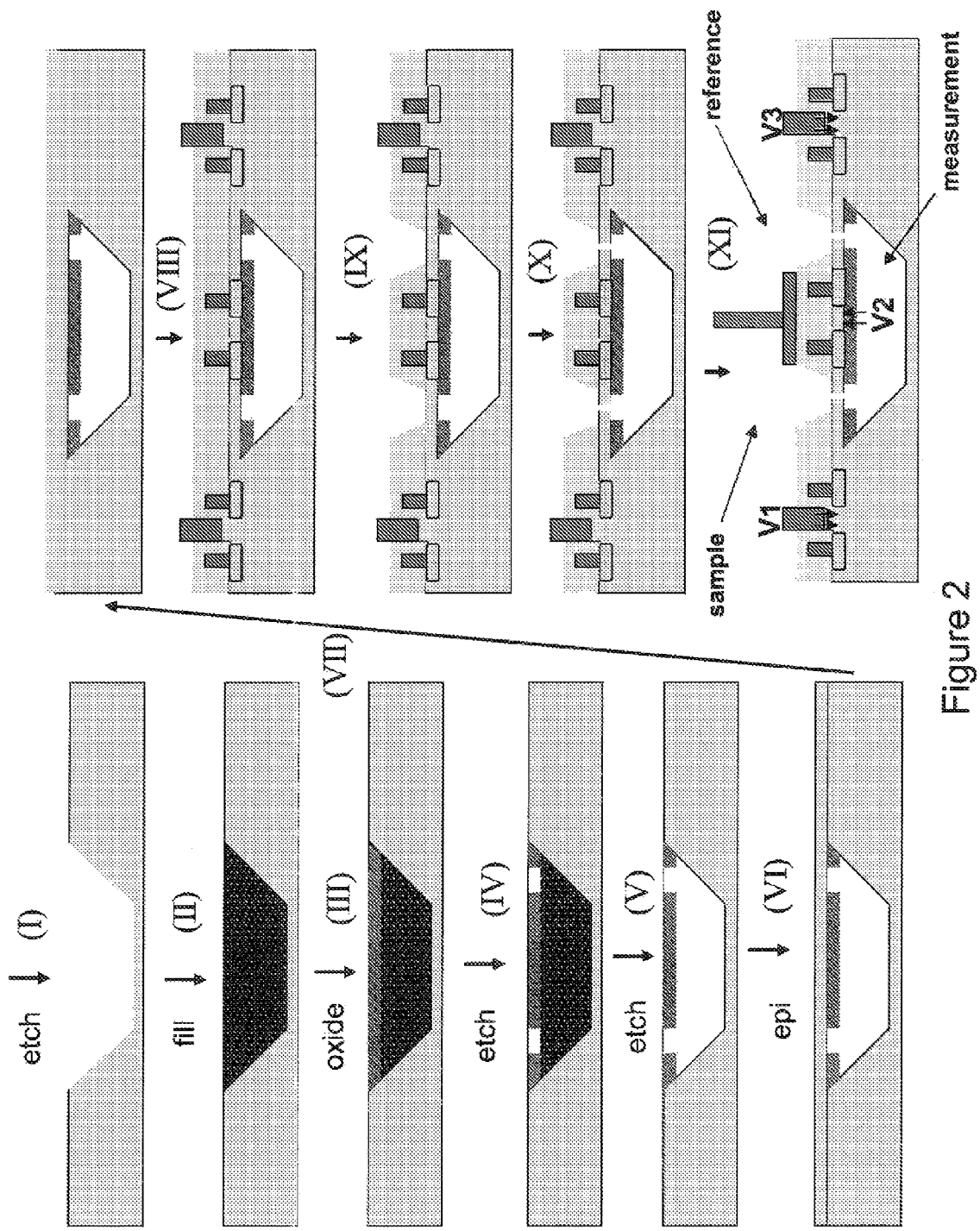
FIG. 2 is a schematic diagram of a process for fabrication of a device of the invention.

The design of the chamber and ports has a number of embodiments. In some cases, the monolithic fabrication of chambers is accomplished by removing material from the substrate and growing a lid over the voided area. A process to fabricate these types of devices is detailed in FIG. 2. In this Figure, a semiconductor wafer is etched to create a vertical cavity or well in step (I). This cavity is filled with a material in step (II) that can be specifically etched while leaving the resulting substrate intact at a later step. In step (III) high quality insulating layer, such as an oxide, is placed above this filler material and will be used as the gate insulator for the device which measures potential in the central chamber (measurement reservoir). Holes are etched in this layer in step (IV), then etching is performed in step (V) to remove the filler layer below. This process results in a cavity with a thin insulating layer above it. An epitaxial layer of the semiconductor is then grown over this structure in step (VI) with the substrate providing the seed crystal pattern. From this layer, a standard transistor and circuit process flow can be followed to create the three measuring devices with insulating gates as shown in steps (VII) and (VIII).

The chamber is then integrated into the fluidic circuit by etching entrance and exit ports in steps (IX) and (X) through the semiconductor and insulator layers, which will serve as the sequencing nanopore aperture and the reference resistive opening. The separation of high potential and low potential reservoirs (e.g. ground potential) is made via polymer partitions patterned above the IC surface as shown in step (XI). This produces a substrate with three types of transistors, one in the sample region to measure V1, one in the measurement region to measure V2, and one in the reference region to measure V3. This architecture provides for the inclusion of nanopores on the etched ports as a final step as these ports are exposed at the top surface. In the case that the polymer partitions are fabricated separately and applied at the time of use, as in PDMS fluidics structure and other bonded-layer fluidic manifolds known in the art, the aperture that will sustain the sequencing nanopore is directly available immediately prior to sequencing, enabling the use of the widest possible array of methods to incorporate any biological or other exogenous nanopore structure just prior to use. The nanopores used for the entrance and/or exit ports can be for example, solid state nanopores, protein nanopores, or hybrid nanopores such as those described in the related applications. In some cases, the nanopores can be graphene nanopores or graphene nanogaps. Graphene provides a useful substrate for the formation of nanopores in that it is a strong single-atom layer.

The novel circuit architecture results from this process. The left and right measurement devices use the field from the top surface of the device to modulate the signal current. The middle transistor will use the field induced from the chamber fluid below it for signal modulation. These transistors are typically fabricated with an identical process (i.e. NMOS) in a coplanar arrangement but their signal sources are generated on two different vertical planes.

Figure 3:
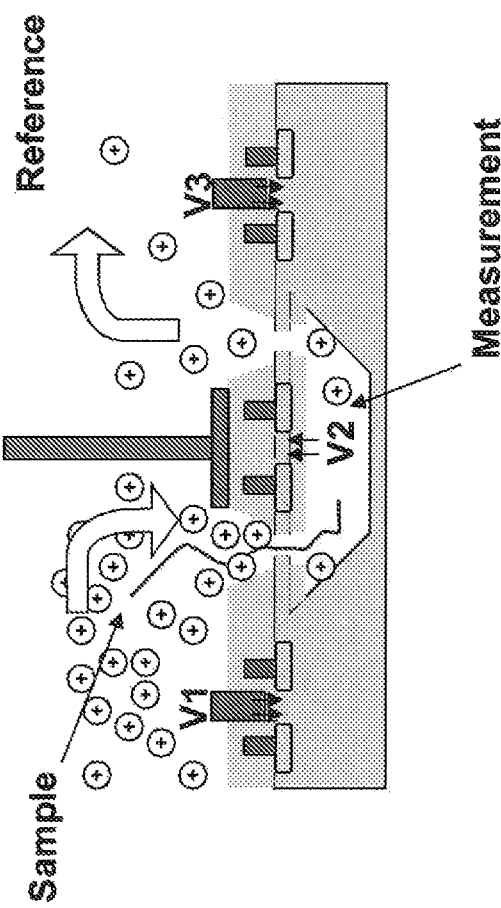
FIG. 3 is an illustration of the operation of a device fabricated as described in FIG. 2.

The operation of this device is illustrated in FIG. 3. Drive electrodes (not shown) produce a potential between the sample and reference reservoirs, resulting in a sample molecule traversing the entrance port and partially impeding the transfer of charged fluidic particles into the measurement chamber. This modulation of flow varies the potential in the chamber and satisfies the conditions for measurement shown in FIG. 1(B), allowing for the precise measurement of the current flow through the nanopore. The sample molecules can be any suitable molecule that can be measured by being held in or being transported through the nanopore. In some cases the sample molecules are molecules that are derived from the nucleic acid synthesis or degradation, for example nucleotides having blockade labels observed during nucleic acid synthesis, or nucleotides removed sequentially from a nucleic acid, for example by an exonuclease. In some cases, the sample molecules comprise single stranded nucleic acids either with or without resistance labels associated with the bases on the nucleic acid.

In some cases it is useful to decouple the potential of the reference and the sample regions from the potentials of the used to read the output of the transistors. For example, in some cases, the ground potential for the transistor is set neither at the potential of the sample reservoir nor the potential of the reference reservoir. By controlling this potential, the transistors can be operated in their optimal region of sensitivity.

While the invention is described as having five electrodes: two drive electrodes, a sample region electrode, a measurement region electrode, and a reference region electrode, the devices of the invention also include embodiments where three electrodes are used. In these cases one drive electrode is in electrical contact with the sample region, the other drive electrode is in contact with the reference region, and the third electrode is the sensing electrode which is in the measurement region. The sensing electrode may be part of a sensing transistor. The three electrode configuration can be used in the same manner described herein for the five electrode configuration, using the same sample and reference pores etc. The five electrode configuration has some advantages in sensitivity and stability. The three electrode configuration has advantages in terms of simplicity and cost.

Back Side Monolithic Chamber Using Silicon on Insulator (SOI)

Figure 4:
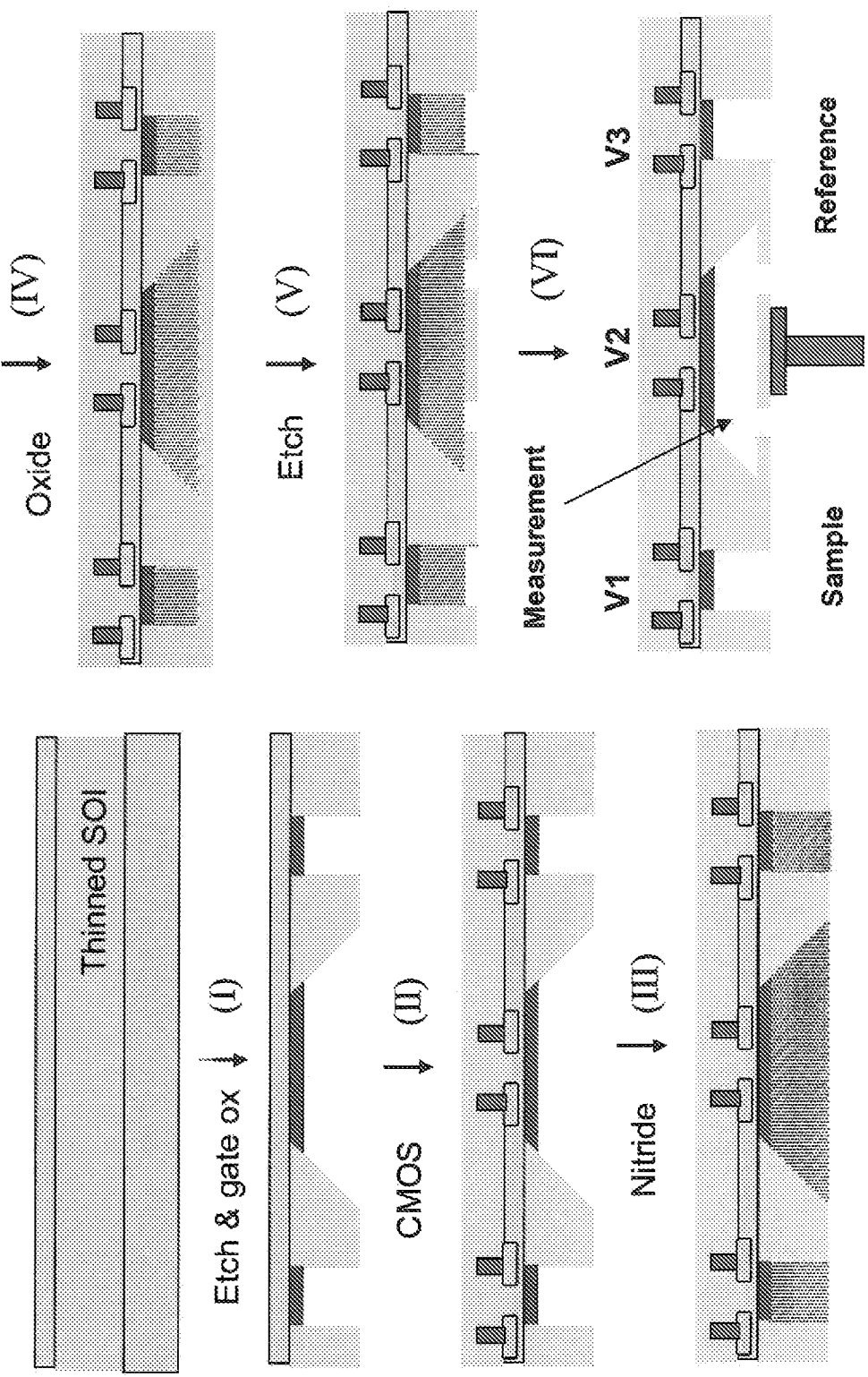
FIG. 4 is schematic diagram of an alternative process for fabricating a device of the invention using an SOI substrate.

An alternative embodiment of monolithic assembly is shown in FIG. 4. In this process, a thin silicon on insulator wafer is used. A thinning process can be used to produce a wafer having the appropriate dimensions. In step (I), the lower silicon layer is removed and a cavity for each of the three transistors is etched in the back surface with the silicon as the etch stop. The middle cavity will contain the entrance and exit ports while the left and right transistors will sample the two reservoir potentials. Also in step (I), a field oxide is grown in these cavities. CMOS devices are then fabricated on the top surface of the wafer and the gate regions aligned with the field oxide areas in step (II). The back surface of the wafer is then processed in step (III) to complete the chamber by filling the cavities with nitride. An oxide is then deposited over the nitride layer in step (IV). In step (V) the entrance and exit ports to the center cavity are made. In step (VI) the nitride layer is then removed from the cavity and the left and right reservoir cavities, and a barrier is constructed to separate the sample and reference reservoirs. One example method of selective anisotropic etching to remove the nitride is with a fluorocarbon gas such as CF4. Alternatively, a liquid etch could be used comprising phosphoric acid, which preferentially removes nitride. The device produced in this manner has transistors all facing to the same surface. The transistors in this embodiment are shown as naked gate transistors, having a gate oxide, not having a metallic conductor on the gate. In other embodiments a gate electrode can be used.

Figure 5:
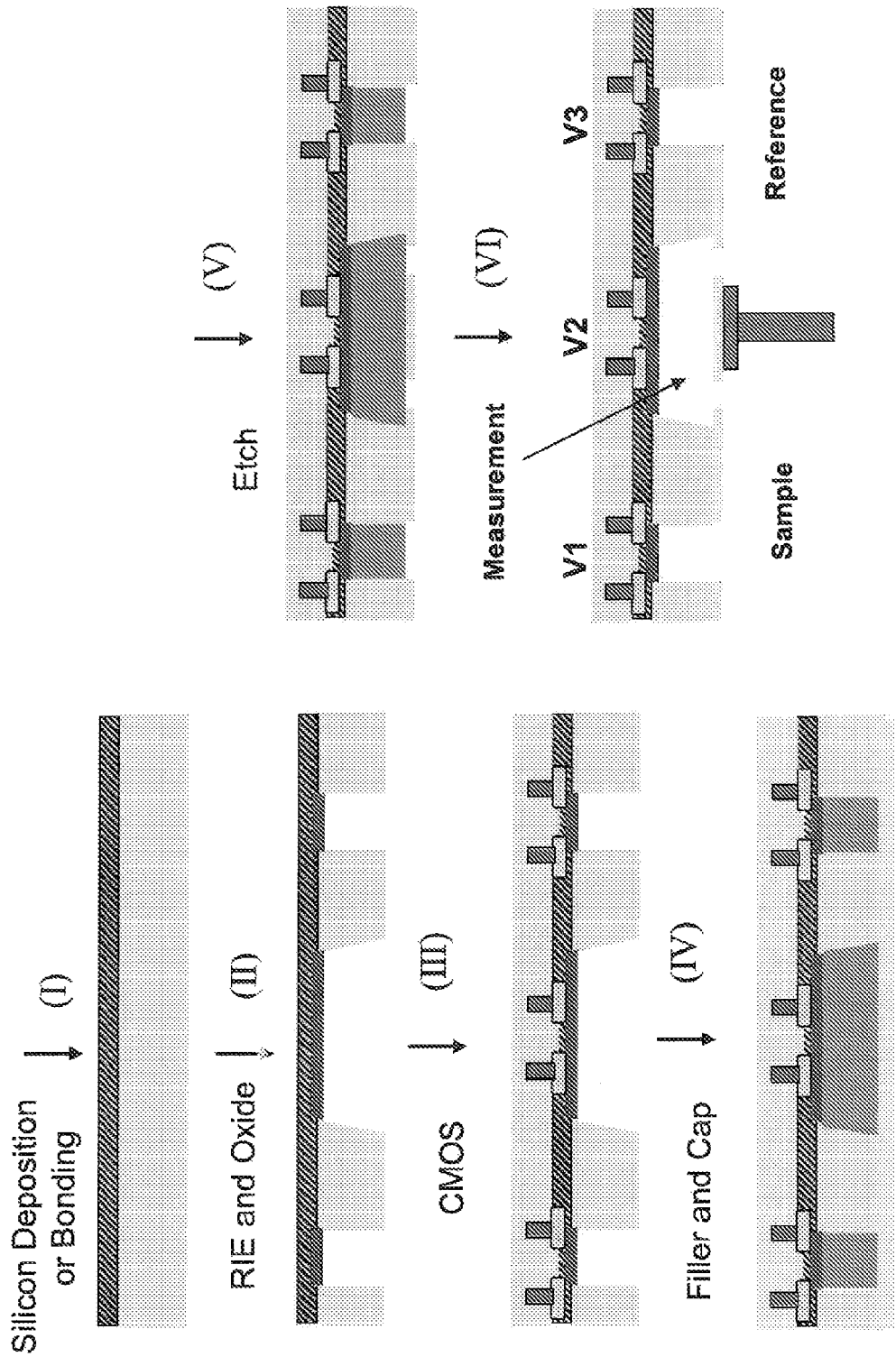
FIG. 5 is schematic diagram of an alternative process for fabricating a device of the invention using a semiconductor/sapphire substrate.

An alternative approach for forming a back surface cavity uses a semiconductor such as silicon on a sapphire wafer and is shown graphically in FIG. 5. Advantages to using sapphire substrates are the inherent selectivity in etch between the gate oxide, substrate, and filler. In step (I) silicon is either deposited onto or bound to a sapphire substrate. In step (II), etching, for example using reactive ion etching (RIE) is used to produce the central cavities and access to the outer device regions and gate oxide is produced. In step (III) CMOS processing is used to produce the appropriate electronic components such as transistors. In step (IV), the cavities are filled, for example with a nitride, and capping layer, for example using an oxide, is produced. In step (V), the capping layer is etched to produce holes, and in step (VI) the nitride is etched out and barrier components are added to separate the sample and reference chambers. An RIE etch with a Ni mask can be in excess of 7:1 with high anisotropic aspect ratio. In both back surface cavity architectures, the electrically induced depletion regions are formed from potentials on the back surface while the electrical connections to the sensing circuits are on the top surface. This provides design freedom to enhance the materials for diffusion barrier of water into the device on the back surface. In both cases, the nanopore fabrication can be performed after IC fabrication as the ports are available and unobstructed.

Vertical Through Wafer Chamber

Figure 6:
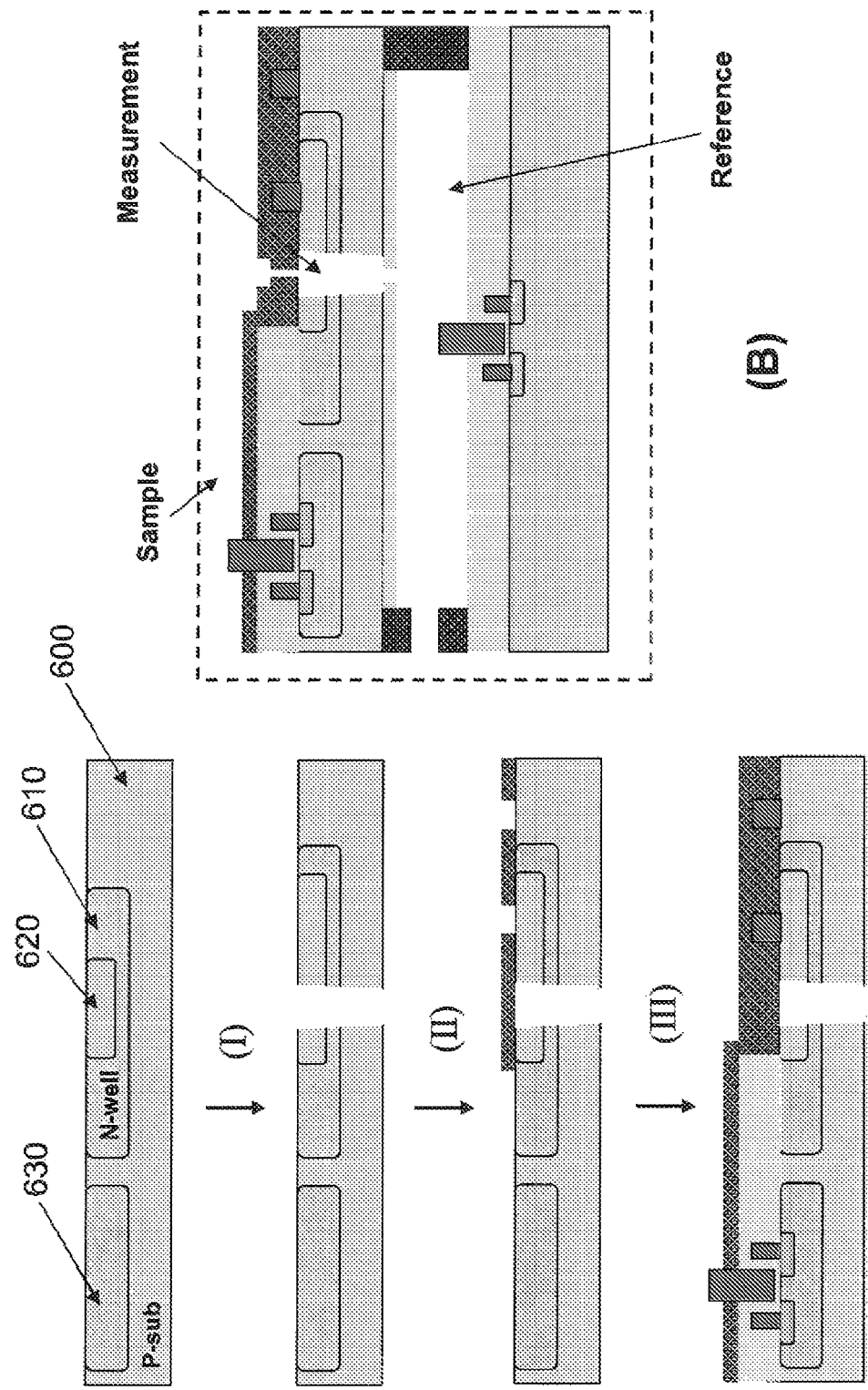
FIG. 6(A) is schematic diagram of a process for fabricating a device that incorporates a vertical IGFET.
FIG. 6(B) shows an embodiment of the incorporation of a vertical IGFET into a device of the invention using a second wafer.
Figure 7:
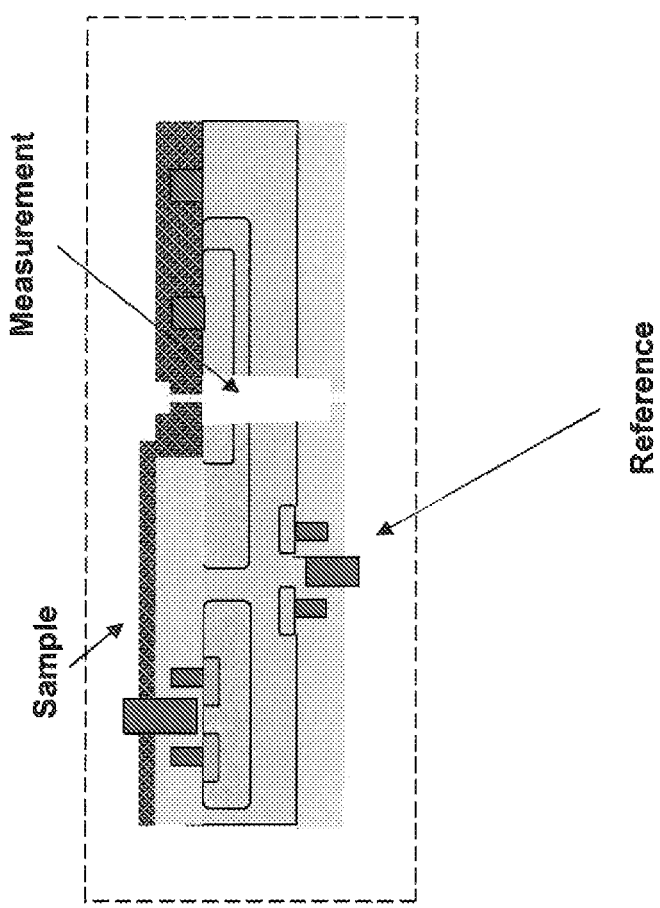
FIG. 7 shows a device of the invention incorporating a vertical IGFET in a single wafer with a sample electrode on the top surface, and a reference electrode on the bottom surface.

In other embodiments the measurement of potential drop across the nanopore can be accomplished through the wafer. This is shown in FIG. 6 and FIG. 7. In these cases, a vertical IGFET is invented that utilizes the multiple layers that are exposed when a through hole via is etched. Referring to FIG. 6(A), an NMOS device that is vertically oriented is made by patterning a shallow n-well 610 in a p-type substrate 600. Within this well, a counterdoped p-layer 620 near the surface is fabricated. In the vertical dimension, two p-type layers are separated from each other by an n-layer. Several techniques of insulating layers in the vertical well can be used that are familiar to those skilled in the art. In the case where additional field oxide needs to be patterned from the thin gate oxide in the n-well, it is envisioned that growth and etch cycles with contrast between n and p type boundaries can be used to vary the thickness of the resulting oxide.

An additional n-well 630 is patterned adjacent to the center region to provide an isolated sense transistor for the upper reservoir potential. The center region is etched through the wafer in step (I). In step (II) a nitride cap layer is deposited and contact holes for the top p-source layer and the substrate drain region are made. The top layer PMOS device is fabricated in the n-well. A TEOS oxide is deposited on the back surface to provide a reference resistance output port etch.

In some embodiments, as shown in FIG. 6(B), a second wafer containing the bottom reservoir (reference) sense transistor is attached to the first wafer by a polymer spacer. This spacer also acts as the receptacle for the lower reservoir. The electrical connection to the sensor output can be made to the top wafer or the detection can be performed off chip from the top and bottom wafer outputs.

In another embodiment, as shown in FIG. 7, the lower reservoir transistor (reference) is fabricated on the back surface of the wafer. In this case, the top and bottom surfaces can be processed in tandem (each process step performed on both sides before proceeding to the next). In this case, the wafer is the barrier between the two reservoirs and it is disclosed that the edges of the device can be patterned with a polymer to create an integrated fluidics system with multiplexed through hole vias and vertical IGFET devices.

Chambers Formed after Semiconductor Fabrication

Figure 8:
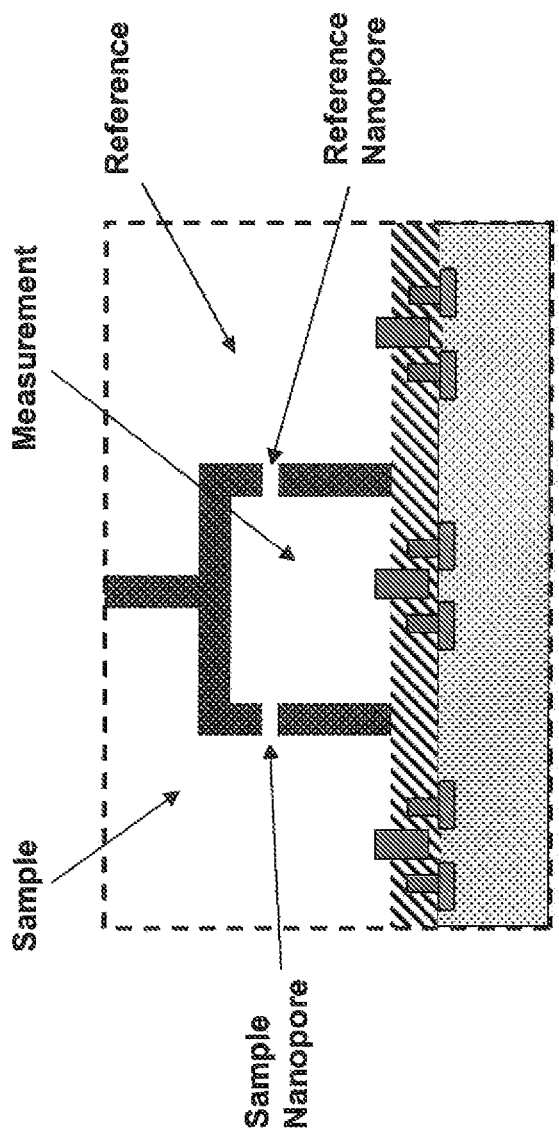
FIG. 8 shows an embodiment of a device of the invention in which sample, measurement, and reference transistors are fabricated on the top surface of a substrate, and a fluidic chamber is provided on top of the substrate to define the relevant fluid regions and provide the sample and reference nanopores.

In another embodiment the measurement circuits can be fabricated in the semiconductor wafer and the chambers and ports added in a post fabrication step. These chambers can be fabricated, for example using a low temperature polymer deposition process after the CMOS device is fabricated. These fluid guides can be patterned and assembled with the nanopore assembly at the point of use. An example representation of this invention is shown in FIG. 8.

A method to create three chambers where the input port is used to create the first reservoir a middle chamber with the nanopore and reference resistive port and the right port representing the exit reservoir is disclosed. In this case, the nanopore is not accessible from the top layer and the pore will need to be fabricated during the polymer fluid guide assembly.

For any of these methods the pores that are formed can either comprise the final solid state nanopore, or the pores can be further treated to produce the nanopores used for analytical measurements. For instance, in some cases, the pores can provide the base for forming hybrid solid state/protein nanopores. In some cases, the pores can be larger openings that will accommodate a lipid bilayer into which a protein nanopore can be included.

Ratiometric Measurement Circuit in CMOS, NMOS or PMOS

Figures 9, 10:
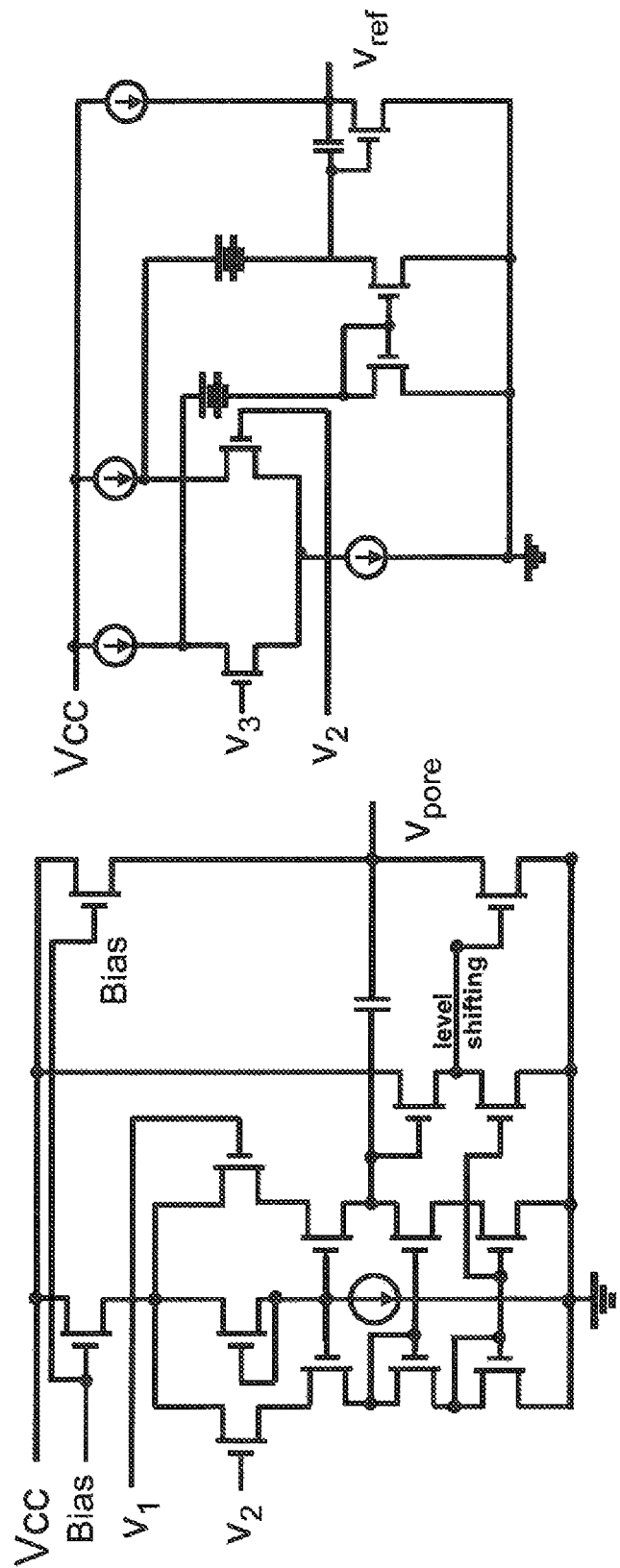
FIG. 9 shows a circuit diagram for implementation of the device of the invention in CMOS.
FIG. 10 shows a circuit diagram for implementation of the device of the invention in NMOS.

The CMOS circuit shown in FIG. 9 can be designed to operate with Bi-CMOS, NMOS or PMOS only devices. In the case of Bi-CMOS, the sensor transistors would be fabricated in NMOS or PMOS to provide electrical isolation between the fluidic circuit and the electrical readout (typically >10 G-ohm). The amplification can be performed with bipolar junction (BJT) technology. There is significant advantage in differential amplifiers designed with BJT technology as the open loop gain can be higher providing a higher level of common mode noise rejection. This also improves the insensitivity to thermal and voltage variations across the system introducing a noise and error signal.

FIG. 10 shows an NMOS representation of a differential amplifier. The interstage coupling network contains level shifting elements due to the lack of a complimentary PMOS device; these amplifiers use a similar architecture to the CMOS devices. A differential input stage drives an active load. A second gain stage follows. If a large off chip load is required (i.e. a high capacitance bus and bond pad), an output stage would be needed. To determine the gain and CMRR of these devices, each stage gain can be cascaded due to the inherent isolation from MOS devices which does not load down each following stage.

$$A_{v1} = \frac{g_{m1}}{g_{o2} + g_{o2}}$$

where transistor 1 and 2 are input devices and transistor 2 is from the active load.

Similarly, in the second stage:

$$A_{v2} = \frac{-g_{m1}}{g_{o2} + g_{o4}}$$

This means that the overall gain is a function of $g_m/g_o$ and therefore directly related to the set point of the biases and the channel lengths. For example, in a 0.5 um process with minimum channel length, the overall gain of these devices is 490*490 or 250,000. The channel length can be increased or decreased to set the gain properly. If the channel length were increased (or the $V_{gs}$-$V_t$ bias reduced) to increase gain, the frequency response would be adversely affected. The maximum differential input voltage would also be reduced so each design parameter has tradeoffs which can be tailored to match the specifications of the fluidic port geometries and speed.

Fluidic Wheatstone Bridge

Figure 11:
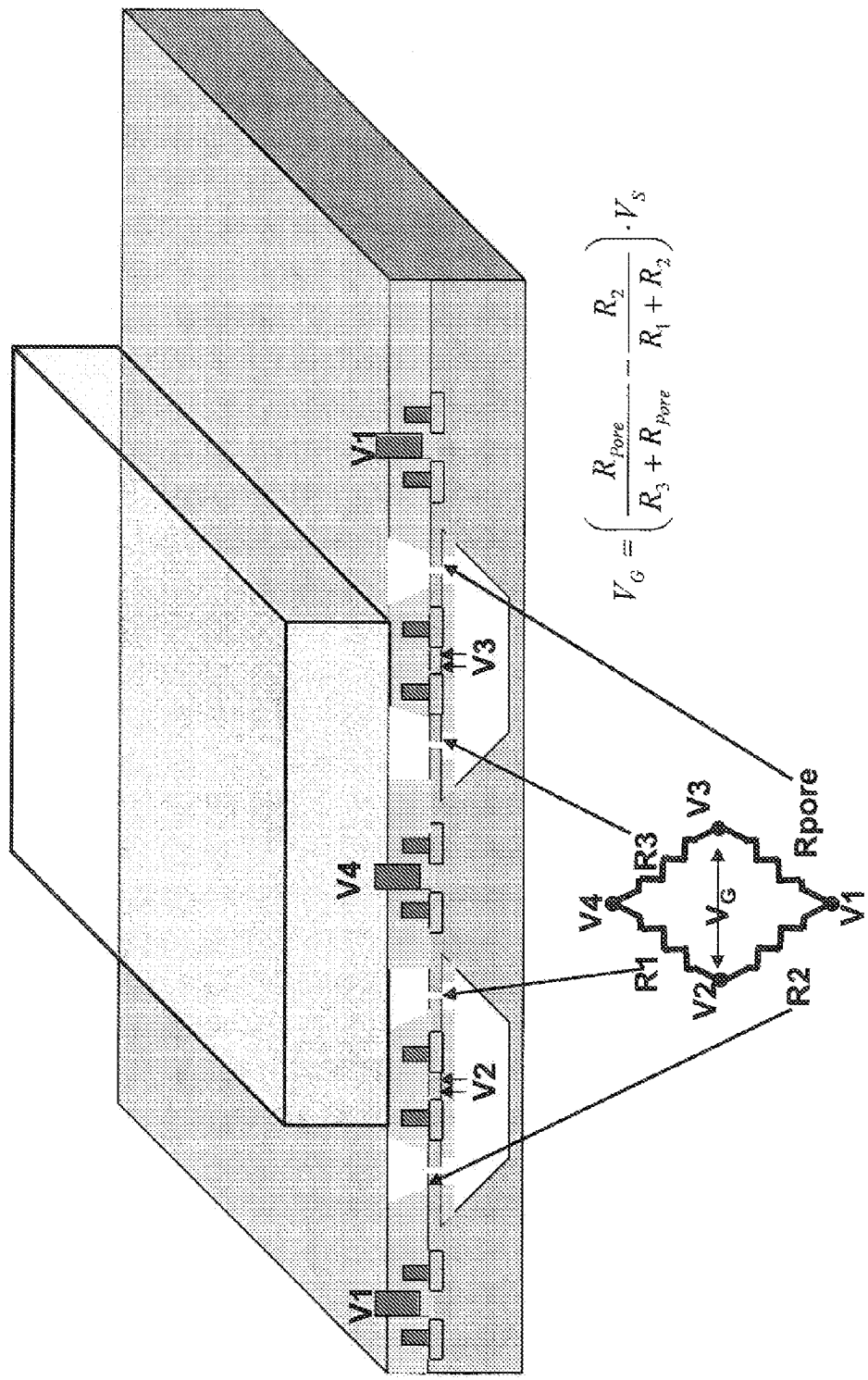
FIG. 11 is a drawing of a device of the invention which uses the electrolyte equivalent of a Wheatstone Bridge to measure nanopore current.

In another aspect of the invention, the unknown resistance can be measured accurately using a technique of the ratios of known resistances commonly known in electrical design as a Wheatstone Bridge. A fluidic circuit version of this device is shown in FIG. 11. In this approach, the parallel currents formed in each chamber are used to perform a ratio where the unknown resistance of the nanopore is determined from the three known resistances. The equation for the determination of the pore resistance can be measured directly from the two voltages V2 and V3 and tracks linearly with the applied voltage. This is also shown in FIG. 11.

$$\frac{V_3 - V_2}{V_1 - V_4} = \left(\frac{R_{Pore}}{R_3 + R_{Pore}} - \frac{R_2}{R_1 + R_2}\right)$$

The same folded cascade and ratio circuits described in the previous sections perform the identical difference and ratio operations and can be fabricated in CMOS with the detection and nanopore fluidic design. It can be shown that this circuit is an improvement as the determination of the reference ports R1, R2 and R3 can be made to set the operating point of the circuit independent of the more fixed nanopore.

In the device shown in FIG. 11 there are four fluidic regions. Sample reservoir in contact with the transistors measuring V1, a first measurement reservoir in contact with the transistor measuring V2, a second measurement reservoir in contact with the transistor measuring V3, and a reference reservoir in contact with the transistor measuring V4. There are four nanopores, associated with the resistances $R_{pore}$, $R_2$, $R_1$ and $R_3$.

Protecting the Reference Port

In some cases, the sample molecules that pass from the sample region into the measurement region will also be driven to pass through the reference port into the reference region. The passage of such molecules through the reference port can produce potential changes that may interfere with the ability of the reference pore to provide a consistent reference potential. One approach to this reducing or eliminating cross talk from the reference pore is to electronically compensate for these potential fluctuations, for instance by identifying spikes or troughs in potential between V2 and V3. In some cases, the current changes in the reference port can be compensated for by employing an additional chamber comprising another potential sensor such as an IGFET. The V2 measurement that was shared in the non filtered circuits can be split into V2a and V2b values. The pore potential would then be V1-V2a and the reference resistance port potential would be V2b-V3. An approach involving compensating for the potential changes in the reference port can work especially where there are sporadic events which may not substantially overlap in time. It can also work well for approaches such as the sequencing using current blockade labels described herein, where the same type of blockage that occurs at the sample port where the polymerase is attached will not occur at the reference port.

In some cases, the sample molecules that are transported into the measurement reservoir can be prevented from entering into the reference pore. For example, a membrane, sorbent, gel, or filter can be disposed between the nanopore and reference port that traps or excludes sample material that exceeds a certain size, or that has certain properties, functioning, for example, as an entropic barrier to transport through the reference nanopore. Compounds can also be provided that will selectively bind to the sample. Such selective binding can be performed by antibodies which can be directed to the sample molecules by the structure of the sample molecules, or through affinity tags on the sample molecules.

As used herein the term nanopore, nanometer scale aperture, and nanoscale aperture are used interchangeably. In each case, the term generally refers to an opening which is of a size such that when molecules of interest pass through the opening, the passage of the molecules can be detected by a change in signal, for example, electrical signal, e.g. current. In some cases the nanopore comprises a protein, such as alpha-hemolysin or MspA, which can be modified or unmodified. In some cases, the nanopore is disposed within a membrane, or lipid bilayer, which can be attached to the surface of the microfluidic region of the device of the invention by using surface treatments as described herein and as known in the art. In some cases, the nanopore can be a solid state nanopore. Solid state nanopores can be produced as described in U.S. Pat. Nos. 7,258,838, 7,504,058 In some cases, the nanopore comprises a hybrid protein/solid state nanopore in which a nanopore protein is incorporated into a solid state nanopore. The impedance of a given pore can be controlled in some cases both by controlling the size of the opening and also by controlling the length of the pore. For example, in some cases, a small, e.g. 2 nm diameter pore that has length of 3 nm may have the same resistance as a pore that is 10 nm pore with a longer length. This relationship can be used to produce a measurement pore with one diameter and a reference pore with another diameter where each has a similar impedance either blocked or unblocked. For example, a relatively small, short pore can be used as the measurement aperture, and a nanopore with a larger diameter and longer length can be used as the reference pore. The larger, longer pore will tend to be less sensitive to the presence of a molecule passing through it than will be the smaller pore, and yet each will have a similar impedance. This can be useful in designing a reference pore that provides a steady impedance reference.

Sequencing with a Polymerase Proximal to Nanopore

One aspect of the invention comprises measuring sequence information about a nucleic acid polymer by incorporating a polymerase enzyme proximal to a channel or nanopore. The requirements of the channel for this embodiment can be different than that for other embodiments described herein. Unlike the nanopore sequencing methods which measure the transport of a single stranded template nucleic acid through a nanopore, which generally utilize a narrow and short nanopore (on the order of a few nm in diameter and length), for this method, a longer channel and/or a wider channel can be used. The diameter of the channel can be a few nm to tens or hundreds of nanometers in diameter. In some cases the pore will not be cylindrical in shape. In some embodiments, the same solid-state, and biological nanopores such as alpha-hemolysin and MSPA can be used.

Figure 12:
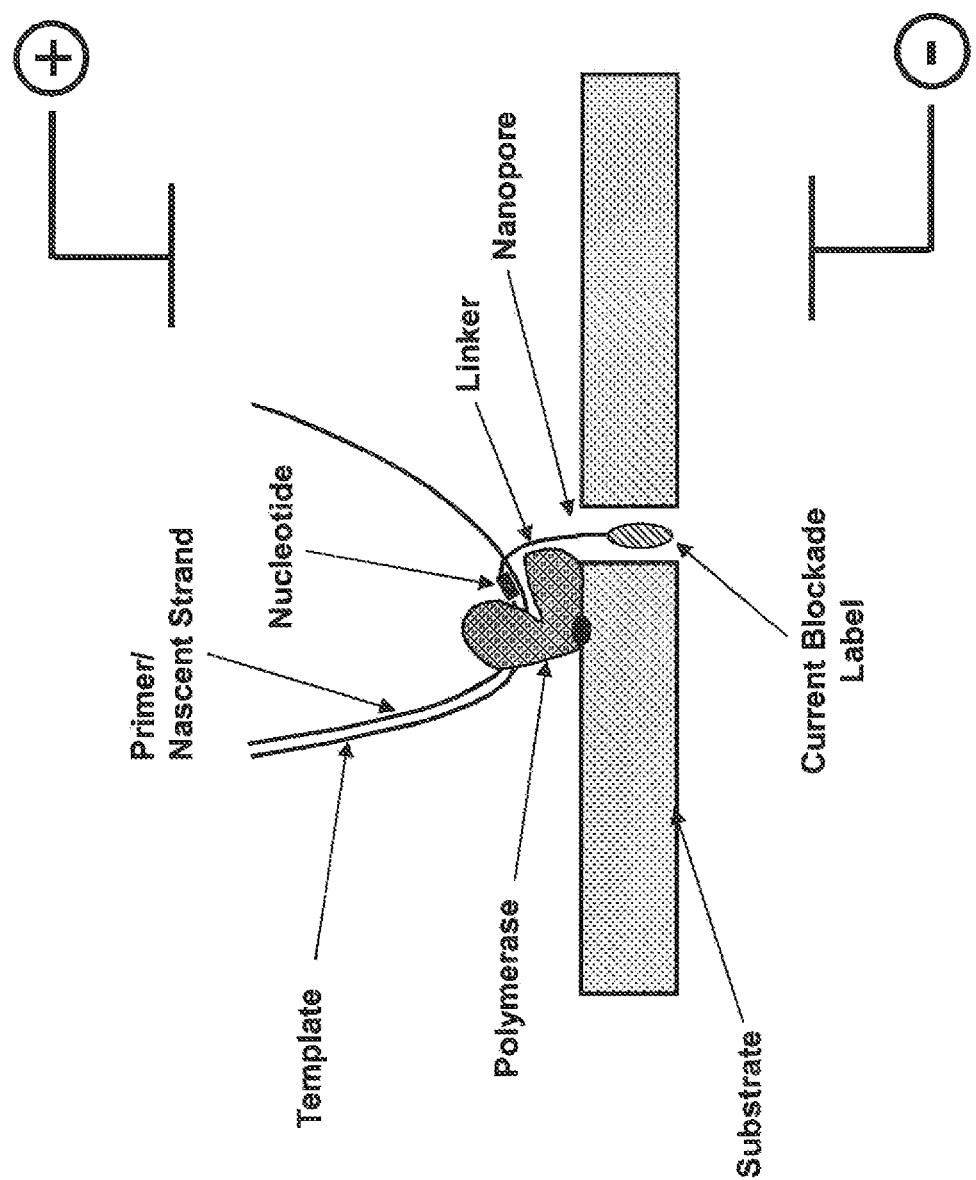
FIG. 12 illustrates a method of the invention for nucleic acid sequencing using a polymerase attached proximate to a nanopore and one or more nucleotide analogs comprising current blockade labels.
Figure 13:
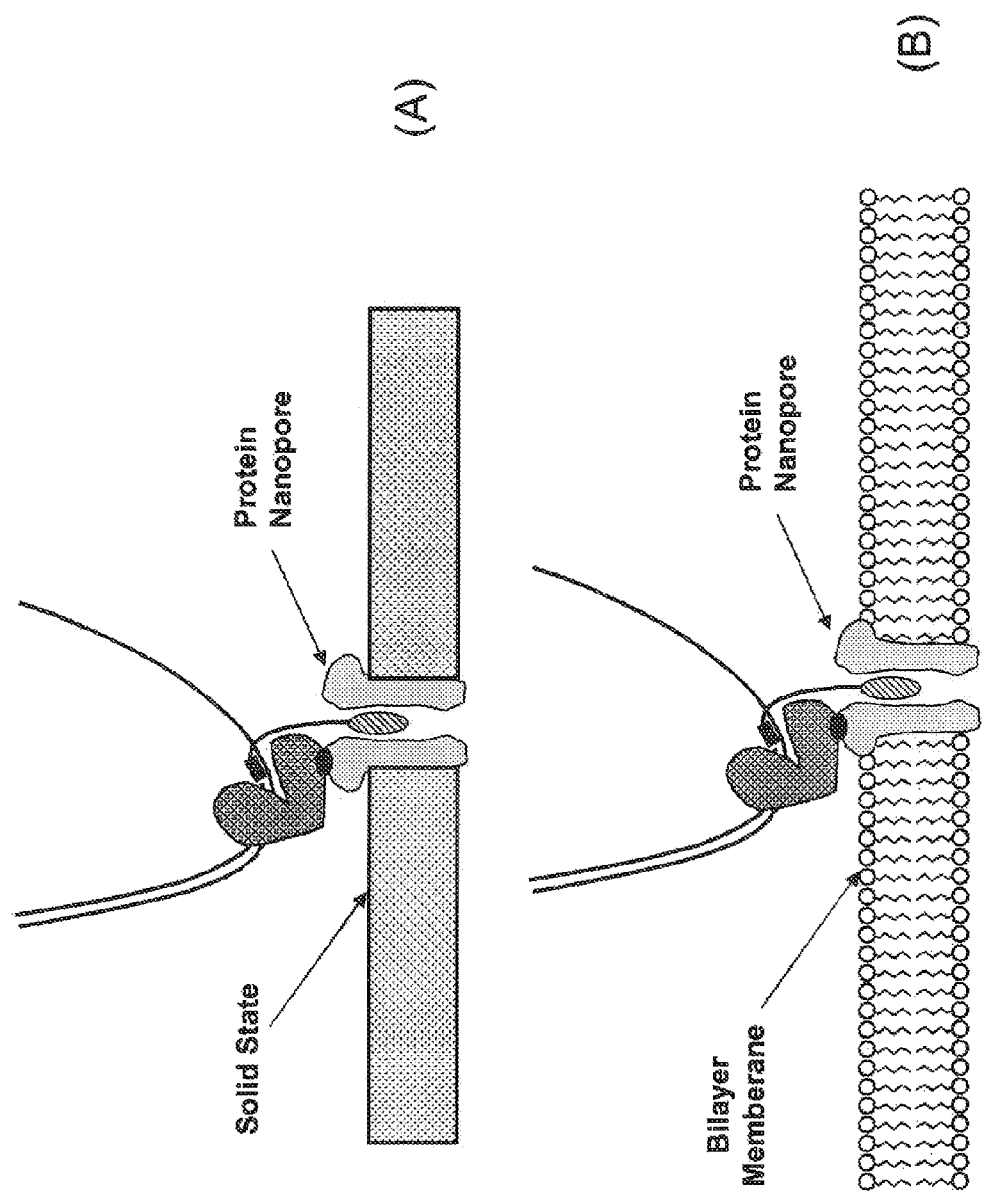
FIG. 13(A) illustrates carrying out sequencing using nucleotides with current blockade labels in a hybrid solid state/protein nanopore.
FIG. 13(B) illustrates carrying out sequencing using nucleotides with current blockade labels in a protein nanopore in a bilayer membrane.

In the methods of the invention, a polymerase is positioned proximal to the nanopore, generally on the side of the nanopore with the positive drive electrode). Typically, a primer-template will be associated with the polymerase. With the polymerase positioned in this manner, the DNA will generally not be attracted to enter the nanopore, but rather will tend to be pushed away from it by the main drive field in the nanopore. Detection of nucleotide binding takes place by the attachment of a current-blockade label that will tend to be pulled into the pore, and will cause at least a partial blockage of current. In some embodiments the current-blockade label will have positive electrophoretic mobility (or 'mobility'). FIG. 12 and FIG. 13 show a current blockade by an nucleotide as it is held within the polymerase prior to incorporation. FIG. 12 shows a system comprising a solid state nanopore, FIG. 13(A) shows a system with a hybrid nanopore, and FIG. 13(B) shows a system having a protein nanopore within a lipid bilayer. In FIG. 12, the current-blockade label is attracted to the negative electrode in an applied field. When a correctly base-paired nucleotide binds in the active site of the polymerase, the current blockade label is attracted into the nanopore (the moiety of the nucleotide has opposite sign of electrophoretic mobility compared with DNA). The blockade moiety's passage through the nanopore will be arrested by the linker that joins the blockade moiety to the nucleotide. The blockade will thus reside inside the nanopore for as long as it remains bound to the polymerase. During the time that the nucleotide is within the active site of the polymerase, the current through the nanopore will be reduced, producing a detectable signal. Free nucleotide that traverses the nanopore will produce only a very short blockage, as there will be no tether to an attached object to prevent the molecule from traversing the pore. In some cases, the composition of the solution, especially the background ionic species, are chosen such that when at least one of the blockade labels passes through the pore, the passage does not disturb the current. The different nucleotide types can be distinguished via different current-blockade-labels that can be differentiated by their different impacts on the electrical signal.

While the descriptions described herein refer to blockade labels that decrease the conductivity through a nanopore when present, there are cases in which the presence of a blockade label such as a charged label will increase the conductivity through the pore. These labels can be referred to as providing negative blockage. It is understood that the methods of the invention described for positive blockage can also be used with negative blockage.

Referring to FIG. 12, a polymerase enzyme is attached to a solid substrate proximal to or near a nanopore in the substrate. The polymerase is complexed with a template nucleic acid. The substrate is immersed in a solution containing the reagents necessary for carrying out polymerase mediated nucleic acid synthesis. As shown in the figure, a nascent strand is being synthesized complementary to the template. In the reaction medium are provided nucleotides having a linker and a current blockade label. Drive electrodes are in contact with the solution, providing a voltage drop across the nanopore. The voltage drop causes ions to pass through the nanopore. With the polarity as shown, having a positive potential above the substrate relative to the potential below the substrate, positive ions will tend to be driven through the nanopore from the top of the substrate where the enzyme is attached to the bottom of the substrate. When a nucleotide having a charge blockade label enters the active site, the current blockade label is held within the nanopore, partially blocking the current flow. Measurement electrodes (not shown) are provided to detect the amount of current flowing through the nanopore. A blockage of the nanopore by a blockade label can be detected as a drop in current, providing an indication that the labeled nucleotide is in the active site. During or after the incorporation, the current blockade label can be removed or cleaved to allow for the incorporation of the next nucleotide. After cleavage of the current blockade label, the blockade label is free to transport through the nanopore. This unblocks the nanopore allowing the current to return to its unblocked levels.

In a preferred embodiment, the current blockade label is attached to the nucleotide analog on the polyphosphate portion other than at the alpha position such that when the nucleotide is incorporated into the growing strand, the current blockade label, attached to the cleaved portion of the polyphosphate is released. This type of label allows for observing the addition of nucleotides by the polymerase in real time as the nucleotides are incorporated. For example, sequencing of a DNA template can be carried out using four nucleotide analogs corresponding to A, G, T, and C, each having a different charge blockade label which shows a different level of current blockage. There will be a background current of ions passing through the nanopore due to the applied electrical field, this will generally include the passage of some current blockade labels. While the passage of these freely diffusing labels through the pore may cause a detectable change in signal, the pulses corresponding to these events will be fast compared with the amount of time that a nucleotide analog will spend in the active site when it is being incorporated. Thus, the compositions, systems, and methods of the inventions allow for real time sequencing of nucleic acids using electrical rather than optical detection. While described in terms of a single nanopore, it is anticipated that the current invention will be most useful in allowing for the simultaneous sequencing of multiple templates using multiple nanopores.

Figure 14:
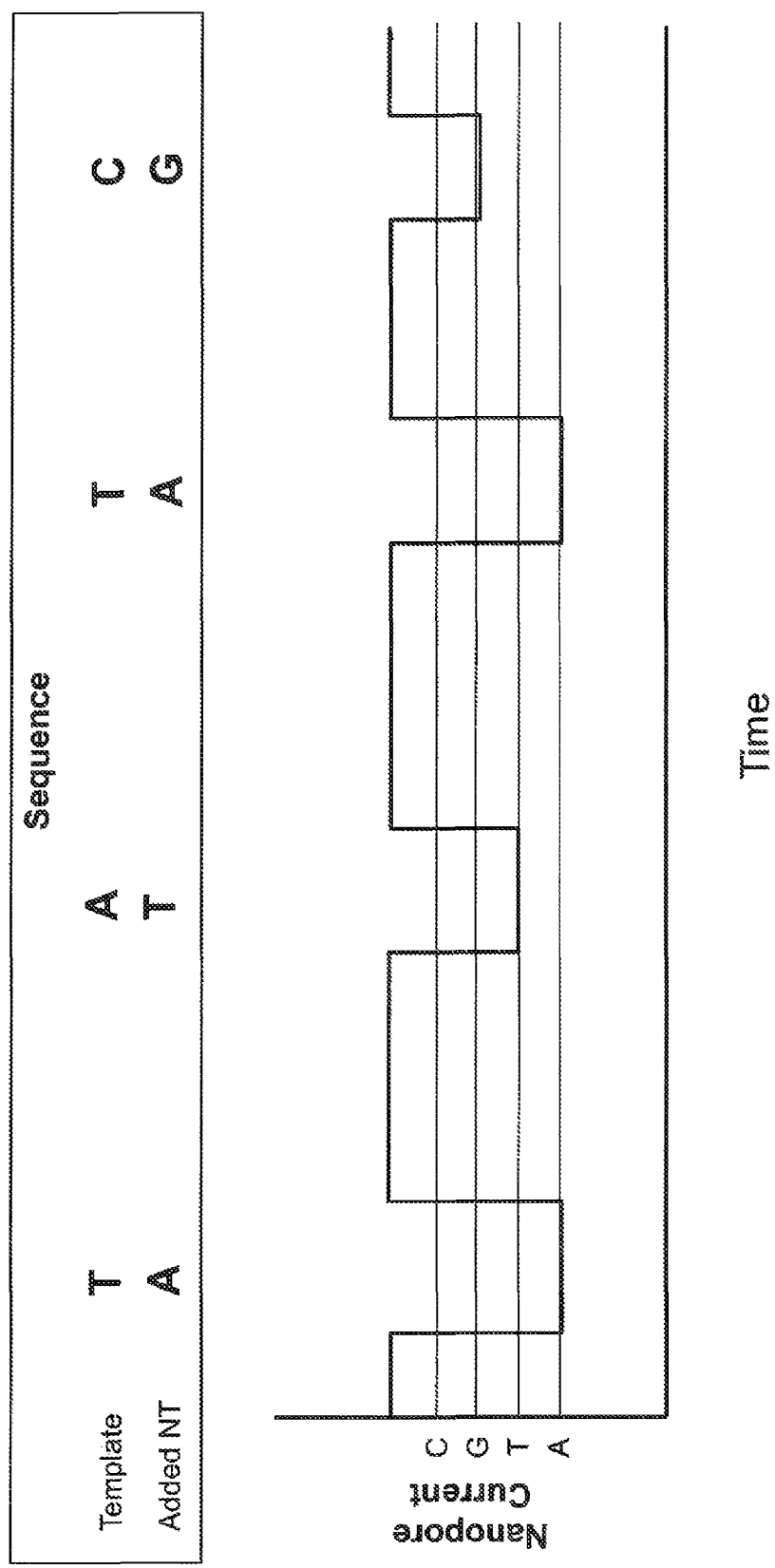
FIG. 14 provides an illustration of how sequencing can be performed using four nucleotide analogs, each with current blockade labels that provide a different magnitude of current blockage.

FIG. 14 provides an illustration of how sequencing can be performed using four nucleotide analogs, each with current blockade labels that provide a different magnitude of current blockage. Observing a dip in the nanopore current for a period of time consistent with nucleotide incorporation provides an indication that the nucleotide has been incorporated. For the system shown, each of the nucleotide analogs has a current blockade label that blocks the nanopore to a different extent, with C blocking the pore the least, followed by G, T, and A which blocks the nanopore the most, causing the largest drop in current. In the figure, a drop in current corresponding to the current blockade group on the nucleotide analog corresponding to A is detected. After a period of background current flow, a current blockage is seen corresponding to T. Following this, current blockages for the appropriate durations are observed for nucleotides corresponding to A and G. These current measurements indicate that a string of ATAG has been added to the nascent strand, indicating that the template sequence is TATC in this region.

One source of potential error with respect to base calling in sequencing with blockade labels is the presence of non-cognate sampling, which is when a non-cognate nucleotide analog "samples" the active site. While the non-cognate nucleotide analog will eventually be eliminated from the active site, while it is sampling the active site its current blockade label may be in the nanopore, providing a blocking signal that can be mistakenly interpreted as an incorporation event. One way to distinguish a non-cognate sampling event is by time. Generally, a non-cognate nucleotide analog will spend less time in the active site than the cognate nucleotide analog during incorporation. This difference in time of blockage can be used to distinguish a non-cognate sampling event from an incorporation event. The methods of the present invention provide another tool for distinguishing such events. When the nucleotide is cleaved, only the linkage and blockade group pass through the pore, whereas after a non-cognate sampling event, there is no cleavage, and the whole nucleotide analog may pass through the pore. The difference in the signals from these events can be used to correctly identify an incorporation event.

Another source of potential error is due to a "branching" event in which a cognate nucleotide analog enters the active site, but does not become incorporated. In some cases, the time that a cognate nucleotide analog that is not incorporated spends in the active site will be shorter than the time a cognate analog spends in the active site when incorporated. As above for non-cognate sampling, where the branching event occurs, no cleavage will take place, so there will be no passage of a cleaved blockade label and linker. The presence or absence of a characteristic signal from a cleaved blockade label through the pore can therefore be used to distinguish a branching event from an incorporation event.

It is known in the art that a broad class of molecules can produce faithfully detectable current blockade signals when lodged in nanopores. See e.g. Branton et al. "The Potential and Challenges of Nanopore Sequencing", Nature Biotechnology v. 26, 1146-1153, 2008. The nanopores can be protein (e.g. biological), solid-state, or hybrid nanopores. To measure the blockade signals, electrical detection systems are constructed that produce signals from such blockades that have high signal-to-noise ratio even in the megahertz regime. Because the binding time of correctly base-paired nucleotide in the polymerase will be in the millisecond regime, there is abundant bandwidth and signal-to-noise to detect these events and discriminate them by a variety of means (examples of which are discussed below). Given a suitable charge, the blockade label will diffuse into the nanopore with extremely high probability, as at this size scale the polymer will sample its available configuration space >100 times faster than the enzyme can incorporate on average. The blockade will sample the space inside the nanopore. A suitable blockade will have an appropriately large and positive mobility such that it will be held in the nanopore sufficiently well to be detected. It is known in the art that DNA molecules with just a few charged chain links experiencing the high-field region will be deterministically driven in the downstream direction through pore. Therefore, but utilizing a relatively small number of charges attached to the blockade moiety it will be possible to reliably position the blockade inside the nanopore.

In some aspects, the invention provides a method for determining sequence information about a template nucleic acid molecule comprising: providing a substrate having at least one nanopore extending therethrough, having an opening on the top and on the bottom of the substrate, and having a single polymerase enzyme attached proximal to the to opening of the at least one nanopore, the polymerase enzyme complexed with a primed template nucleic acid; contacting the substrate with a sequencing reaction mixture comprising reagents required for polymerase mediated nucleic acid synthesis including one or more nucleotide analogs, each comprising a current blockade label, providing a voltage drop across the nanopore such that when the base portion of the nucleotide analog is complexed with an attached polymerase enzyme, the current blockage label enters the nanopore, resulting in a measurable change in current through the nanopore; measuring the current through the nanopore over time to detect the incorporation of nucleotides into a growing strand; and identifying the type of nucleotide incorporated into the growing strand, thus determining sequencing information about the template nucleic acid molecule.

The attachment of the polymerase enzyme proximal to the opening in the nanopore allows for the blockade group to extend, at least partially, into the nanopore. Thus the optimal distance of the polymerase enzyme's attachment from the nanopore depends on the type of linker and charge blockade group that is part of the nucleotide analog. In general the enzyme should be within about 1 nm to about 100 nm from the nanopore, or from about 2 nm to about 50 nm from the nanopore, or from about 2 nm to about 20 nm from the nanopore. In some cases the polymerase enzyme is attached directly to a protein nanopore structure. By attaching the polymerase to the nanopore protein structure, a relatively close and relatively consistent distance between the polymerase and the nanopore itself can be established. In some cases, rather than being attached outside of the pore, the polymerase is held within the pore. Where the polymerase is held within the pore, the pore will generally be larger to accommodate the polymerase. For example, a polymerase can be on the order of 9 nm in diameter, so the nanopore having a polymerase within it will generally be larger than 9 nm, for example from about 10 nm to about 50 nm in diameter or from about 15 nm to about 30 nm in diameter.

The voltage drop across the can be adjusted to optimize the flow of ions through the current. The applied voltage will depend on factors such as the types and levels of ions, the sizes of the pores, and the desired field in the region of the pore. The drive voltage can be kept low enough to avoid problems with oxidation and reduction reactions at the electrodes. In addition, as described herein, the drive electrodes are generally positioned such that where voltages high enough to result in electrochemistry are applied, any products from such electrochemistry will not interfere with the processes occurring within the nanopores.

This method of the invention is analogous to optical methods of sequencing by synthesis using terminally optically labeled nucleotides as described, for example, in Eid et al. (2009) "Real-time DNA sequencing from single polymerase molecules" Science 323:133-138 and supplemental information, in which the presence of the nucleotide in the active site can be determined in the presence of a background of diffusing labeled nucleotides. The current method of sequencing in nanopores is distinctly different than other methods of nanopore sequencing, for example where a single stranded nucleic acid molecule is transported through a pore, and the sequence determined by the characteristics of the blockage of the current. In the current method, the signal that is produced has a duration which reflects the kinetics of polymerization by the polymerase. This kinetic information can be useful in many respects, including improving raw accuracy, and assigning quality values. In addition the kinetic information can be used for determining whether a base is an unnatural base or has been modified, e.g. methylated. See, e.g. U.S. patent application Ser. No. 12/635,618 filed Dec. 10, 2009.

The method has numerous variations, several of which are described here. In some embodiments the blockade is attached to the terminal phosphate, or any phosphate other than the alpha phosphate portion of the nucleotide. In this way, the catalytic step of incorporation of the nucleotide by the polymerase will result in the cleavage of the bond between the blockade label and the nucleotide, allowing the blockade to quickly pass through and clear the nanopore. After cleavage, the polymerase translocates to the next position on the DNA template and the process is set to repeat without any memory of the prior event. In this way, average readlength of the system will be dictated by the processivity of the enzyme. This can result in average read lengths of greater than 1,000, greater than 10,000, or greater than 100,000 bases.

In some aspects, the invention provides a composition comprising: a polymerase enzyme attached to a substrate proximal to a nanopore, and nucleic acid sequencing reagents including at least one nucleotide analog, the nucleotide analog having the structure NS-PP-L-B wherein NS comprise a nucleoside moiety, PP comprises a polyphosphate chain with at least two phosphates, L comprises a linker, and B comprises a charge blockade label. The NS moiety can be a deoxyribonucleoside or a ribonucleoside. The NS moiety will generally comprise one of the natural bases of RNA and DNA, but can also have synthetic bases or modified natural bases. Generally, the NS moiety is chosen to accurately base pair with the appropriate base on the template strand to provide for accurate construction of the nascent strand. The polyphosphate chain generally has at least two phosphates, but in some circumstance may have as few as one. The key attribute of the polyphosphate chain is to provide for enzymatic cleavage after the alpha phosphate in order to incorporate the nucleoside portion of the nucleotide analog into the nascent strand and to release the rest of the nucleotide analog from the enzyme upon incorporation. In some cases the polyphosphate chain has 2, 3, 4, 5, 6, 7, 8, 9, or more phosphates.

In other embodiments, the blockade label is attached to the ribose sugar, the base or the alpha phosphate of the nucleotide. In these embodiments other means are used to remove the blockade label. For example, labile linkers can be used that allow chemical cleavage of the group.

In other embodiments, the nucleotides are made non-incorporatable through, for example, an alpha-thioate moiety.

In this case binding will be unproductive and the label will leave with the nucleotide. This will result in a series of signals, each corresponding to a 'sampling' of the active site of the polymerase by a cognate, but non-incorporable nucleotide. To achieve processive sequencing in such a case, a mixture of native nucleotides and non-incorporatable, labeled nucleotides can be used. A native base incorporation would move the system forward by one base and the labeled unincorporatable bases would then sample in the active site, allowing detection of the identity of the new base in the active site of the polymerase. In this mode, the number of binding events per base would be uncertain, requiring the use of statistical methods to estimate the length of homopolymer repeats. This approach is analogous to the method described in U.S. Patent Application Publication No. 2010/0075332 entitled "Engineering Polymerases for Modified Incorporation Properties", which is based on optical detection, the entirety of which is incorporated herein by reference for all purposes.

Alternatively, a polymerase with weak 3'-5' exonuclease activity can be used along with blockade-labeled nucleotides that are blocked from further extension. For example, blockade-labeled dideoxynucleotides in a mixture with a small quantity of native nucleotide can be used. In this mode, the blockade-labeled dideoxynucleotides would be incorporated and would stay resident until cleaved by the exo activity, as the dideoxy nucleotides are blocked from further extension. This process would repeat until by chance a native nucleotide is incorporated, at which point the system moves to the next base. Alternatively, the blockade-labeled nucleotides could be labeled at the 3' position, having the same effect as a 3' dideoxy nucleotide. Alternatively, the blockade can be attached to the nucleotide in such a way that under the action of the electrical force, the attachment is prone to be overcome and break with a half-life that is on the same order with the kinetics of the polymerase. Other configurations of the various components will lead to useful DNA analysis with the blockade label attached to the base, the ribose sugar or alpha phosphate.

Figure 15:
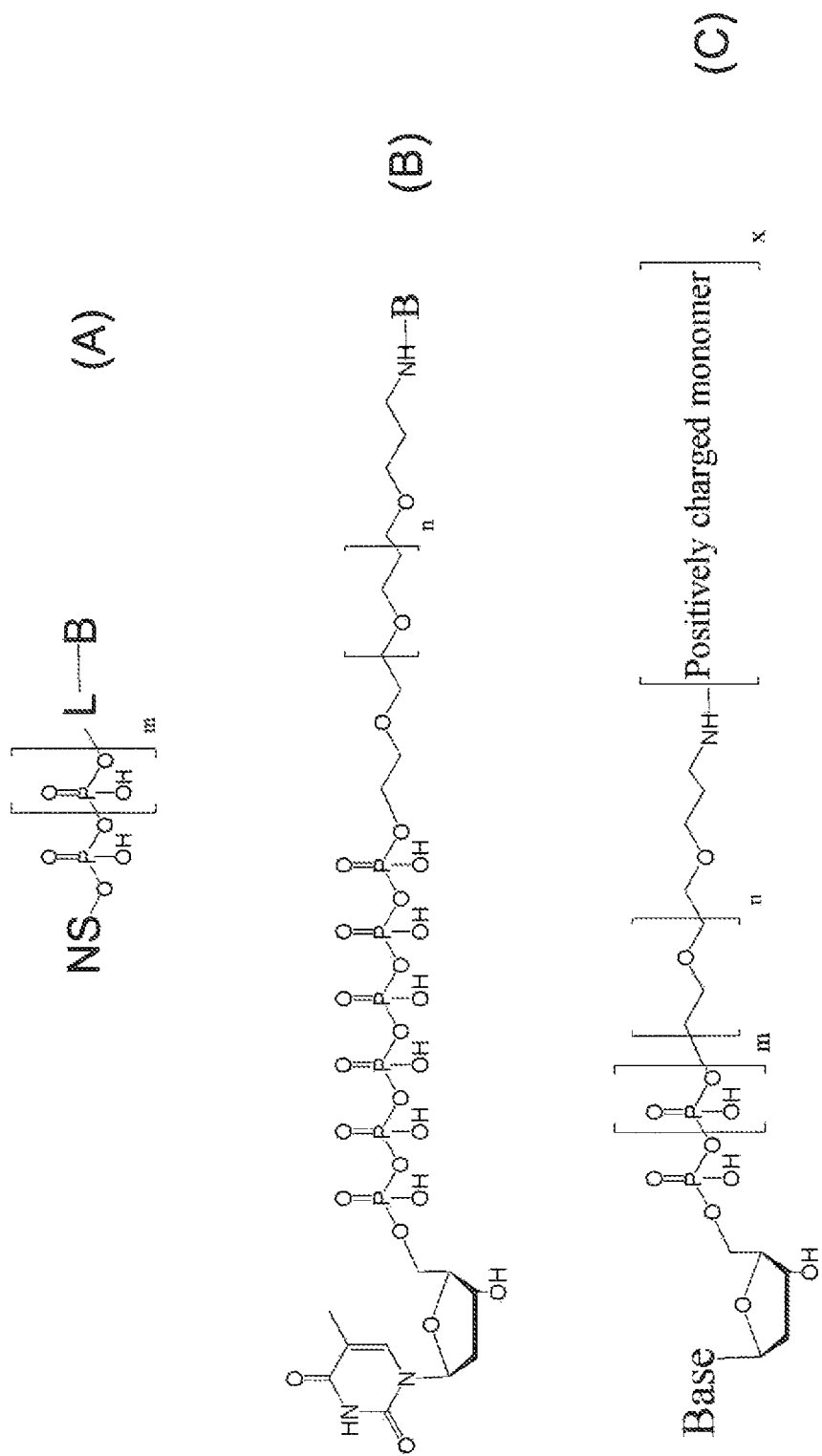
FIG. 15 shows some examples of exemplary nucleotide analogs having current blockade labels.

FIG. 15 shows some examples of exemplary nucleotide analogs with current blockade labels. FIG. 15(A) provides a structure having a nucleoside connected to a polyphosphate chain. For this structure, m can be from 0 to about 9. Typically, m is between 1 and 5.

L in structure 15(A) is a linker which links the phosphate chain to the blockade label. The linker has several important functions as part of the nucleotide analog. Its length is selected to properly position the charge blockade label relative to the nanopore when the nucleoside and polyphosphate portions are held in the active site of the polymerase. As described herein, in some cases the lengths of the linkers on different nucleotide analogs are different in order to provide a difference in the level of current blockage or the time characteristics of current blockage of the label. The linker can be a linear chain, and can be produced, for example, by putting together a series of monomeric units, such as ethylene glycol or alkane units. The linker can have functionality to aid in water solubility such as ether, hydroxy, or amine groups. In some cases, the linker can have charged groups to assist in control of the electrophoretic mobility of the cleaved portion of the nucleotide analog. For example, where the drive voltage is applied so as to transport positively charged molecules through the pore, positively charged groups can be incorporated into the linker to produce a cleaved portion with a higher net positive charge than from the current blockade label.

FIG. 15(B) shows an exemplary nucleotide analog in which the nucleotide analog comprises the nucleoside deoxythimidine having the base thimine (T). The polyphosphate chain has 5 phosphates, and the linker is comprised of polyethylene glycol. The length of the polyethylene glycol linker is controlled by the value of n, which can be any suitable number that allows for controlled current blockage. For example, n can range from about 10 to about 10,000, or from about 100 to about 100. B is a charge blockade label.

In some embodiments, there is a neutral linker used between the blockade label and the phosphates of the nucleotide. This linker allows for the correct positioning of the blockade label in the optimal part of the nanopore. This linker can be a polyethylene glycol or any of the large number of neutral, relatively inert polymer and copolymer compositions known in the art. In some embodiments the linker has length zero. In other embodiments, the linker is long enough to allow the positive mobility part of the molecule to completely pass the nanopore constriction and the modulation of the blockade is achieved using different linkers. This is conceptually the same as noting that the blockade label per se can include an arbitrarily large portion of what could otherwise be called linker and that the boundary between linker and label need not be notable as a change in the structure of the molecule.

FIG. 15(C) shows another exemplary nucleotide analog of the invention. The nucleotide analog has a deoxynucleoside unit which has a base that can be any suitable natural, unnatural or synthetic base which can be incorporated into the nascent strand by a polymerase enzyme. The charge blockade group comprises a polymer of positively charged monomer units. Here, the number of monomer units, reflected in the value of x determines the length of the charge blockade label and the net charge. The number of monomers, x, can be any suitable number. For example, x can be from about 1 to about 50, or about 2 to about 30, or about 3 to about 20. In FIG. 15(C), the polymer is indicated as being linear, but branched polymers can also be used.

Figure 16:
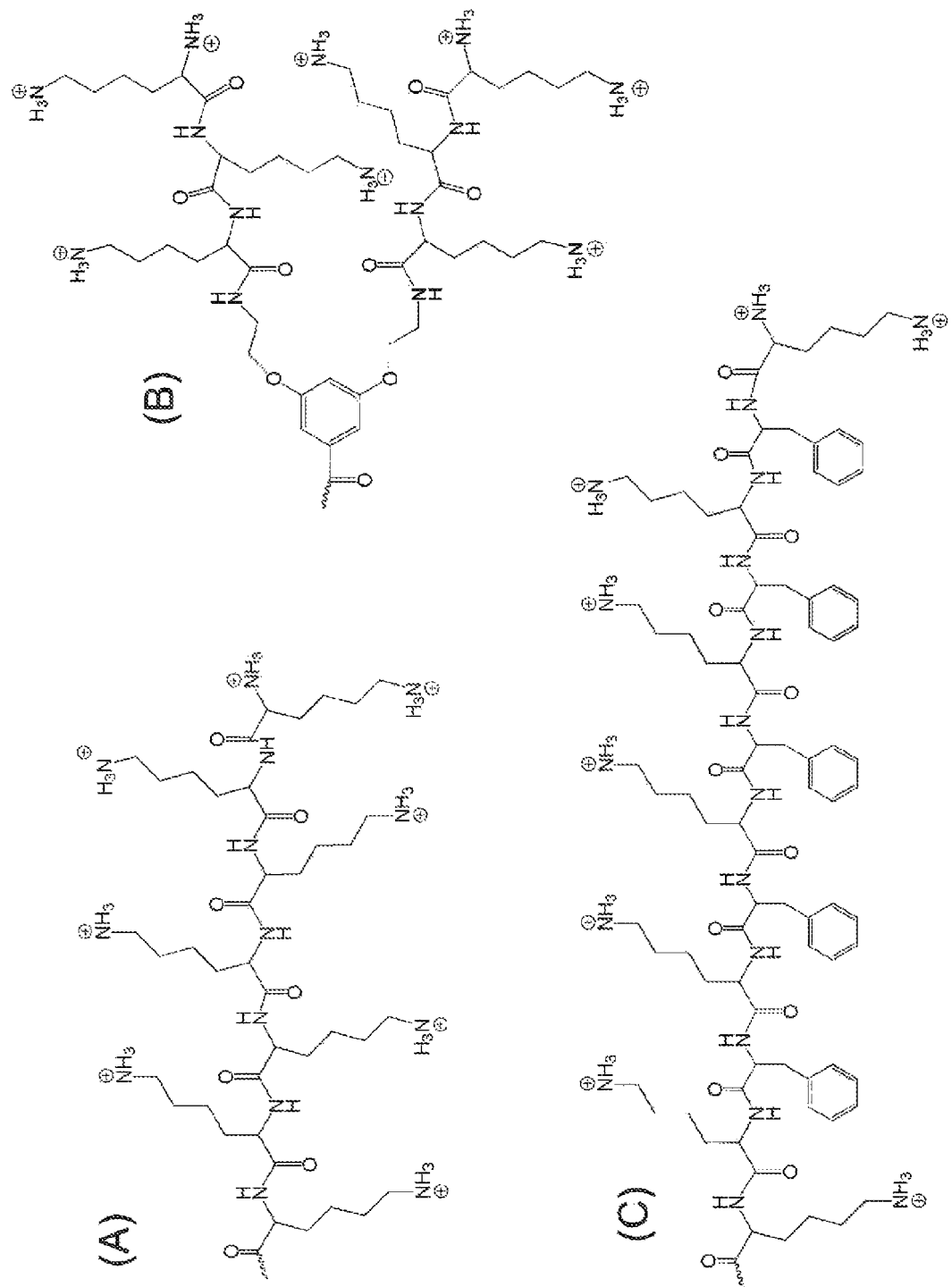
FIG. 16 shows some exemplary blockade labels.

The size, shape, and charge of the blockade labels can be used to adjust the effectiveness of current blockage, and the differentiation from other blockade labels. As discussed above the nanopores in the current invention can be different in size and shape, and can be larger in size than nanopores used, for example, to measure single stranded DNA translation through the pore. The size and shape of the nanopore and the size and shape of the charged blockade label can be mutually adjusted in order to improve the performance of the sequencing system. The blockade labels can be net positively charged, net negatively charged, or neutral, as required for forming an effective blockade. In some cases, the current blockade label is net positive in charge such that it will pass from the side of the pore with the polymerase to the other side of the pore with a positive voltage on the polymerase side of the nanopore. There are many ways of making positively charged groups that can be useful as charge blockade labels. One convenient method involves producing polymers from positively charged monomers. By adjusting the structure of the monomer, the length of the polymer, the molecular weight of the polymer, and the level of branching, a wide variety of blockade labels can be synthesized having a variety of properties. For example, the charge may be varied by monomer number, where each monomer unit has a given net positive charge, for example of 1, 2, or, 3. These types of blockade labels can be synthesized, for example, by solid phase synthesis, for example by solid phase peptide synthesis. Suitable monomers include lysine, alkylated lysines, diamino alkyl carboxylic acids, arginine, and ornithine. In addition bulkiness of the charge block group may be varied by branching or incorporation of other amino acids to provide pore blocking resistance. FIG. 16 shows some exemplary blockade labels.

FIG. 16(A) shows a blockade label comprising a linear polymer having 7 lysine monomers. FIG. 16(B) shows how branching can be used to produce a branched blockade label from lysine monomers. Here there is one branch point. Blockade labels with multiple branch points to increase the lateral extent of the label can be employed. FIG. 16(C) provides a linear structure having more bulk per charge than in FIG. 16(A). Many suitable blockade labels can be produced using controlled polymerization of charged monomers.

Figure 17:
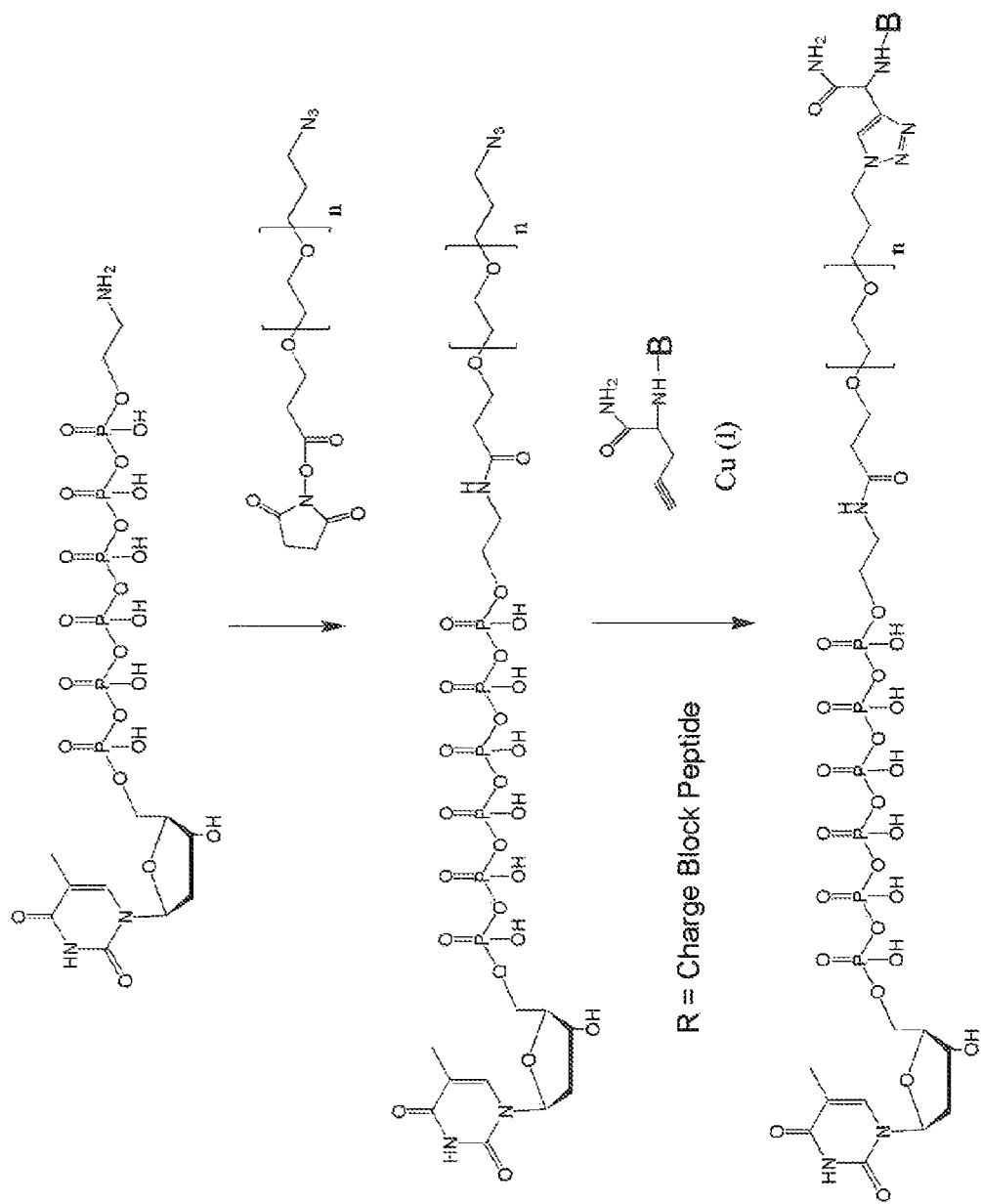
FIG. 17 shows an exemplary method of synthesizing a nucleotide analog of the invention.

FIG. 17 shows an exemplary method of synthesizing a nucleotide analog of the invention. In the first step, N-hydroxy succinimide coupling is used to attach the polyethylene glycol linker to an amine terminated nucleoside polyphosphate. In the second step, azide-alkyne Huisgen cycloaddition (click chemistry) is used to couple the current blockade label to the linker. Many methods for carrying out such coupling reactions to produce the nucleotide analogs of the invention are known in the art.

In one version, the current blockade label moiety is given a positive mobility by giving it positive charge. In another version, the positive mobility is given by selection of neutral species that cause organization of the surrounding medium so as to give it positive mobility, as described in (Knecht et al., J. Col. Int. Sc. 318, p. 477, 2008).

The blockade labels can be nucleotides or portions of nucleotides. For example the nucleotide analog could comprise a nucleotide such as an A attached to another nucleotide, such as another A. When one of the A's is associated with the polymerase prior to becoming incorporated, the other A acts as the blockade label. The label could also comprise multiple nucleotides concatenated together, e.g. 2, 3, 4, 5, 6, or more nucleotides either in a linear or in another, e.g. dendritic or star shaped configuration. In some cases, only one of the nucleotides will be accessible to the polymerase, and the other will always act as the blockade label. In some cases, both or all of the nucleotides will be accessible. In some cases the molecule can be a heterodimer, e.g. A-C, and T-G. Here, if the A is being incorporated, the C acts as the blockade label, and if the C is being incorporated, the A acts as the blockade label.

In various embodiments of the invention, the net charge on each of the polymer, template nucleotide, primer, linker, and blockade moiety are engineered to enhance the performance of the system. In some embodiments, the net electrophoretic mobility of the nucleotide, linker and blockade moiety combined is engineered to be zero, for example by giving the blockade moiety a charge that will be exactly opposite to the nucleotide under the buffer conditions used for the reaction. This is desirable in that there is no electrical repulsion of the nucleotides away from the polymerase that would decrease their effective concentration (and thus the rate of polymerization). At the same time, there would be no net force attracting the unused nucleotides into the nanopore where they would create background noise and waste reagent.

In some versions, the net mobility on various components of the reaction is negative to provide increased assurance that the component, such as the nucleotides will not traverse the nanopore. For example, a nucleotide that has 6 negative charges in the phosphate chain and only two positive charges in the current blockage moiety will have a net negative mobility. It is known that in commonly used nanopore DNA analysis configurations, the electric field can diminish so quickly because of the divergence of electric fields lines outside the nanopore that diffusion can overcome drift due to the main drive field. In some configurations of the polymerase position, pore diameter, and main drive field inside the nanopore, the diffusive force will overcome the electrical repulsion at the position of the polymerase, and there will be a small or negligible decrease in the concentration of available nucleotides at the position of the polymerase active site.

For these embodiments, polymerase positions further away from the nanopore, lower pore main drive fields, and smaller diameter pores will result in better availability of nucleotides at the polymerase active site. In the embodiment mentioned above the passage of the cleaved blockade label will actually be through the pore, because the net charge is negative, even after cleavage of the alpha-beta phosphate bond. In other embodiments, the number of positive charges might exceed the number or remaining negative charges, which would result in clearance of the cleavage product away from the pore. In other embodiments, the net mobility of the cleavage product might be zero, for example, by choosing a number of phosphates for the nucleotide one greater than the number of positive charges in the blockade label moiety. The cleavage product would generally not interfere with the further sequencing of the template, as the cleavage products are not capable of being immobilized by the polymerase to produce a detectable signal. The net charge on the nucleotide analog can range from about −100 to +100 or from −50 to +50 or from −20 to +20, or from −10 to +10. The net charge on the cleaved portion of the nucleotide analog comprising the linker and charge blockade label can differ from the net charge of the nucleotide analog by 1 to about 100, from 2 to about 50, or from 3 to about 20, or from 4 to about 10. The portion of the nucleotide analog comprising the linker and charge blockade label will typically be net positive, but where the application calls for a net negative charge, this can also be used. The drive voltage can be net negative or net positive from the top to the bottom of the nanopore either where the net charge on the nucleotide analog is positive or negative. In some cases, the polarity of the drive voltage is changed during the reaction. The choice of polarity of nucleotide analog, polarity of charge blockade label, and polarity of drive voltage can be made to optimize the sequencing performance of the system.

In some embodiments of the invention, labels are chosen whose conductivity, when mobile, is matched with the conductivity of the surrounding medium, but which when immobilized can cause either an increase or decrease in the conductivity of the channel, depending on the buffer conditions, the molecular volume, the permeability of the label molecule structure, and other parameters. In this way, the freely diffusing molecules are invisible in the conductivity signal, because they participate in electrical conduction to the same degree as the surrounding medium. In other embodiments, the labels are chosen so that freely diffusing labels induce an increase while an immobilized label causes a decrease in conductivity. In other embodiments the free labels decrease conductivity while the bound labels increase it. By providing an opposite sign of the influence it is possible to differentiate free from bound label while being able to see both. In other embodiments, the labels produce a different impact on conductivity before and after they have been disconnected from their analyte molecule. In this mode it is possible to visualize all three phases of the cycle: diffusive entry into the channel, binding in the molecule, and then release of the label after nucleotidyl transfer. In this way, productive vs. unproductive binding can be distinguished. In some embodiments, the connected label is invisible by conductivity matching, while the cleaved label is visible. In another embodiment, the free label is detectable while the cleaved label is invisible due to conductivity matching.

In some embodiments the cleavage product will have a strong dipole, which under some circumstances could result in the trapping of the cleavage product at the nanopore site. A number of approaches can be used to prevent this from having a negative impact on the sequencing. In many cases, operating conditions can be chosen that allow diffusion of the cleavage product to overcome the dipole trapping force. In some cases, conical openings for the nanopore can be used on the side that is expected to be the direction of egress. This will tend to reduce the dielectrophoretic trapping force, ensuring that the molecule will depart from the pore. In some cases, a time-varying drive field can be used that produces periods of no field on the nanopore. Because the diffusion of the cleavage product will be extraordinarily fast on the size scale of the nanopore, even periods of a few microseconds without field would be enough to virtually ensure departure of the cleavage product. This can be achieved by simply turning off the main drive voltage every 1-10 milliseconds for a period of 10 microseconds, or by the application of a alternating current component. The alternating current component can be applied which is equal in amplitude to the direct current component, so that at one extreme the field is zero. The frequency could be even in the 10's of megahertz, as the random nature of diffusion will allow occasional departure even if the zero field interval is much shorter than the average diffusion time. With potentially hundreds of thousands of attempts per polymerase residence time, there would be little chance of the cleavage product remaining in the pore during the next incorporation.

In other embodiments, the dipole trapping effect is exploited to reduce the chances of missing events due to unexpectedly fast catalysis by the polymerase. In these embodiments, conditions are selected in order to ensure the trapping of the cleavage product after catalysis. For example, the use of high charge levels on the two ends of the cleavage product, high nanopore fields and long neutral linkers will tend to provide that the cleavage product will become trapped after catalysis. This will lengthen the duration of pendency in the nanopore beyond just the enzyme residence time and allow detection of even nanosecond catalysis events that very rarely can happen by random chance. In these embodiments, parameters can be chosen that naturally allow for a moderate trapping time with spontaneous and random departure, or the drive field can be modulated to deliberately clear the cleavage product. In some embodiments the drive field can be modulated in closed-loop feedback with the detection so that the cleavage product is released after detection has been made.

In some embodiments, the dipole trapping effect is used exclusively to attract the blockade-label into the nanopore. In these embodiments, a purely AC field is applied, and the blockade moiety is chosen to comprise both positive and negative charge regions so that a mobile part of the label possesses a strong internal dipole that can extend into the pore. Then to ensure departure of the cleavage product after incorporation, the AC field can be amplitude modulated or periodically turned off to allow diffusion to remove the cleavage product. In these embodiments, the conductance of the pore is accomplished with AC impedance measurement rather than DC measurements. These embodiments are desirable because the drive electrodes can be fabricated monolithically with the device without fear of water electrolysis or dissolution of electrode metal caused by application of DC voltages.

In some embodiments, the net mobility of the nucleotide is positive. For example, a nucleotide can have three charges from the three phosphates, and a blockade that contains 8 charges, or the blockade plus the linker will have 8 charges. These nucleotides will be available to the polymerase irrespective of the main drive field applied, because they have a net mobility that drives them towards (and through) the nanopore. The cleavage product in this case will be even more positive in charge and thus have even greater positive mobility.

In some embodiments, the encoding of the identity of the nucleotides is through the use of blockade moieties with different degrees of interference on the nanopore conductance. In this way, the value of the blockade current during a blockade event will encode the identity of the base being sequenced. This difference in blockade can be achieved by using a blockade having different lengths of the same basic polymer, by using polymers that have side-chains of different length, by using polymers that have a different width of the polymer backbone, or by using different numbers of dendritically attached branched polymer side-chains.

In some embodiments the blockade moiety is identical between all four nucleotide types, and only the length of the neutral linker changes. The linker length will vary the equilibrium position of the blockade moiety inside the nanopore, which will in turn change the conductance of the nanopore. This approach can be used, for example where the nanopore has a shape that is not cylindrical but in which the diameter of the nanopore changed with the length of the channel. For example, the nanopore can become more narrow with distance from the polymerase, could become wider with distance from the polymerase or could vary in shape with distance in another manner that results in a different level of current blockage for each of the labeled nucleotides. For example, the pore can be most narrow at the top, widening in the middle, then constricting again. Alternatively, the pore can become narrower and wider two or three times over the length of the pore. These changes in lateral dimension with distance can provide for there being different levels of current blockage characteristic of blockage labels that differ, for example in length, width, and/or net charge. The different lengths of the linkers are chosen to provide well-separated current blockage readings for each of the bases.

In some embodiments the variance in the blocked current with time is used to encode the identity of the base. That is, different current blockade labels can give a different profile of current blockage versus time as it blocks the nanopore. In cases where the electric field is increasing positively in the nanopore with position, and the extension of the spring formed by the polymerase, nucleotide and linker also increases position positively in the nanopore, there can be several stable local energy minima or "equilibrium" positions, which are similar in energy, but having different current blockage characteristics. Oscillations between the stable "equilibrium" points can result in a repeatable variation with time of the blockage current. Using the pores described herein that vary in diameter with distance can provide such "equilibrium" positions.

In some cases, e.g. in a diffusing system the blockade label can oscillate due to Brownian motion between the two states, leading to fluctuations in the conductance of the nanopore. This oscillation is manifested as a variation of the blockade current over time. This variation can produce a magnitude and frequency spectrum which can be adjusted, for example, by choice of linker spring constant and length, allowing for identification of the nucleotide that has a characteristic oscillation. Nucleotides or analogs that can thus be identified by either or both of the magnitude of the current blockage and the spectrum of the electrical oscillation they produce. Voltage level discrimination and oscillation discrimination can be used in conjunction to increase the resolution of the system. In some cases, oscillations looks like noise, but noise with reproducible and identifiable characteristics including the frequency and the magnitude of the signal. These different types of noise can be used like different colored dyes are used to differentiate between different nucleotide analogs, thus, we refer herein to a distinguishable type of noise as a noise color. While the measurement of current blockage by the blockade label is described as a measurement of current, it is understood by those in the art that this current can be measured by measuring a voltage. Where we refer to measuring current or voltage, it is to be understood that one can be used to measure or represent the other with respect to measuring ion flow through the nanopore. In addition to current and voltage, resistance or impedance measurements can also be employed as described in more detail herein to measure the level of current through the nanopore and the blockade current.

One aspect of the invention is the utilization of additional parameters beyond just the amplitude of a signal to classify the species that inside a nanopore. Such parameters are measurable over the duration of a pulse. Two general categories of measurement scenarios are: quasi-equilibrium measurement and non-equilibrium measurement.

In quasi-equilibrium measurement, there is some static constraint that remains in place over the duration of the event, and that the removal of that constraint effectively determines the end of the event (except for a negligibly short interval at the end while the detectable object clears the nanopore). Though the constraint is fixed, the rest of the components of the system are free to move, and this leads to fluctuations in the signal. For example, diffusion (or equivalently Brownian motion) will cause movement of the label. Under most circumstances, that motion will be correlated with changes in the current across the nanopore, and thus the voltages that might be measured elsewhere in the system. Because of this, aspects of the detectable moiety such as the submolecular diffusion constant (the diffusibility of just that part of the molecule, even when another part of the molecule is constrained) will change the speed of those motions and thus the characteristic frequencies with which the observed voltages or currents will change. For example, a fast diffuser will generally have a whiter noise spectrum, while a slower diffuser will tend to produce a pinker noise spectrum.

The noise color can be used as the basis for a discriminator, for example, by 1) taking the noise signature over a region of interest (e.g. over the duration of the event), 2) performing a Fourier transform analysis, or an autocorrelation analysis and examine the spectrum of the noise over the range of frequencies available (e.g. from f=1/T where T is the duration of the pulse, up to the cutoff frequency of the amplifier system, or somewhat beyond the cutoff). This process will result in a digitally sampled noise amplitude as a function of frequency. This could be represented by as few as two samples (a low frequency region and a high frequency region), 3, 4, 5, 6, 7, 8, 9, 10, 11, 12, 16, 32, 64, 128, 256, 512, 1024 or more bins. The values in these bins could be discrete samples of a function or they represent integrals over a region of interest of the idealized continuous function. This set of discrete values can be represented as a vector that can be classified by one of many machine learning systems such as k-means clustering, SVM, CART or boosted CART, PCA and many others. Thus, as described herein, noise color can be used to discriminate detectable moieties. Detection systems that are based on noise color can be referred to as "noise-color identification systems", and when moieties engineered for producing different noise color are used, they are referred to as "noise-color tags". In a sequencing system, when nucleotide base sequence is identified on this bases it can be referred to as a noise color sequencing system (whether the noise color is intrinsic to the bases or the result of noise-color tags).

Other aspects besides the diffusion constant can affect the noise color of the signal. For example, in the embodiments that use linkers with different elastic constants, this will affect the magnitude of these diffusive fluctuations, which will then affect the amplitude of the noise signal (not to be confused with the amplitude of the DC current during the event—this is referring to the RMS noise of the signal over the duration of the event.). In analogy with color systems that have RGB, or HSV, color can be generalized to include the "brightness" of the color. In the above-mentioned spectrum analysis model, this would result in the values in the vector being larger for moieties capable of larger excursions, and lower values for moieties that are more constrained in position. Some or all of these signals can be exploited in the machine learning paradigm indicated above. There are many aspects that can affect the size of the excursions. Beyond linker elasticity, there is the local field divergence at the equilibrium average height. If the field strength is building commensurately with the increase in tension in the linker implied by that level of extension, then the potential energy distribution will be relatively flat, leading to larger excursions in the position which will lead to larder excursions in the signal and thus larger values in the noise color vector. So generally, conical interior shapes that locally get narrower on passage from upstream to downstream will lead to high color values, while cones which locally get wider at the point of equilibrium will lead to lower noise color values. Alternatively, highly aspherical moieties will have some rotational diffusion and will, if they are free to rotate in the channel, lead to fluctuations in the current and thus higher color values and moieties that are roughly spherical, or aspherical moieties that are confined in channels that force a particular orientation will create lower color values.

In addition to using compensatory changes in the electric field at positions of larger extension of the linker, one can use combinations of wall profile and linker length and elasticity that have more than one stable equilibrium point (at zero temperature). Such a configuration can occur, for example, if there is a constriction in the pore, and one equilibrium level has the blocking moiety just upstream of the constriction. If that blocking group makes an excursion into the constriction, the fields grow faster than the restoring forces of the linker spring, and the blocking group passes through the pore and comes to rest at another equilibrium point on the other side of the constriction. At finite temperatures, in quasi-equilibrium, the system will make stochastic transitions between the states at rates governed by the activation energies between the stable states and the attempt frequencies in the Arrhenius law. There can be stable points, unstable points, metastable points and there can be 1, 2, 3, 4 or more stable points or metastable points. These will affect the level-setting of the data. A further aspect of color is the amplitude spectrum of the noise. By way of example, all of the samples acquired over the duration of such a quasi-equilibrium event could be collected and those values used to create a histogram. This histogram could have, for example, 2 bins, 3, 4, 5, 6, 7, 8, 9, 10, 11, 12, or more bins, or 16, 32, 64, 128, 256 bins or more bins. As before, these binned values can be treated as described before for the frequency values. These would then be used as before as inputs to machine learning algorithms such as SVM, CART, boosted CART, k-means clustering, PCA and others. This vector and the other color-associated vectors can be used simultaneously in discrimination by the same methods.

A further refinement of the invention employs the temporal and spatial information in a combined framework. For this a hidden Markov model can be used that models the quasi-equilibrium state as a series of transitions with probabilities, where the system is allowed to consider the joint distributions of local amplitude and frequency.

In addition, due to the dissipation of energy from the passage of current through the nanopore, there is no fundamental requirement that the motion of the moiety be ergodic—that is to say that the moiety can undergo cyclic fluctuations that have a preferred direction of cycling. This is analogous to driven oscillations of a structure in wind, such as the famous Tacoma Narrows Bridge event. This can lead to more sharply peaked distributions in the various color vectors and thus more distinctive color vectors.

Thus, in certain aspects, the invention provides a method for determining sequence information about at template nucleic acid molecule comprising: providing a substrate having at least one nanopore extending therethrough, having an opening on the top and on the bottom of the substrate, and having a single polymerase enzyme attached proximal to the opening of the at least one nanopore, the polymerase enzyme complexed with a primed template nucleic acid; contacting the substrate with a sequencing reaction mixture comprising reagents required for polymerase mediated nucleic acid synthesis including two or more nucleotide analogs, each comprising a current blockade label, each blockade label capable of exhibiting a different noise color, providing a voltage drop across the nanopore such that when the base portion of the nucleotide analog is complexed with an attached polymerase enzyme, the current blockage label enters the nanopore, resulting in a measurable change in current through the nanopore; measuring the current through the nanopore over time to detect the incorporation of nucleotides into a growing strand; and identifying the type of nucleotide incorporated into the growing strand by identifying the unique noise color of the blockade label, thus determining sequencing information about the template nucleic acid molecule. In some cases, each of the blockade labels comprises a linker having a different elastic modulus.

In some cases, the identity of the nucleotide is determined, at least in part, by a characteristic current profile as the cleaved charge blockade and linker pass through the pore. Thus, for example, all four nucleotides may provide an indistinguishable blockage of the nanopore current while they are in the active site, but after cleavage, the transport of the blockade label and linker through the pore will provide the information required to identify the type of nucleotide that was incorporated.

The net charge of the nucleotide before cleavage and the net charge of the cleavage product comprising the linker and charge blockade group can be selected such that the cleavage product transports through the pore, while the nucleotide analog does not. This can be accomplished, for example, by adding net negative charge to the base and or sugar portions of the nucleotide analog, such that the nucleotide analog has a net negative charge, but the cleaved linker and charge blockade label have a net negative charge. Nucleotides analogs whose net charge changes upon incorporation and cleavage are described, for example in U.S. Pat. No. 6,936,702 entitled Charge Switch Nucleotides, which is herein incorporated by reference in its entirety for all purposes.

In some embodiments the polymerase is attached to a solid-state nanopore via a streptavidin-biotin interaction. In these cases, a small region around the opening is derivatized with biotinylated self-assembled monolayers using any of a variety of methods known in the art to spatially localize self-assembled monolayer deposition. Then streptavidin bound to biotinylated polymerase is introduced allowing binding of the polymerase proximal to the nanopore opening.

In some embodiments the polymerase is a fusion protein with one subunit of a multi-subunit biological nanopore. The use of a polymerase-pore fusion protein has the desirable property that the distance between the polymerase and the nanopore opening can be precisely controlled, assisting in the production of predictable current relationships for the different coded labels. The polymerase-pore fusion protein has an additional desirable property that the biological nanopore, the polymerase and the template to be sequenced can all be introduced at the same time. The polymerase-pore fusion protein can be used in conjunction with the hybrid nanopore strategy in which a solid substrate is produced having pores that are derivatized to attach a nanopore protein, and are of a size for which a single biological nanopore protein is held within pore in the substrate. With the present constructs, this approach can be used to produce an array in which one and only one polymerase, nanopore and template are present per solid state nanopore.

In some embodiments the polymerase is attached by a biotin-streptavidin interaction with a biological nanopore. Numerous methods are known in the art to create a biotin side-group on a protein at a pre-specified position. See, for example, the polymerase is then pre- (or post-) attached to the streptavidin and added to the system. See, for example, U.S. patent application Ser. No. 12/815,160 filed Jun. 14, 2010.

There are numerous attachment strategies known in the art with similar targeting methodologies to the above strategies. It is assumed that the one skilled in the art would adapt any or all of these biological interactions to immobilize the polymerase.

In some embodiments the polymerase is not attached to the nanopore. In some of these embodiments, a charge tag is attached to the polymerase via a long neutral linker just like the nucleotides, which traverses the nanopore, but because of the large electrical dipole and long linker the positive charged tag is unable to be pulled past the high field region in the nanopore out in the low field region on the other side. Thus the polymerase reaches a predictable equilibrium height above the nanopore with no covalent attachment. In these embodiments, a larger diameter pore may be used to accommodate two polymerase chains threading it.

The size of the pore used for sequencing using blockade labels will depend on the type of blockade label that is employed. One advantage of this method is that it does not require the use of extremely small, e.g. 2 nm to 3 nm biological nanopores. While these can be used in some embodiments, by using larger blockade labels, larger nanopores of about 4 nm to about 50 nm, or about 5 nm to about 20 nm or from about 8 nm to about 15 nm can be used. These can be either biological or solid state nanopores. For example, it is well known that one can use evaporative constriction or oxidative restriction after standard lithography to reliably produce nanopores in this range, e.g. on the order of about 10 nm.

All of these embodiments can take advantage of the integrated devices described herein such as the monolithically fabricated CMOS/fluidic devices, novel structures such as the naked-gate transistor, the anti-cross-talk methods such as the resistive opening, and the electronic circuits for improved amplification.

The methods above describe the polymerase as being attached proximal to the nanopore. While in many cases it useful for the polymerase to reside outside of the nanopore, in some embodiments, the polymerase will be immobilized within a nanopore, nanochannel, or microchannel. The use of polymerases within the pore is described, for example in U.S. patent application Ser. No. 12/757,789, filed Apr. 9, 2010, which is incorporated herein in its entirety for all purposes.

The methods and devices described herein can be used with polymerases immobilized within the pore. In some cases, the characteristics of blockade labels used for a polymerase within the pore will be different. For example, for a polymerase held within the pore, the length of the linker will generally be shorter than for a polymer held outside of the pore.

Template Nucleic Acids

The template nucleic acids of the invention can comprise any suitable polynucleotide, including double-stranded DNA, single-stranded DNA, single-stranded DNA hairpins, DNA/RNA hybrids, RNAs with a recognition site for binding of the polymerizing agent, and RNA hairpins. Further, target polynucleotides may be a specific portion of a genome of a cell, such as an intron, regulatory region, allele, variant or mutation; the whole genome; or any portion thereof. In other embodiments, the target polynucleotides may be mRNA, tRNA, rRNA, ribozymes, antisense RNA or RNAi. The target polynucleotide may be of any length, such as at between about 10 bases and about 100,000 bases, or between about 100 bases and 10,000 bases.

The template nucleic acids of the invention can include unnatural nucleic acids such as PNAs, modified oligonucleotides (e.g., oligonucleotides comprising nucleotides that are not typical to biological RNA or DNA, such as 2'-O-methylated oligonucleotides), modified phosphate backbones and the like. A nucleic acid can be e.g., single-stranded or double-stranded.

Polymerase Enzymes

Polymerase enzymes that are suitable for the sequencing reactions with charge blockade labels comprise any suitable polymerase enzyme capable of template directed nucleic acid synthesis. For example, suitable enzymes include those taught in, e.g., WO 2007/076057 POLYMERASES FOR NUCLEOTIDE ANALOGUE INCORPORATION by Hanzel et al., WO 2008/051530 POLYMERASE ENZYMES AND REAGENTS FOR ENHANCED NUCLEIC ACID SEQUENCING by Rank et al., and U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES." The modified polymerases may have modified properties such as (e.g., decreased branch fraction formation, improved specificity, improved processivity, altered rates, improved retention time, improved stability of the closed complex, etc.).

In addition, the polymerases can be further modified for application-specific reasons, such as improved activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

DNA Polymerases

DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol. Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, E. coli DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287.

RNA Polymerases

In some embodiments, the polymerase enzyme that is used for sequencing is an RNA polymerase. Any suitable RNA polymerase can be used including RNA polymerases from bacteria, eukaryotes, viruses, or archea. Suitable RNA polymerases include RNA Pol I, RNA Pol II, RNA Pol III, RNA Pol IV, RNA Pol V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from E. coli and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e. they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or systems of the invention include RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Reaction Conditions

The reaction conditions can be modified to provide both for a reliable current through the nanopore and for the activity of the polymerase enzyme. In particular, the ionic strength can be adjusted using small ions in order to obtain suitable enzyme activity and nanopore current. The reaction conditions can affect reaction rates. Reaction conditions can be manipulated, for example, to further slow a step or steps which are already slowed in a modified polymerase, or to slow an additional step, such that the resulting polymerase system exhibits two slow step behavior.

The polymerase reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors. Manipulation of reaction conditions to achieve or enhance two slow step behavior of polymerases is described in detail in U.S. patent application Ser. No. 12/414,191 filed Mar. 30, 2009, and entitled "Two slow-step polymerase enzyme systems and methods."

Enzymatic reactions are often run in the presence of a buffer, which is used, in part, to control the pH of the reaction mixture. The type of buffer can in some cases influence the kinetics of the polymerase reaction. For example, in some cases, use of TRIS as buffer is useful for obtaining a two slow-step reaction. Suitable buffers include, for example, TAPS (3-{[tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris (hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction. The pH can be adjusted to a value that produces a two slow-step reaction mechanism. The pH is generally between about 6 and about 9. In some cases, the pH is between about 6.5 and about 8.0. In some cases, the pH is between about 6.5 and 7.5. In some cases, the pH is about 6.5, 6.6, 6.7, 6.8, 6.9, 7.0, 7.1, 7.2, 7.3, 7.4, or 7.5.

The temperature of the reaction can be adjusted. The reaction temperature may depend upon the type of polymerase which is employed. Temperatures between 15° C. and 90° C., between 20° C. and 50° C., between 20° C. and 40° C., or between 20° C. and 30° C. can be used.

The ionic strength of the solution can be tailored to minimize the measured background in order to improve the ability to measure the current blockage. For example, the mobility and charge of some prevalent ions in the solution can be selected so that the impact of their passing through the pore produces a minimal change in current.

In some cases, additives can be added to the reaction mixture that will influence the kinetics of the polymerase reaction in a manner that can lead to two slow-step kinetics. In some cases, the additives can interact with the active site of the enzyme, acting for example as competitive inhibitors. In some cases, additives can interact with portions of the enzyme away from the active site in a manner that will influence the kinetics of the reaction so as to produce a reaction exhibiting two slow steps. Additives that can influence the kinetics include, for example, competitive but otherwise unreactive substrates or inhibitors in analytical reactions to modulate the rate of reaction as described in copending U.S. Utility patent application Ser. No. 12/370,472, the full disclosure of which is incorporated herein by reference in its entirety for all purposes.

Systems

The invention also provides for systems for nucleic acid sequencing. In some aspects the invention provides a system for nucleic acid sequencing comprising: a substrate having at least one nanopore extending therethrough, having an opening on the top and on the bottom of the substrate, and having a single polymerase enzyme attached proximal to the to opening of the at least one nanopore, the polymerase enzyme complexed with a primed template nucleic acid; a sequencing reaction mixture in contact with the substrate comprising reagents required for polymerase mediated nucleic acid synthesis including one or more nucleotide analogs, each comprising a current blockade label; drive electrodes in contact with the reaction mixture on either side of the substrate for producing a voltage drop across the at least one nanopore; one or more measurement electrodes connected to electronic measurement equipment for measuring the current through the nanopore over time; and a computer for identifying the type of nucleotide incorporated into the growing strand.

The measurement of current can be accomplished with one, two, three, or more electrodes. In the simplest case, a single electrode can measure a voltage drop relative to the drive electrodes in order to provide a measure of current. In other cases, multiple electrodes can be used in some cases to provide a more accurate determination of the current through the nanopore. Methods of measuring the current through nanopores in multiplex fashion is provided, for example, in U.S. patent application Ser. No. 12/757,789, filed Apr. 9, 2010, which is incorporated herein by reference for all purposes. The measurement, storage, and processing of current versus time data can be performed by electronic equipment that is well known in the art. In some cases, the equipment will need to provide accurate measurements of low levels of current over time.

Nanopores

The nanopores of the invention can be solid state nanopores, protein nanopores, or hybrid solid-state protein nanopores. The size of the nanopore depends on the type of measurement that is being performed. In some cases, small nanopores from about 1 nanometer to about 5 nanometers in diameter are used. In other applications, nanopores from about 2 nanometers to about 10 nanometers are used. Where current blockade groups as described herein are used, in some cases pores from about 1 nanometer to about 10 nanometers can be used, and in some cases, where larger blockade groups are used larger pores, for example from about 5 nanometers to about 40 nanometers can be used.

Two approaches are often used for nanopore polymer (DNA) sequencing: the first uses a protein nanopore (e.g. alpha-hemolysin, or MspA) embedded in a lipid membrane, and the second uses a solid-state nanopore. Protein nanopores have the advantage that as biomolecule, they self-assemble and are all identical to one another. In addition, it is possible to genetically engineer them to confer desired attributes or to create a fusion protein (e.g. an exonuclease+alpha-hemolysin). On the other hand, solid state nanopores have the advantage that they are more robust and stable compared to a protein embedded in a lipid membrane. Furthermore, solid state nanopores can in some cases be multiplexed and batch fabricated in an efficient and cost-effective manner. Finally, they might be combined with micro-electronic fabrication technology.

One aspect of the invention comprises techniques for treating the surface of solid-state nanopores in order to either improve their sequencing performance or to enable the creation of an hybrid protein/solid-state nanopore. In such a hybrid, the solid-state pore acts a substrate with a hole for the protein nanopore, which would be positioned as a plug within the hole. The protein nanopore would perform the sensing of DNA molecules. This hybrid can the advantages of both types of nanopores: the possibility for batch fabrication, stability, compatibility with micro-electronics, and a population of identical sensing subunits. Unlike methods where a lipid layer much larger than the width of a protein nanopore is used, the hybrid nanopores are generally constructed such that the dimensions of the solid state pore are close to the dimensions of the protein nanopore. The solid state pore into which the protein nanopore is disposed is generally from about 20% larger to about three times larger than the diameter of the protein nanopore. In preferred embodiments the solid state pore is sized such that only one protein nanopore will associate with the solid state pore. An array of hybrid nanopores is generally constructed by first producing an array of solid state pores in a substrate, selectively functionalizing the nanopores for attachment of the protein nanopore, then coupling or conjugating the nanopore to the walls of the solid state pore using liker/spacer chemistry.

Figure 18:
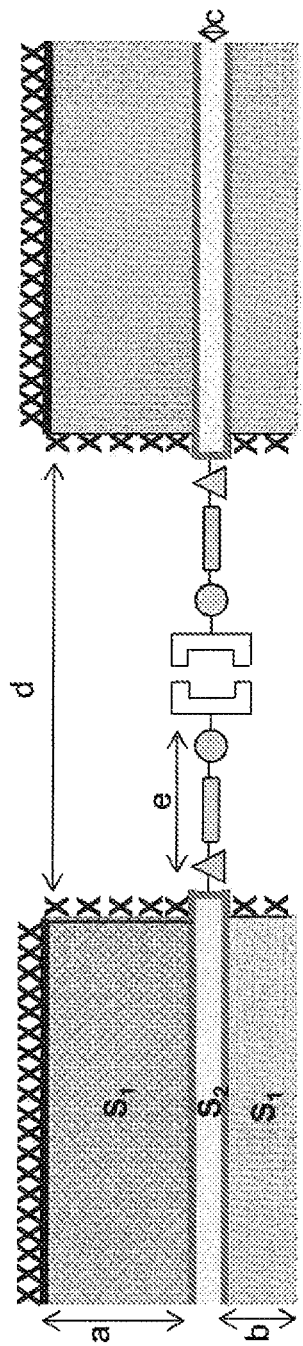
FIG. 18 illustrates chemistry that can be used to produce an array of hybrid nanopores.

FIG. 18 illustrates chemistry that can be used to produce an array of hybrid nanopores. The solid state pore can be constructed of one or multiple materials. In FIG. 18, two materials, S1 and S2 are used. In other cases, a single material can be used. Where two materials are used, for example, both the top and the bottom S1 layers can be fabricated using Al/AlOx, and S2 can comprise a gold layer. S2 can be used as a secondary material to facilitate controlled surface modification for attachment of the protein nanopore. This control would allow for more precise control over the position of an attached protein inside a nanopore. In one embodiment, phosphonate passivation chemistry specific towards S1-Aluminum is used, and thiol chemistry, specific to the gold portion of the sidewall, S2 is used. The thiol groups functionalizing S2 comprise pendant groups that attach to the linker/spacer which can be, for example, a protein or other biological molecule disposed at a controlled distance from the solid state pore sidewall and bottom/top. The size of the linker spacer molecule can be tailored to provide the appropriate spacing, for example by controlling molecular weight. By using organic molecules such as proteins, the spacers have enough flexibility to accommodate the different spacings which can result, for example from manufacturing variances in the size of the solid state pore. This control can be useful for controlling reagent diffusion in/out of the hybrid nanopores as well as spacing the protein to eliminate conformational restrictions and to potentially maximize signal to noise within a finite observation volume. The parameters can be controlled by adjusting the dimensions labeled as a, b, c, d, and e on the schematic illustration.

One aspect of the invention comprises devices and methods for obtaining a solid state pore sequencing device having a high portion of pores having only one nanopore per solid state pore. Protein nanopores embedded in a lipid membrane can suffer from the issue of Poisson-loading (loading of a single protein nanopore in each lipid membrane follows Poisson statistics), in this case only a single protein nanopore will fit into each solid-state nanopore. With the present invention, the pores can be made and functionalized such that one nanopore is generally present in one solid state pore.

One aspect of the invention comprises the use of surface monolayers on a solid state pore. In some embodiments, SiN substrates are treated using functional methoxy-, ethoxy-, or chloro-organosilane(s) such as —NHS terminated, —NH2 (amine) terminated, carboxylic acid terminated, epoxy terminated, maleimide terminated, isothiocyanate terminated, thiocyanate terminated, thiol terminated, meth(acrylate) terminated, azide, or biotin terminated. These functional groups for the non-specific immobilization of aHL or another protein. In some cases, S1 is functionalized to have only passive, inactive functional groups on the S1 surface. These functional groups can include polymeric chains at controlled length to prevent non-specific adsorption of biological species and reagents across the S1 surface. Some examples of these functional groups are PEG, fluorinated polymers, and other polymeric moieties at various molecular weights. This chemistry is schematically illustrated as (X) and typically provides a passive layer to prevent non-specific noise throughout the detection signal of the hybrid nanopore.

In some embodiments, SiOx substrates are treated using functional organosilane(s) such as —NHS terminated, —NH2 (amine) terminated, carboxylic acid terminated, epoxy terminated, maleimide terminated, isothiocyanate terminated, thiocyanate terminated, thiol terminated, meth(acrylate) terminated, azide, or biotin terminated. These functional groups are useful for non-specific immobilization of aHL or another protein. For specific control over location and conformation of such proteins inside a hybrid nanopore, S1 can be functionalized to have only passive, inactive functional groups on the S1 surface. These functional groups may include polymeric chains at controlled length to prevent non-specific adsorption of biological species and reagents across the S1 surface. Some examples of these functional groups are PEG, fluorinated polymers, and other polymeric moieties at various molecular weights. This chemistry is schematically illustrated as (X) and typically provides a passive layer to prevent non-specific noise throughout the detection signal of the hybrid nanopore.

In some embodiments, ALD alumina (as substrate) is modified using phosphonate chemistry. This includes phosphate, sulfonate, and silane chemistries since they all have weak affinities towards AlOx surfaces as well. The phosphonates can have any of the above chemistries on the terminus for surface treatment.

Where gold is the substrate, the invention comprises the use of functionalized thiol chemistries. The S2 layer is positioned to control the depth as which the protein or biological of choice is immobilized within the hybrid nanopore. The distance e in the figure controls the spacing of the linker/spacer such as a protein within the hybrid nanopore. The size of the liker/spacer can be adjusted by selecting the appropriate polymeric or rigid chemical spacer length of the linker between S2 and the protein attachment point. For example, this parameter can be controlled via the molecular weight and rigidity of the polymeric or non-polymeric linker chemistry used. Also, this can be controlled by the S2 electrode protrusion into hybrid nanopore. The linker chemistry used to attach alpha-HL or another protein to the hybrid nanopore sidewall substrate can consist of the pendant groups mentioned above, but may or may not also include a polymeric or rigid linker that further positions the protein into the center of the nanopore. This linker can distance can be controlled via control over the molecular weight and chemical composition of this linker. Some examples can include polypeptide linkers as well as PEG linkers.

The chemistries described above can be used as a conjugation mechanism for attachment of large molecule sensors such as proteins or quantum dots or functionalized viral templates or carbon nanotubes or DNA, if the nanopore is 10s-100s of nanometers in diameter. These large molecule sensors can be used to optically or electrochemically enhance detection via molecule-DNA interactions between H-bonds, charge, and in the case of optical detection via a FRET, quenching, or fluorescence detection event.

For example, if the nanopores are ~1 nm to 3 nm in diameter, the acid terminated silanes can be used to functionalize pores for better control over DNA translocation. Further, PEGylation with short PEGs may allow for passivation of pores to allow for ease of translocation.

In some embodiments, the invention provides surface chemistries for the attachment of proteins such as alpha-hemolysin to the solid state pore surface. Functional surface chemistries described above can be used to either A) conjugate protein via an engineered or available peptide residue to the nanopore surface, to anchor the protein or B) to functionalize the surface chemistry such that the hydrophilic region of that chemistry is presented to the surface to facilitate lipid bi-layer support. White et al., J. Am. Chem. Soc., 2007, 129 (38), 11766-11775, show this using cyano-functionalized surfaces, but any hydrophilic surface chemistry such as cyano-, amino-, or PEG terminated chemistries should support this function.

Specifically, the covalent conjugation of alpha hemolysin (or other proteins) to the surface of a solid state pore can be achieved via cystine or lysine residues in the protein structure. Further conjugation could be achieved via engineered peptide sequences in the protein structure or through CLIP or SNAP (Covalys) chemistries that are specific to one and only one residue engineered onto the protein structure. In more detail, protein lysine residues can be conjugated to NHS-containing chemistries, cystine residues to maleimide containing surface chemistries or SNAP to benzyl guanine/SNAP tags introduced onto the protein and CLIP to benzyl cytosine tags introduced onto the protein of choice.

One aspect of the invention comprises controlled and uncontrolled polymerization approaches on pores. The synthesis of silane chemistries that involve silane monolayers consisting of a photocleavable/photoinitiatable group that can be used to graft polymers from the surfaces of nanopores is known. One example is from this literature is N,N(diethylamino)dithiocarbamoylbenzyl(trimethoxy)silane. While this work has been primarily conducted on derivatized SiOx surfaces (Metters et al) or derivatized polymeric surfaces (Anseth/Bowman et al), polymeric chains can potentially be grown from the sidewalls of nanopores to control diameter, functionality, DNA translocation speed, and passivation for optical and/or electrochemical detection platforms. The initiation kinetics can be slowed down using a chain transfer or radical termination agent such as a tetraethylthiuram disulfide or a thiol, to achieve potential for more precise chain lengths on the functionalized nanopore.

Uncontrollable grafting of polymers to the surface of nanopores could be achieved via polymerization of functional chains (in solution) that can be attached via conjugation through any of the silanes listed in above. This achieves the same functional nanopore via a "grafting to" approach instead of a "grafting from" approach.

The polymerization techniques described above can also be used to support lipid bi-layer formation for protein immobilization support or for direct covalent attachment of proteins to surfaces as discussed in Ib1-2. The interesting facet of grafting polymer chains to or from the surface of a nanopore is the ability to control pore diameter, function, mobility (diffusion of molecules through), by controlling molecular weight, density, length, or multifunctionality of these chains. This offers a more fine-tuned way to control bi-layer formation for aHL or methods for covalently attaching proteins with polymeric chains that can space the protein from sidewalls of the nanopore substrate.

If using a polymeric approach described above, poly (acrylic acid) PAA or additional charged polymeric chemistries like NIPAAM or other hydrogels can be used to functionalize nanopores to create an electro-osmotic flow valve that changes inner-diameter based off pH or directionality via charge potential. This approach can be useful for governing the rate at which DNA translocated through a modified solid state pore and also to reanalyze DNA multiple times.

The devices of this invention can use H-bond interactions between functionalized electrodes with phosphate groups on ssDNA passing through the nanopore as described by Lindsay et al.

As described above, the hybrid nanopores of the present invention are generally prepared such that only a single protein nanopore will associate with each solid state pore by appropriately sizing the solid state pore and by using linker/spacer chemistry of the appropriate dimensions. In some cases, the solid state pores can accommodate more than one protein nanopore, and other approaches are used to ensure that only one protein nanopore is loaded into one pore, hole, or aperture in the device. Both the hybrid nanopores described above and the other nanopores used herein can include the use of a lipid layer for supporting the protein nanopore and acting as a spacer within the solid state pore.

In some cases loading can be done at a concentration at which a Poisson distribution dictates that at most about 37% of the apertures will have a single nanopore. Measurements on the pores will reveal which of the pores in the array have a single protein nanopore, and only those are used for sequencing measurements. In some cases loadings of single protein nanopores higher than that obtained through Poisson statistics are desired.

In some cases, repeated loading at relatively low concentrations can be used in order improve fraction of single protein nanopores. Where each of the pores can be addressed independently with a drive voltage, each pore could be connected to a fluidic conduit that supplies protein nanopores at a low concentration to the solid state pores, where the each conduit has a valve which can be controlled to allow or shut of the flow of fluid. The current across the solid state pore is monitored while the flow of fluid is enabled. Measurement of current while loading a lipid bilayer has been shown, see, e.g. JACS, 127:6502-6503 (2005) and JACS 129:4701-4705 (2007). When a protein nanopore becomes associated with the nanopore, a characteristic current/voltage relationship will indicate that a single pore is in place. At the point that a protein nanopore is associated, the flow of the liquid is interrupted to prevent further protein nanopore additions. The system can additionally be constructed to apply an electrical pulse that will dislodge the protein nanopore from the solid state pore where the electronics indicates that more than one protein nanopore has been incorporated. Once the multiple protein nanopores are removed, the flow of protein nanopores to the solid state pore can be resumed until a single protein nanopore is detected. These systems can be automated using feedback to allow the concurrent loading of multiple wells in the array without active user intervention during the process.

In some cases, steric hindrance can be used to ensure that a single protein nanopore is loaded into a single solid state pore. For example each protein nanopore can be attached to a sizing moiety that the size of the protein nanopore and the sizing moiety is such that only one will fit into each solid state pore. The sizing moiety can comprise, for example, one or more of a bead, nanoparticle, dendrimers, polymer, or DNA molecule whose size is on the order of the region between the protein nanopore and the solid state pore. These methods can be used in combination with membranes such as lipid bilayers. In some cases, the sizing moieties are removed after loading and before measurement. Alternatively, in some cases, the sizing moieties can remain associated with the protein nanopores after loading. In some embodiments, multiple sizing moieties are employed. Where membranes such as lipid bilayers are employed, each protein nanopore can be functionalized with arms, e.g. dendrimers-like arms, each having a membrane inserting moiety at its end (for example a non-porous transmembrane protein). The membrane inserting moieties will prevent the association of a second protein nanopore complex from entering the bilayer.

Electrostatic repulsion can also be used in order to obtain single protein nanopore loadings. Each polymer nanopore can be attached to a bead, nanoparticle, dendrimers, polymer, or DNA molecule that is highly charged. The charged protein nanopore complex in the pore will repel other charged protein nanopore complexes. In some cases, the charged moieties are removed after loading and before measurement. Alternatively, in some cases, the charged moieties can remain associated with the protein nanopores after loading. Charged protein-nanopore complexes can also be used with the systems in which attachment of the protein nanopore into the pore is actively monitored. The charged moiety can be used to actively remove the protein nanopore from the solid state pore using an electric field.

Optical trapping can also be employed in order to obtain single protein nanopore loadings. Optical traps can be used to capture complexes comprising a bead and a single nanopore protein. The bead can then be positioned over the solid state pore and released. Multiple pores can be loaded by sequential loading using a single optical trap, or an array of optical traps can be used to load multiple pores concurrently. The bead size and the laser power of the optical trap can be chosen such that no more than one bead at a time can be captured in the optical trap. After loading the protein nanopore into the solid state pore, the bead can be cleaved and washed away.

The protein nanopore to be inserted can be wild type or genetically engineered. The protein nanopore can comprise a fusion protein with an exonuclease or can be chemically linked to an exonuclease for sequencing using an exonuclease as described herein. Where an exonuclease is attached, it may have a DNA molecule, such as a template DNA bound to it at the time of loading. This DNA molecule can act as a moiety to provide steric or electrostatic hindrance as described above.

Resistive Openings

The methods, devices, and systems of the invention can incorporate resistive openings as described in U.S. patent application Ser. No. 12/757,789 files Apr. 9, 2010. The resistive openings connect a reservoir of fluid in contact with the nanopore to a volume of fluid in contact with a drive electrode in a manner that creates a resistive drop across the resistive opening, but allows for fluidic connection and for ion transport between the reservoir of fluid in contact with the nanopore and the volume of fluid in contact with the drive electrode.

The resistive opening can be made from any suitable structure that provides for a resistive drop across two fluid regions while allowing for the passage of fluid including ions between the fluid regions. In general, the resistive opening will impede, but not prevent the flow of ions. The resistive opening can comprise, for example, one or more narrow holes, apertures, or conduits. The resistive opening can comprise a porous or fibrous structure such as a nanoporous or nanofiber material. The resistive opening can comprise a single, or multiple, long, narrow channels. Such channels can be formed, for example, in a polymeric material such as polydimethylsiloxane (PDMS).

The incorporation of resistive openings into these structures can assist in facilitating the use of a single drive electrode for multiple nanopores (a constriction architecture). The incorporation of resistive openings associated with each nanopore can be useful for multiplexing and miniaturizing a system for nanopore DNA sequencing, providing for the use of a single drive electrode to provide the applied potential for each of the in-parallel nanopores. The use of a single set of drive electrodes can be advantageous because it simplifies the electronics and enables one to place the drive electrode away from the individual pores so that bubble-formation due to electrolysis at the electrode will not disrupt the nanopore or supporting lipid bilayer, and such that chemical species generated at the drive electrodes, for example acids, bases, oxidizing, and reducing species do not interfere with the sequencing measurements. With one set of drive electrodes, each nanopore generally requires one or more measurement electrodes. However, with one set of drive electrodes, there can be cross-talk between adjacent nanopores. For example, at any given moment, some pores will be open and others will be closed. This can result in statistical fluctuation of the resistance across the total circuit over time, which can lead to errors in determining polymer sequence.

In some aspects of this invention, a single drive voltage source can used for all the nanopores, and each nanopore is protected by a constriction (resistive opening). In some cases, there is a constriction, or resistive opening only above or only below the nanopore. In some cases there is a constriction, or resistive opening both above and below the nanopore. The resistive openings create a resistance drop between the fluid regions that they span. The resistance drop across a resistive opening is generally on the same order as the resistance drop across the nanopore and is generally equal to or lower than the resistive drop across the nanopore. In some cases the resistance drop across the resistive opening is about 1 K-ohm to about 100 G-ohm, from about 10 M-ohm to about 1 G-ohm, or from about 1 M-ohm to about 10 G-ohm. In some cases, the resistance drop is about the same as the resistance drop across an unblocked pore. In some cases, the resistance drop across the resistive opening is lower by a factor of greater than about 5, 10, 20, 50 or 100 relative to the resistance across an unblocked pore. In other cases, the resistance drop across the resistive opening is higher by a factor greater than about 5, 10, 20, 50 or 100 relative to the resistance across an unblocked pore.

In some aspects, the invention relates to devices and methods which allow for multiplex electronic sequencing measurements in a manner that reduces or eliminates cross-talk between the nanopores in the nanopore array. In some cases it is desirable for a nanopore sequencing measurement system to have a pair of drive electrodes that drive current through the nanopores, and one or more measurement electrodes that measure the current through the nanopore. It can be desirable to have the drive electrodes drive current through multiple nanopores in the nanopore array, and have measurement electrodes that are directly associated with each nanopore. We have found that this type of system can be obtained by the incorporation of resistive openings, which connect a reservoir of fluid in contact with the nanopore to a volume of fluid in contact with a drive electrode in a manner that creates a resistive drop across the resistive opening, but allows for fluidic connection and for ion transport between the reservoir of fluid in contact with the nanopore and the volume of fluid in contact with the drive electrode.

These resistive openings can be optimized for several type of operating conditions. For example, in some embodiments it is convenient for the resistive opening to act as a reference resistor, and in some cases it is desirable to have this resistance be well balanced with the sequencing nanopore resistance. One means of attaining this is for the resistive opening to comprise an additional nanopore identical to the sequencing nanopore. In this way the balance between the reference resistive opening and the sequencing nanopore is automatically balanced. In other embodiments it is desirable to minimize the stray series capacitance of the system, and in these cases a low capacitance can be achieved by increasing the thickness of the membrane or by decreasing the cross-sectional area of the aperture of the resistive opening. In some embodiments this membrane could be 2 times the thickness of the sequencing nanopore membrane, in still others, it could be 10, 30, 100, 300, 1000, 3000 or 10000 times thicker than the sequencing membrane. It is also of interest that the reference resistive opening be fabricated in a membrane that has a small surface area, as capacitance is typically proportional to surface area. In some embodiments, the reference resistive opening is 10 microns in diameter, in others it is 3 microns in diameter, in others it is 1 micron in diameter. In others there is no membrane and only a resistive opening in an otherwise solid structure.

The above description is intended to be illustrative and not restrictive. It readily should be apparent to one skilled in the art that various embodiments and-modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

Reversible Isolation of Nanopores

When performing measurements with arrays of nanopores, we have found that it can be useful to have the ability to fluidically address all, or a subset of the nanopores together in some aspects of the process, but to be able to individually isolate the nanopores for other parts of the process. For example, it may be desired to load in a nucleic acid sample such as a fragmented nucleic acid library onto all of the nanopores on a substrate or subset of those nanopores, yet when performing the analysis each of the nanopores is fluidically isolated from the other nanopores to prevent cross-talk and diffusion between different nanopores. In addition, it can then be useful to access all of the pores simultaneously to wash out the sample in order to introduce a subsequent sample. One aspect of the invention comprises a substrate for performing nanopore analysis that is configured such that the user can reversibly fluidically address all of the nanopores simultaneously, and also configured such that analysis can be performed wherein each of the nanopores is fluidically separated from the other nanopores.

Figure 19:
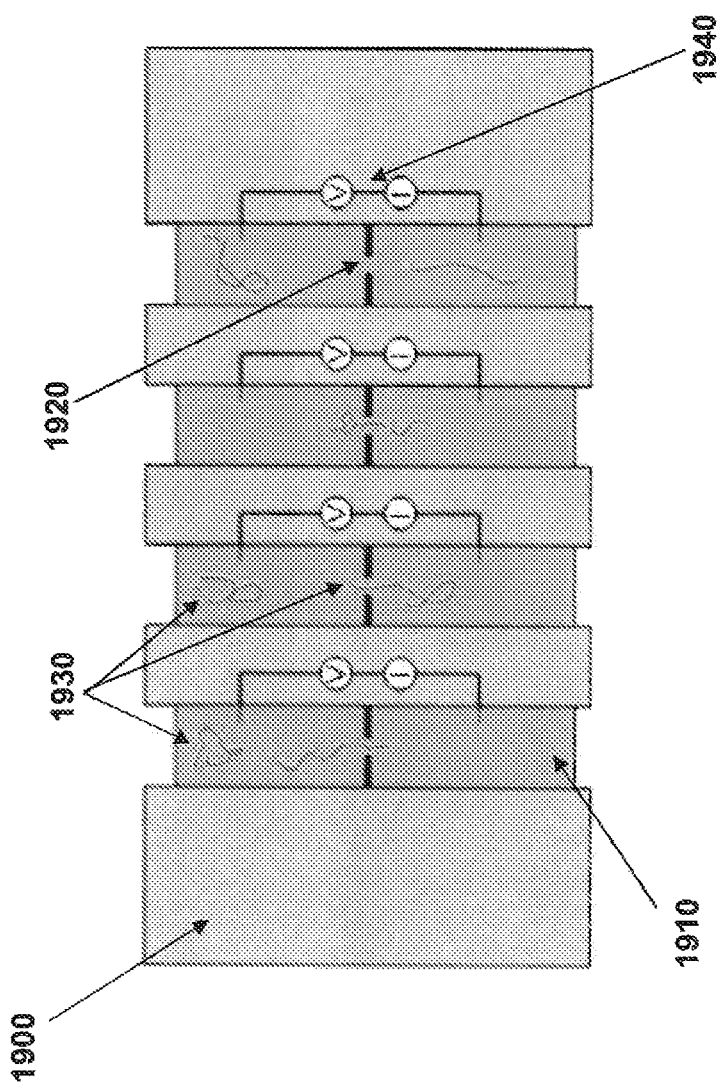
FIG. 19 is a schematic diagram showing an embodiment of the invention having fluidically separated chambers, each comprising a nanopore and circuitry for driving molecules through the pore and for measuring the current through the pore.

FIG. 19 shows an embodiment of the invention. The device has a substrate 1900 into which a series of fluidic chambers 1910 are disposed. Within each of these fluidic chambers is a nanopore 1920 as described in more detail herein. Each of the fluidic chambers has electronic circuitry 1940 for both applying a drive voltage across the nanopore, and for measuring the current through the nanopore.

For the device shown in FIG. 19, a fluidic sample can be applied across all of the nanopores in the sample, for example by flooding the top of the device with the fluid sample. After loading the sample onto the device in this manner, the level of the sample is allowed to drop to the point where each fluidic chamber 1910 is fluidically isolated from each other fluidic chamber. The level of the fluid can be lowered, for example, by removal of fluid from the top of the device, from flow of the fluid into the chambers, from flow of fluid out of the bottom of the chambers, and/or from evaporation.

Once the fluid containing sample is in each chamber, voltage is applied across the nanopore to drive the molecules in the sample 1930, such as nucleic acids, into the nanopores while measuring the current through the nanopore. As described in more detail herein, the modulation in current due to the passage of the molecules through the nanopore or the blockage of the nanopore by blockade groups can be used in order to obtain information about the molecules such as sequence information.

The illustration in FIG. 19 shows a portion of a device comprising four fluidic chambers. The devices of the invention can have any number of fluidic chambers, but will typically have about 1,000 to about 1.000,000 chambers. In some cases all of the chambers in the device will be accessible to a single sample fluid. In other cases, portions of the device will have subsets of chambers, each subset accessible to a different sample fluid. In this manner, the simultaneous analysis of multiple fluid samples can be carried out, each sample analyzed at multiple nanopores. The number of nanopores for the measurement of each sample for each sub-region of the device can be, for example, from about 100 to about 100,000 or more nanopores. These subsets of fluidic chambers can be separated by barriers constructed onto the top of the substrate, or by other suitable means, such as by surface tension, for example producing hydrophobic barriers.

In FIG. 19, the electronic circuit for applying drive voltage and for measuring current through the nanopore is shown as being part of the same circuit. It is to be understood that the application of voltage and measurement of current can be done with the same or with a separate set of electrodes, and can be carried out by methods understood in the art. These can be performed, for example by 2, 3, or 4 point measurements.

The portions of the device which come in contact with fluids can have surface chemistry applied in order to control the wetting and filling of the fluids. The nanopores can comprise any suitable nanopore structure for analysis of sample molecule including the solid state nanopores, biologically derived nanopores, and hybrid nanopores.

For the devices and methods of this aspect of the invention, the fluidic chambers comprising the nanopores can be fluidically separated by a variety of methods. The method of separation must be reversible, such that during the filling of the chambers with sample, all or a subset of the chambers are accessible to the fluid sample, and during the analysis of the sample by passing the sample through the nanopore, the fluidic chambers are each fluidically separated from each other fluidic chamber. In some embodiments, the reversible separation can be performed using a gasket that is reversibly contacted with one or both of the top and bottom of the fluidic chambers.

Figure 20:
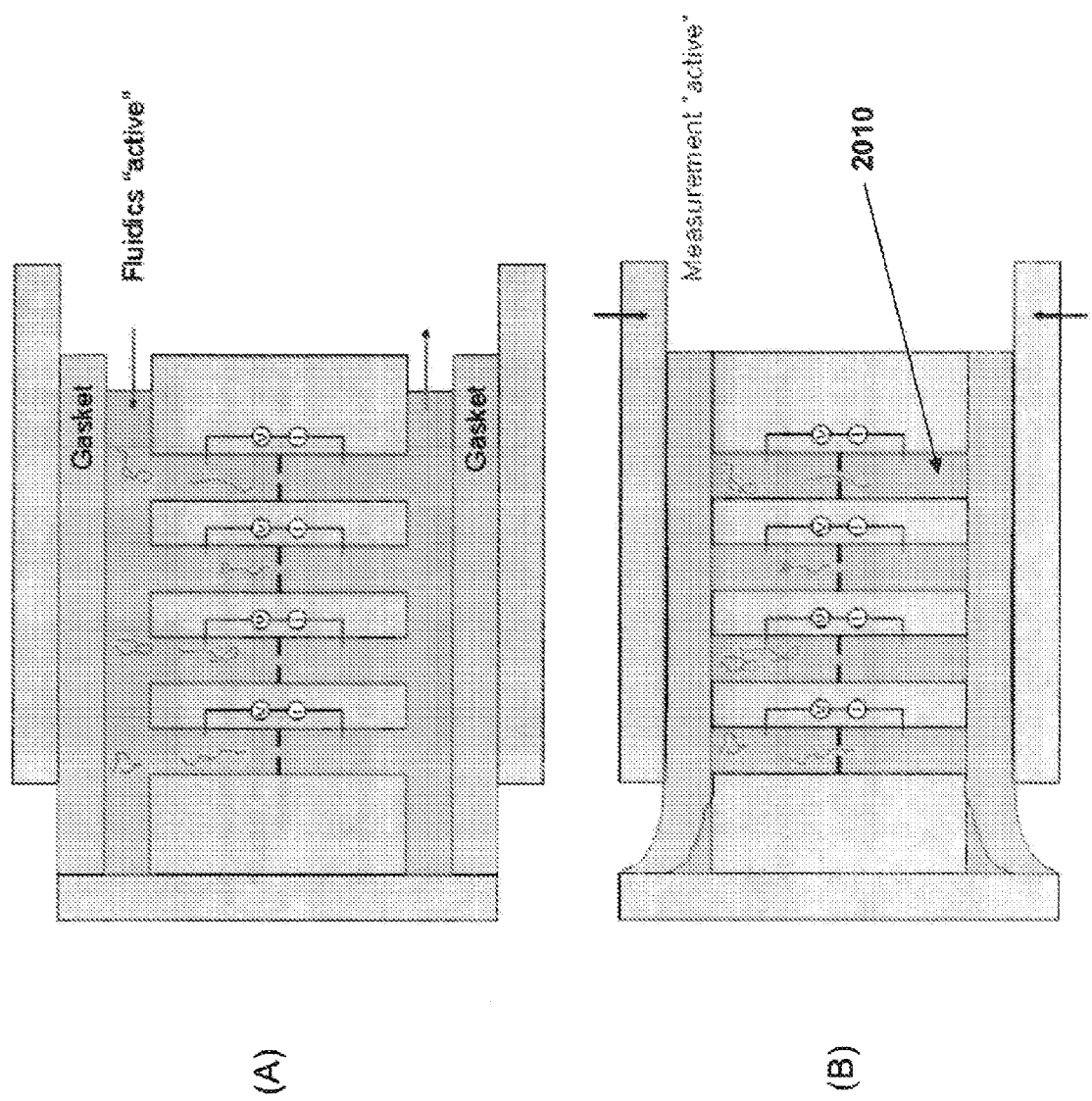
FIG. 20 is a schematic diagram illustrating an embodiment of the invention wherein device comprises a gasket that can be reversibly engaged to fluidically isolate the fluidic chambers.

FIG. 20 illustrates an embodiment of a device having a gasket that reversibly closes and isolates the chambers, allowing filling of the chambers when the gasket is in one position, and allowing for analysis within fluidically separated chambers in a second position. The device comprises a top gasket above the chambers and a bottom gasket below the chambers. In FIG. 20, the device is in the open position wherein the fluidics are active. In this position, the top and bottom gasket are spaced away from the top and bottom surface of the device allowing fluid flow to all of the fluidic chambers. For example, the fluid can be dispensed from the top surface of the device, underneath the top gasket into each of the chambers. The filling of the chambers can also include filling from the bottom of the chambers, above the bottom gasket. For example, in some cases fluid having molecules of interest can be introduced from above, while fluid of generally the same composition but without the sample molecules can be added from below. In other cases, fluid sample comprising molecules to be analyzed can be added from the top, and filling of the bottom portion can occur by flow through the nanopore.

Once the sample has been added to the device, the top and bottom gaskets are brought into contact with top and bottom of the fluidic chambers. The gaskets provide a seal which fluidically isolates each of the chambers 2010, preventing cross-talk between the chambers during the analysis. The gaskets can be pressed against the tops and bottoms of the chambers using rigid pads which push the gasket onto the substrate. The gaskets are generally made from an elastomeric material, for example a rubber or silicone material, e.g.

polydimethylsiloxane. In some cases a hydrophobic gel can be used. As the gaskets are driven onto the substrate, the intervening fluid is driven out of the space between the gaskets and the substrate.

In some aspects, the invention provides a device for analysis of single molecules in nanopores comprising a substrate comprising a plurality of nanopores. Each of the nanopores is disposed within a chamber and each chamber has 1) drive electrodes for driving single molecules from the sample through the nanopores, and 2) electrodes capable of measuring current through the nanopore. The device has at least two configurations. In one configuration, the plurality of nanopores are simultaneously accessible to a fluidic sample for loading the sample. In a second configuration, the device is configured such that the nanopores are each fluidically isolated from one another during analysis.

One way in which a device of the invention can be constructed is to provide a top gasket above the substrate and a bottom gasket below the substrate, the top and bottom gaskets configured such that each gasket is spaced away from the substrate while the sample is loaded, and configured such that each gasket is held against the substrate during analysis to isolate the nanopores from one another.

The invention also includes methods of performing multiple parallel nanopore analyses, wherein each of the nanopores in a substrate is within a fluidic chamber that can be reversibly isolated from the other fluidic chambers. In one aspect, the invention provides a method for analyzing single molecules in nanopores comprising: providing a device having a loading configuration and an analysis configuration. The device includes a substrate that has a plurality of nanopores, each nanopore disposed within a chamber. Each chamber has drive electrodes for driving single molecules from the sample through the plurality of nanopores, and each has comprises electrodes for measuring current through the nanopore. The fluidic sample is loaded onto the substrate when the device is in the loading configuration whereby the plurality of nanopores are simultaneously accessible to the fluidic sample. The plurality of nanopores can be all of the nanopores on the substrate or a subset of such nanopores. In some cases, several subsets are each accessible to a different fluid sample. When the device is in the analysis configuration, the sample is analyzed by: fluidically isolating each of the plurality of nanopores from one another; providing drive voltages across each of the fluidically isolated nanopores with the drive electrodes; and measuring the current through the nanopores to characterize the single molecules in the fluidic sample. By fluidically isolating each of the nanopores an improved signal is obtained by eliminating cross-talk between the nanopores.

The method can include using a device having a top gasket above the substrate and a bottom gasket below the substrate, spacing the top and bottom gaskets away from the substrate in the loading configuration, and mating each gasket with the substrate while the device is in the analysis configuration to isolate the chambers comprising the nanopores from one another.

Fabrication methods and structures described in copending U.S. patent application Ser. No. 13/031,122 filed Dec. 18, 2011, U.S. patent application Ser. No. 13/031,103, filed Dec. 18, 2011, and U.S. patent application Ser. No. 13/031,146, filed Dec. 18, 2011 can be used where suitable to produce the devices and systems described herein. These applications are incorporated by reference herein in their entirety.

Resistance Barcoding of Nucleic Acids for Nanopore Sequencing

In some aspects of the invention, the sequence of a nucleic acid is determined by monitoring the change in resistance as a nucleic acid strand passes through a nanopore. Generally, an electric field is applied to drive the nucleic acid strand through the pore while the resistance or current through the pore is monitored over time. Since each of the bases in the nucleic acid strand is different, the current flow as each base traverses through the pore can provide information about the identity of the base. In some cases, in addition to signal differences for different bases, differences in signal can be obtained based on the sequence context in which the base resides. Methods for using neighboring and nearby bases in order to assist in calling a base in nanopore sequencing are described in copending U.S. patent application Ser. No. 12/757,789, filed Apr. 9, 2010, which is incorporated herein by reference for all purposes.

In some cases, the difference in the resistance for bases in a nucleic acid chain can be increased by modifying the base with a functional group. We refer, herein to groups which modify the resistance or conductivity through the pore as resistance labels. In some cases, all four bases are modified in order increase the difference in resistance between the bases to more readily call the base. In other cases, 3, 2 or 1 of the bases can be modified. In some cases, the modification that modifies the current in the nanopore will code for more than one base. For example, in some cases, a different resistance label is applied for a given sub-sequence in the nucleic acid. For these systems, more than 4 different resistance labels can be employed, for example up to 10, or up to 100 resistance labels, each corresponding to a different sub-sequence can be employed. The sub-sequences can be, for example from about 2 bases to about 20 bases in length.

Figure 21:
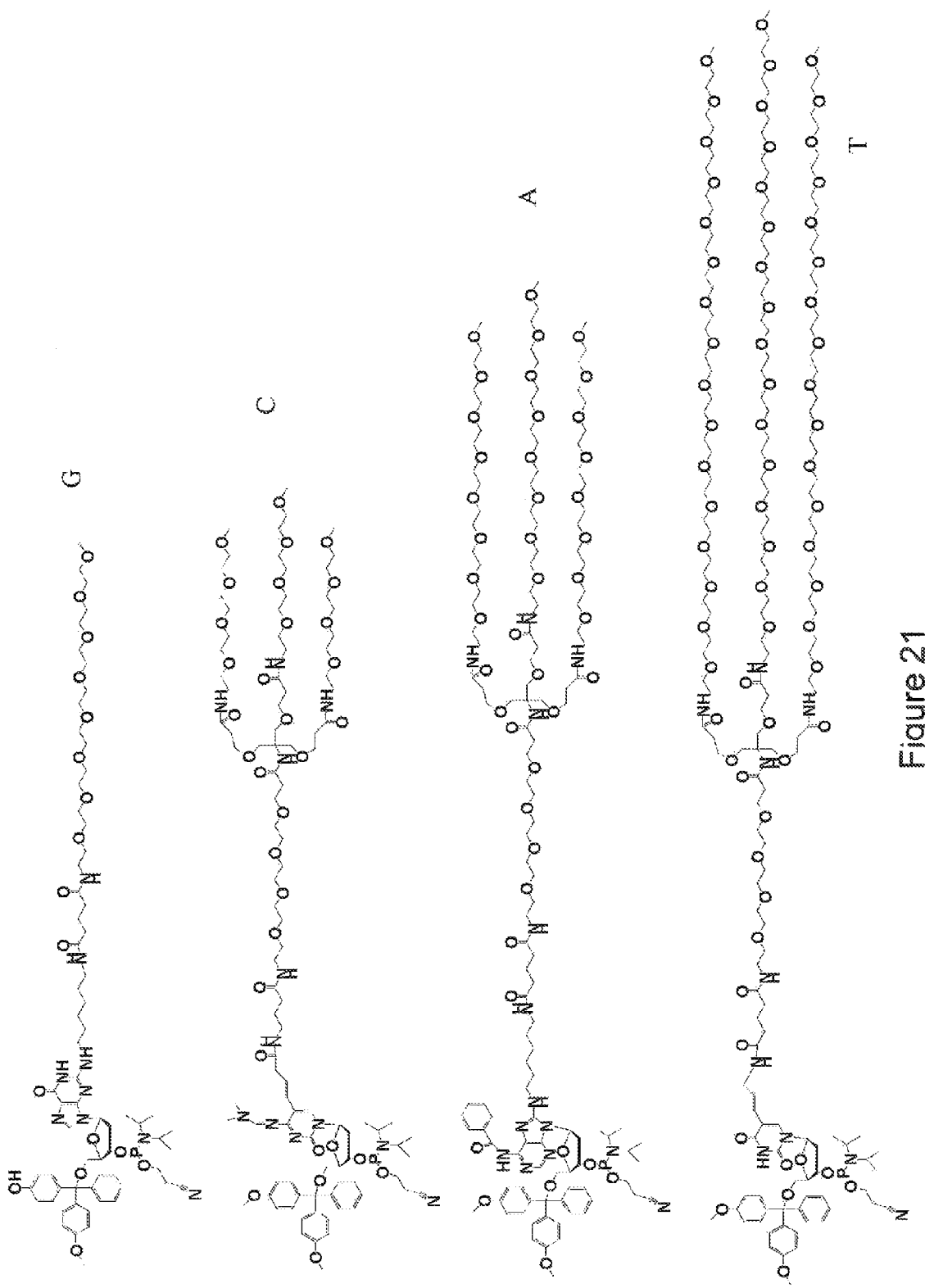
FIG. 21 shows a set of nucleotide analogs, each carrying a different blockade label.

A nucleic acid having resistance labels can be made by well known organic synthetic methods. The nucleic acid can be synthesized by using phosphoramidite building blocks to produce a nucleic acid of the desired sequence having the appropriate resistance labels. Synthesis of oligonucleotides using phosphoramidites is well known and can be routinely carried out using automated equipment. FIG. 21 shows a set of resistance labels attached to phosphoramidites. The labels for each of the bases G, C, A, T each have a different amounts of ethylene glycol ($-OCH_2CH_2-$) linkages. Generally, the higher number of ethylene glycol linkages, the larger the cross-sectional area taken up by the resistance label, and the more resistance observed. In one aspect, the invention provides a nucleotide strand such as DNA wherein each of the bases has attached thereto a different resistance label, each resistance label having a different number of ethylene glycol linkages. The amount of branching can also be used to control the structure of the resistance label to control the resistance.

Figure 22:
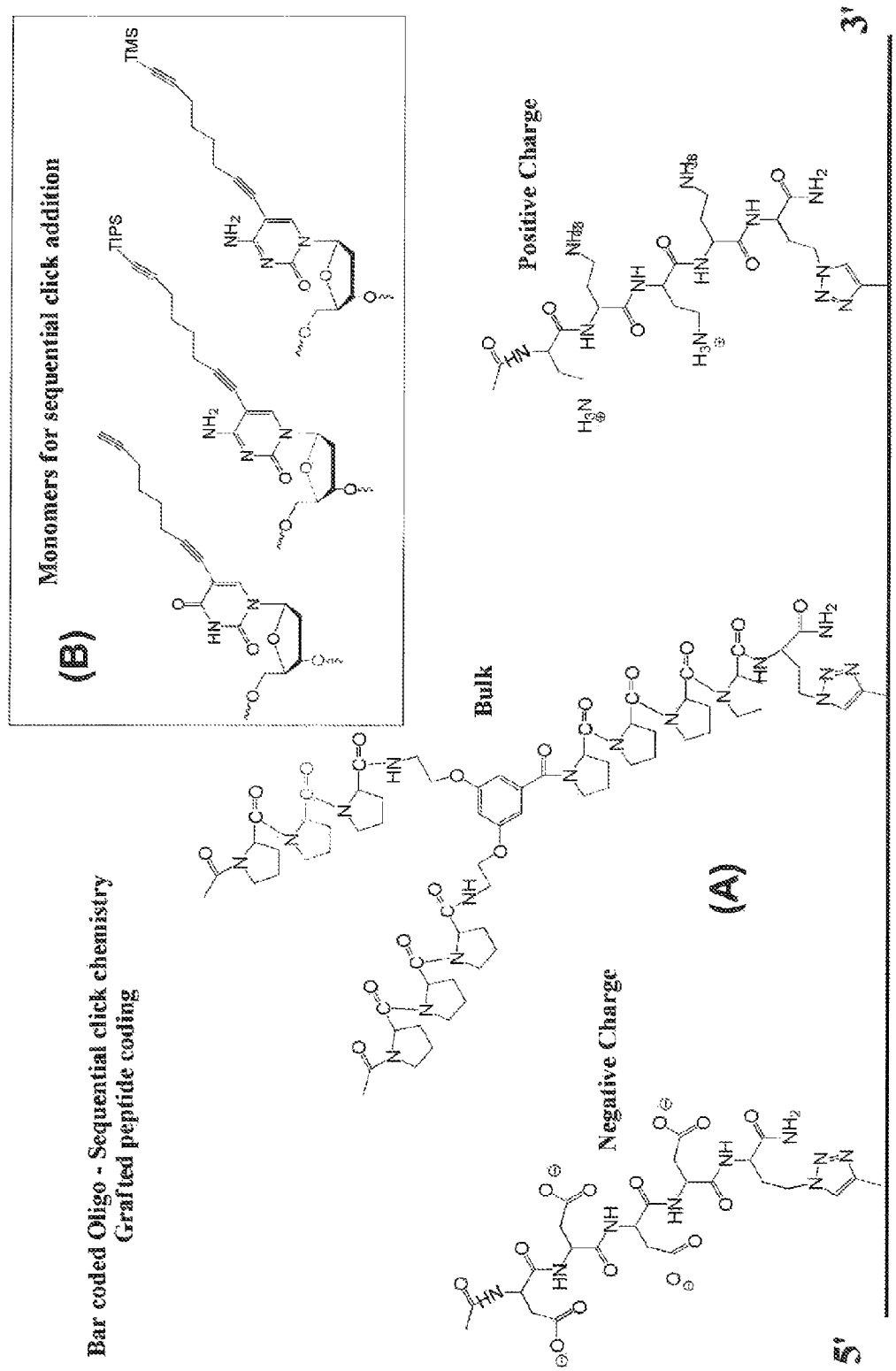
FIG. 22 (A) shows resistance labels having negative, neutral (bulk), and positive net charge.

In some aspects of the invention, the resistance labels increase the cross-sectional area of the nucleotide in a sequence specific manner. It is generally desired that the functional groups on the nucleotides do not decrease the water solubility of the nucleic acid, e.g. DNA. In some cases, it is desired that the resistance labels be made of non-ionic functional groups so as not to significantly change the charge of the nucleic acid. For example, for these resistance labels, groups such as ethers, esters, or amides can be used along with aliphatic hydrocarbons comprising either linear or branched $CH$, $CH_2$, or $CH_3$ groups. In some cases, the resistance labels will have negative or positive charge groups. Acetate, sulfate, sulfonate, phosphate, and phosphonate groups can be used to produce resistance labels having anionic groups. Amine groups can be used to produce resistance labels having positive charges. In some cases, the resistance label will have a single charge, in other cases, the resistance label will have multiple charges, for example from about 2 to about 20, or from about 2 to about 10 charges. In some cases the resistance label will have both positively and negatively charged groups. FIG. 22(A) shows examples of resistance labels having positive, neutral, and negatively charged groups.

Resistance labels can be added to a formed nucleic acid strand. One way to add the resistance labels uses click chemistry, for example using a copper catalyzed azide alkyne cycloaddition. FIG. 22(B) shows monomers that could be used for sequential click chemistry addition. See for example BaseClick GMBH. The TMS and TIPS groups act as protecting groups, allowing for selective cycloaddition first to the unprotected alkyne group, followed by deprotection of one of the protecting groups, exposing the next alkyne for click reaction, followed by deprotection and functionalization of the last alkyne. Use of other protecting groups can extend this set of modifications to a $4^{th}$ base, or the $4^{th}$ base can be left without having a resistance label, as its resistance would be distinguishable from the other three labeled bases.

Figure 23:
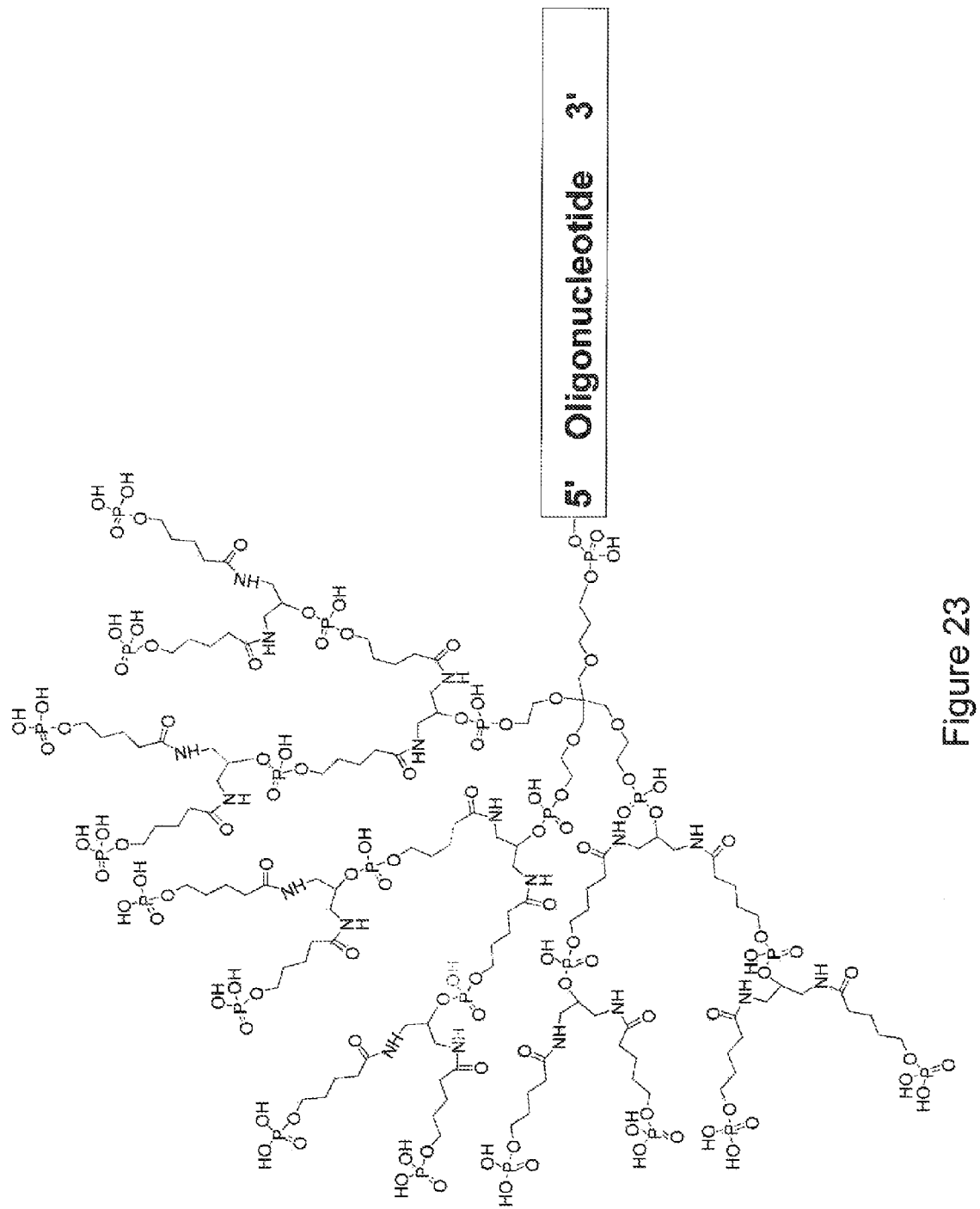
FIG. 23 shows a resistance label having a dendritic structure

Dendritic structures can also be employed in order to produce blockade labels. The number of branches, length of the branches, and type of functionality can be used to produce sets of dendrimers for use as resistance labels. FIG. 23 shows an example of a dendrimeric molecule that can be used as a resistance label. The label can be added to a 5' end of an oligo using automated nucleic acid synthesis. Here the terminal groups are phosphates, but other suitable terminal groups can be employed.

Labels can be attached to the nucleic acid at any suitable position, for example to the ribose, the phosphate, or the base.

The size of the resistance labels is selected to be compatible with the type of nanopore which is being used to sequence. For example, where an alpha hemolysin type nanopore is used, relatively small resistance labels are used. Where a solid state nanopore is used, larger resistance labels can be employed, and the size of the pore can be tailored to optimize the size and selectivity of the signal.

In some aspects the invention provides a method for sequencing comprising providing a nanopore; exposing to one side of the nanopore a solution comprising a nucleic acid strand labeled on at least one type of base with a resistance label; applying a voltage across the nanopore to cause the nucleic acid strand to be transmitted through the nanopore; measuring the current through the nanopore as a function of time as the nucleic acid transits the nanopore; and using the measured current as a function of time to identify the base labeled with the resistance label.

The method is typically carried out where the nucleic acid strand has 4 types of bases, 3 or more of the types of bases each having a different resistance label. The measured current as a function of time is then used to obtain sequence information about the nucleic acid strand by identifying four types of bases. In some cases the sequence can be determined as each of the resistance labels displays a different level of current as it is transiting the nanopore. The context of the sequence surrounding the specific base can also be used for identification.

Where three or more different resistance labels are used, in some cases, the different resistance labels each have a different number of ethylene glycol units.

In some cases, proteins that remove the secondary structure of the nucleic acid molecule to be sequenced are used. For example, helicases or topoisomerases can be added to remove secondary structure in order to provide a more consistent transport rate of the nucleic acid through the nanopore.

Combined Low Resolution and High Resolution Nanopore Sequencing

In some cases, it is known that a polymerase that is located near a pore can be used to control the rate of translation of a single stranded nucleic acid through a nanopore. See e.g. U.S. patent application Ser. No. 12/757,789, filed Apr. 9, 2010. While this provides for more accurate sequencing, it can be slower than sequencing in which a potential is used to drive the nucleic acid through the pore. One aspect of the invention is a method for sequencing a single stranded template nucleic acid with a nanopore wherein two sequencing regimes are used with respect to the same template nucleic acid. In one mode, the enzyme is used to drive the translation of the nucleic acid through the pore. This is done with a low voltage or no voltage across the pore. In a second mode, the voltage is raised, allowing for more rapid movement of the nucleic acid through the pore, providing for faster, but lower accuracy sequencing. The two modes can be used for moving along the nucleic acid to the regions of most interest, then spending the time to sequence those regions with more accuracy. The mode can be switched as many times as is suitable for obtaining the best balance of accuracy and throughput. In some cases the mode is switched 1, 2, 3, 4, 5, 6, 7, 8, 9, or 10 times. In some cases the mode is switched from 1 to 100 or more times. The switching of modes can either be done in real time with the intervention of an individual, or can be preprogrammed and carried out automatically based on the sequence context.

Thus, in one aspect of the invention, switching between voltage driven and polymerase-mediated translocation in a single nanopore provide is used for targeted sequencing. In particular, it is known in the art that a transition between polymerase mediated and voltage driven nanopore translocation can be achieved by increasing the voltage on the nanopore to a "dissociation level" such that the polymerase is no longer able to remain bound under the force applied by the voltage. At this point, the polymerase dissociates and the DNA molecule begins unrestricted threading through the nanopore. It has also been shown in the art that an opposite transition is also possible: if the voltage is reduced to a "rebinding level" which, in general, is different than the dissociation level, a new polymerase molecule will bind the DNA strand, and at a lower "polymerase-based readout level" the polymerase-mediated translocation readout can take place. With the ability, at will, to make transitions in both directions between the two modes, these two facilities can be combined to produce a convenient form of targeted sequencing. In this form, low-resolution mapping of chromosomal fragments is achieved using the fast unrestricted translocation of DNA fragments wherein the purine/pyrimidine content is visible even without single base resolution in such a way as to allow coarse level ascertainment of genome position. A feedback algorithm can be used to arrest the translocation drive voltage upon a determination that the strand of DNA presently has a region of interest correctly positioned for high resolution sequencing via polymerase mediated translocation. At this point, the "rebinding level" is applied to the pore and a polymerase re-binds the strand and high resolution sequencing commences. This is allowed to proceed until the region has been sequenced. At this point, the "dissociation level" is reapplied, and the strand can either be translocated to repeat sequencing of the same region of interest, or the above-mentioned procedure can be repeated to translocate to a new region of interest.

Hairpin Stopper Moiety

Additional aspects can be employed to assist in the application of this method. One issue is that genome fragments have finite size and will be subject to falling out of the pore when they reach the end. When this happens, re-loading is not difficult and the molecule is likely to be lost. To facilitate repeat reading of the molecules, a "stopper moiety" can be employed at one end to prevent the molecule from passing all the way through. This stopper can be attached to a fragment of genomic DNA using a variety of methods. One convenient method is to ligate universal adapters to one end of the molecule, said universal adapter being synthesized with a bulky side group. Methods are known in the art for attaching such side groups to either 3' or 5' DNA ends, or at positions interior to such an adapter sequence. These side groups can be attached covalently or non-covalently such as through the streptavidin-biotin interaction. The blocking group can be a hairpin of DNA with a self-complementary section that creates a section of double stranded DNA that will not pass through the nanopore. To allow blocking of both ends, means can be employed to cause a plug to form after the DNA molecule has threaded the nanopore. For example, universal adapters and ligase enzymes can be provided on the trans side of the nanopore solution so that once the molecule has threaded it is available for ligation. In one implementation a first universal adapter would be ligated to the "insertion end" of the DNA prior to application of the DNA to the nanopore. This sequence would allow a hybridization of a reverse-complement oligonucleotide to bind on the trans side. This double stranded region would serve as a stopper. This stopper would have the merit of being reversible in that a larger voltage can be applied and strip off the reverse complement oligonucleotide, allowing the pore to be re-used on a different DNA strand.

In another implementation, the universal adapter is used to allow targeted ligation of another strand. In this method, there is a splint oligo, and a ligation oligo that contains a blocking function (using any of the aforementioned blocking elements, including a hairpin sequence). The splint has a region that is complementary to the adapter on the trans-end of the DNA molecule and a region that is complementary to one end of the blocking oligo. The sequences are chosen such that the three elements form an appropriate substrate for one of the many DNA ligases. A ligase enzyme binds the site and joins the blocking oligo covalently with the trans end of the DNA strand.

Figure 24:
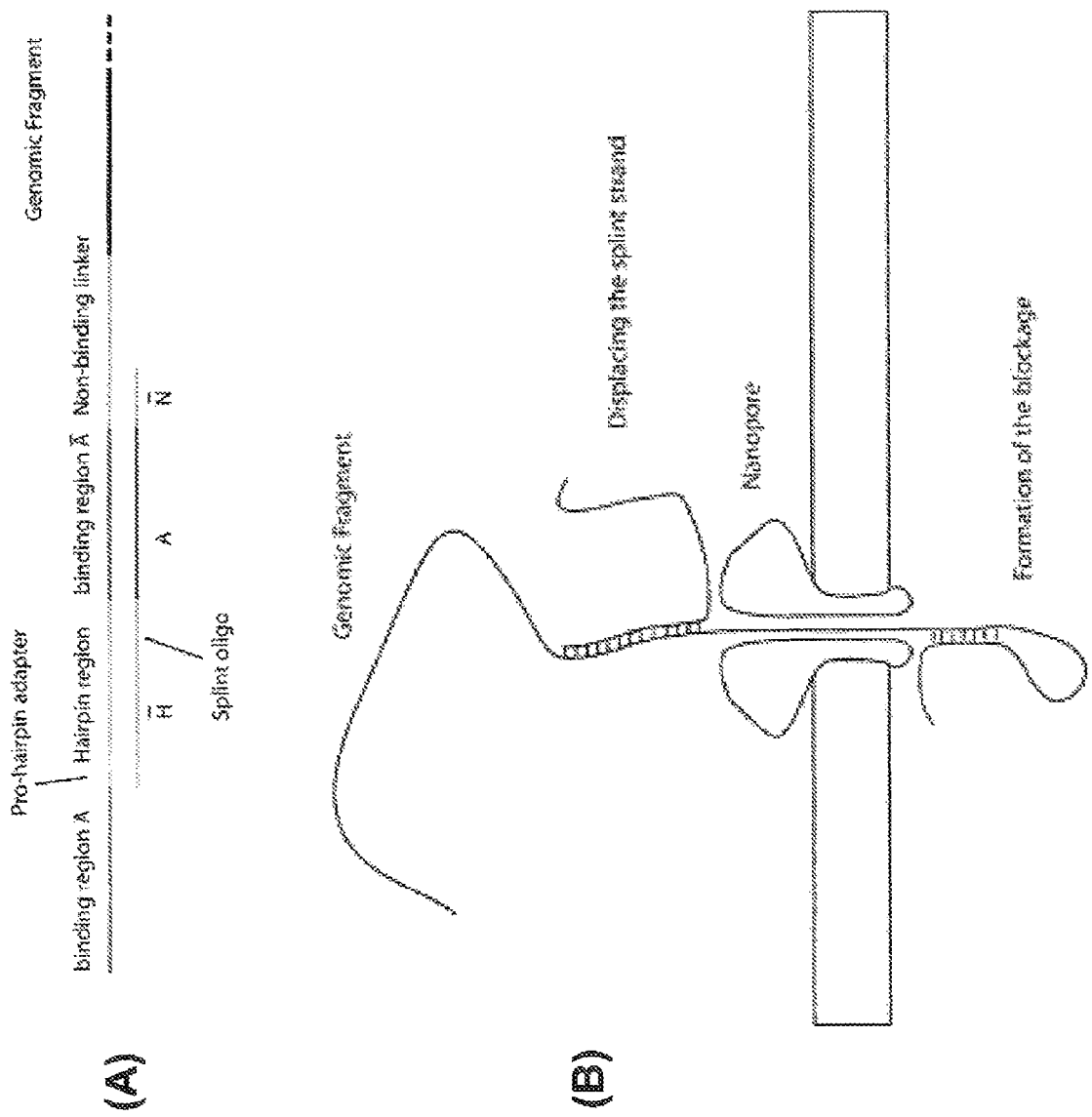
FIG. 24(A) shows an example of the structure of a template nucleic acid having a splint strand hybridized so as to prevent formation of the hairpin structure until its removal.
FIG. 24(B) shows how the hairpin forms on one side of the nanopore after the splint strand has been displaced, forming a blockage.

Another implementation allows that the trans-end blocker is triggered to form by the passage of the DNA through the pore. One implementation of this is to provide a hairpin sequence at the trans end that is held open by a splint oligo that leaves a small number of bases overhanging at the trans end to allow for insertion into the pore. The splint molecule would hybridize with the other half of the hairpin sequence, so the free end would not close into a hairpin. However, when the molecule is inserted into a nanopore, a strand-displacing voltage (known to those skilled in the art) is applied, the splint will be stripped off, and the normal hairpin structure will spontaneously form on the trans side of the pore, creating the blocking function. FIG. 24(A) shows an example of the structure of a template nucleic acid having a splint strand hybridized so as to prevent formation of the hairpin structure until its removal. FIG. 24(B) shows how the hairpin forms on one side of the nanopore after the splint strand has been displaced, forming a blockage.

In some aspects, the invention provides a nucleic acid template molecule for use in nanopore sequencing comprising: a partially double-stranded nucleic acid comprising a sample strand comprising a nucleic acid sequence of interest connected to an adaptor comprising a binding region A', a hairpin region H, and a binding region A that is complementary to binding region A, and a splint oligonucleotide strand hybridized to the sample strand comprising an H' region complementary to the hairpin region H, and a region A, complementary to binding region A' of the sample strand, whereby, when the splint oligonucleotides is removed from the sample strand, a hairpin region can be formed in the sample strand by the hybridization of binding regions A and A'.

In some embodiments the nucleic acid template further comprising a non-binding linker sequence N between binding region A' and the sequence of interest. In addition, the nucleotide can further comprising a sequence N' in the splint oligonucleotide complementary to at least a portion of the non-binding linker sequence N.

In some aspects, the invention provides methods for loading a sample nucleic acid into a nanopore comprising: providing a nanopore in contact with an upper fluid region and a lower fluid region, each of the fluid regions in electrical contact with one of a pair of drive electrodes, whereby the nanopore is of a size such that it a single-stranded nucleic acid can pass through the nanopore, but a double-stranded nucleic acid will not pass; adding to the upper fluidic region a partially double-stranded nucleic acid comprising: a sample strand comprising a nucleic acid sequence of interest connected to an adaptor comprising a binding region A, a hairpin region H, and a binding region A' that is complementary to binding region A, and a splint oligonucleotide strand hybridized to the sample strand comprising an H' region complementary to the hairpin region H, and a region A', complementary to binding region A of the sample strand; and providing a voltage across the drive electrodes whereby the sample strand translates through the nanopore, displacing the splint oligonucleotide, and whereby when the portion of the strand comprising the binding regions and hairpin regions translates through the pore, a hairpin region is formed in the sample strand by the hybridization of binding regions A and A'.

Improved Nucleic Acid Loading into Pores with Small, Flexible, Negatively Charged Polymers Another aspect of the invention provides methods to improve the loading of DNA molecules in nanopores, both solid state and protein-based (and hybrid). Because of the very small size of nanopores, there are significant barriers, both steric and entropic that work to prevent molecules from threading the nanopore. As a result, the concentration of DNA that is required to achieve a useful rate of threading is generally higher than would be desired. Here, a small, flexible, negatively charged polymer is attached either the 3' or 5' end of the single stranded template DNA. The polymers are covalently attached to a part of the part of the DNA chain close to the end. Preferably, the polymer is attached to the last base in the chain. In some cases, the attachment is to either the 3' or the 5' position of the terminal base. The charged moieties can formed from a variety of different compositions. In some cases, polyphosphates are used. Polyphosphates have the advantage that they are similar in composition to components of the DNA backbone. Other negatively charged polymers are suitable, including chains of amino acids that carry a negative charge under the conditions used for initiation, acrylic acid polymers, polysulfonates, dextran sulfate, organic polymers, and organometallic polymers. The polymer can have from about 3 to about 200 negative charges, or from about 4 to about 50 negative charges. Chemistry for attaching such polymers, e.g. to the 3' or 5' positions at the end of the oligonucleotide chain are well known in the art.

In addition to improving the loading of the nucleic acid molecules into the nanopores, the addition of the negatively charged caps to the nucleic acids provides for controlling which end of the nucleic acid first enters the nanopore, therefore controlling the direction of sequencing. In some cases, a negative cap is attached to the 3' end to provide 3'-5' sequencing. In some cases, a negative cap is attached to the 5' end to provide 5'-3' sequencing.

In some aspects, the invention provides a method for loading sample nucleic acids into a nanopore comprising: providing a single stranded nucleic acid, covalently attaching to either the 5' end or the 3' end a polymer comprised of monomeric units, each monomeric unit having a net negative charge to obtain a capped nucleic acid, adding the capped nucleic acid to the upper fluidic region of a nanopore analysis device, the nanopore analysis device comprising a nanopore disposed between an upper fluidic region and a lower fluidic region, and a pair of drive electrodes in electrical contact with the upper fluidic region and lower fluidic region, and providing a potential across the drive electrodes such that the negatively charged region of the capped nucleic acid is translated through the nanopore, thereby obtaining improved loading of the capped nucleic acid strand compared to loading a nucleic acid that was not capped.

Examples

Sequencing Using Blockade Labels

Into a microfluidic chip having a thin silicon nitride substrate having a hole about 100 nm in diameter is introduced a lipid bilayer membrane that spans the hole in the microfluidic chip, as described, for example in Reimhult, et al., Trends in Biotechnology, 26(2), 82-89, 2008. Above and below the membrane are disposed drive electrodes to provide a voltage drop across the membrane. A separate set of electrodes is provided above and below the membrane for measuring the resistance/current flow through the membrane. Into the membrane is introduced a modified alpha hemolysin pore having alkyne groups coupled to the portions of the pore extending into the solution. The alpha hemolysin pore is added at a concentration in which on average, one pore is added to the membrane. The presence of the pore in the membrane is determined using conductance measurements with the measuring electrodes. Into the top chamber of the microfluidic chip is added a solution of modified phi-29 polymerase enzyme complex where the enzyme comprises a linker attached to an azide functional group. The polymerase complex also has a DNA template hybridized to a primer. The solution also contains copper acetate at a concentration sufficient for catalyzing the coupling between the azide on the polymerase with the alkyne on the alpha hemolysin pore. The polymerase is added under conditions such that only one polymerase couples to the alpha hemolysin pore.

Into the top chamber of the microfluidic chip is added the reagents required for polymerase mediated synthesis of DNA including magnesium as the catalytic metal and including four nucleotide analogs, each having a different blockade label connected through the terminal phosphate of the nucleotide analog. The ion concentrations in the solutions above and below the membrane are controlled to allow both polymerase activity and the appropriate level background conduction through the nanopore. Each of the analogs has a structure shown in FIG. 15(C) where m=3, n=3, where each of the four analogs has a different number of positive charges on the charged monomer. A has one positive charge, C has two, G has three, and T has four. A bias is then produced across the membrane using the drive electrodes such that the bottom chamber has a negative bias, and nucleic acid synthesis is initiated.

The current is monitored across the pore as a function of time. When a non-cognate nucleotide analog is in the active site, the interaction will occur for only on the order of microseconds, resulting in short blockages of the pore. When a cognate nucleotide analog is in the active site, longer blockages of the pore are observed, on the order of milliseconds. The amount of blockage varies with the type of blockade group, allowing the identification of which nucleotide analog was incorporated. Once the incorporation occurs, the terminal phosphate/blockade label group is released, and generally is pulled through the pore into the bottom chamber. The characteristic signal upon release of the blockade label can provide additional information for identifying the nucleotide analog and for confirming that incorporation has occurred. The signal versus time is measured, then is imported into a computer with software for base calling, allowing for sequence information about the template DNA strand to be obtained.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. For example, particle delivery can be practiced with array well sizing methods as described. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

We claim:

1. A method for determining sequence information about a template nucleic acid molecule comprising
   providing a substrate having a nanopore, the nanopore having a top opening and a bottom opening, and having a single polymerase enzyme attached proximal to an opening, the polymerase enzyme complexed with a primed template nucleic acid;
   contacting the substrate with a sequencing reaction mixture comprising reagents required for polymerase mediated nucleic acid synthesis including two or more different types of nucleotide analogs, each of the types comprising a current blockade label attached to the phosphate portion of the type of nucleotide analogs through a linker, such that when polymerase mediated nucleic acid synthesis occurs the label is cleaved, and each of the types of nucleotide analogs having different current blockade characteristics,
   providing a voltage drop across the nanopore, whereby when the base portion of a nucleotide analog, which is a molecule corresponding to one of the two or more types of nucleotide analogs, is associated with the polymerase enzyme while it is being incorporated into a growing strand during nucleic acid synthesis, the current blockage label on the nucleotide analog at least partially enters the nanopore, resulting in a measureable change in current through the nanopore;
   measuring the current through the nanopore over time to detect the incorporation of nucleotide analogs into the growing strand; and
   using the measured current over time while the nucleotide analog is associated with the polymerase to detect and identify the incorporated nucleotide, thereby obtaining sequence information about the template nucleic acid.

2. The method of claim 1 wherein each of the two or more types of nucleotide analogs has a different current blockade label.

3. The method of claim 1 wherein the sequencing reaction mixture comprises four different types of nucleotide analogs, each corresponding to the bases A, G, C, and T, or A, C, G, and U.

4. The method of claim 1 wherein the different current blockade characteristics comprise a different magnitude of the current through the nanopore.

5. The method of claim 1 wherein the different current blockage characteristics comprise the shape of the measured current through the nanopore over time.

6. The method of claim 1 wherein the different current blockage characteristics comprise different oscillation characteristics.

7. The method of claim 2 wherein the different current blockade labels have a different level of net charge.

8. The method of claim 2 wherein the different current blockade labels have a difference in length.

9. The method of claim 1 wherein the two or more different nucleotide analogs comprise linkers having different lengths.

10. The method of claim 1 wherein the nanopore comprises a solid state nanopore, a protein nanopore, or a hybrid nanopore comprising a solid state pore dimensioned and treated so as to accept a single protein nanopore.

11. The method of claim 1 wherein the polymerase is attached to the substrate.

12. The method of claim 1 wherein nanopore comprises a protein nanopore, and the polymerase enzyme and the protein nanopore together comprise a fusion protein.

13. The method of claim 1 wherein the voltage drop across the nanopore is provided such that positively charged molecules tend to be transported through the nanopore.

14. The method of claim 13 wherein the charge blockade labels have a net positive charge.

15. The method of claim 1 wherein a blockade label comprises a polymer of positively charged monomer units.

16. The method of claim 1 wherein a blockade label comprises a protein.

17. The method of claim 1 wherein the linker group comprises polyethylene glycol or a branched or linear alkane.

18. The method of claim 1 wherein the two or more types of nucleotide analogs comprise polyphosphate chains comprising 3, 4, 5, 6, 7, 8, or 9 phosphates.

19. The method of claim 1 wherein the nanopore has a diameter of about 4 nm to about 50 nm.

20. The method of claim 1 wherein the substrate comprises an array of nanopores providing sequence information.

21. The method of claim 1 wherein the substrate comprises a plurality of nanopores of claim 1.

* * * * *